United States Patent [19]
Frye et al.

[11] Patent Number: 5,637,691
[45] Date of Patent: Jun. 10, 1997

[54] STEROID DERIVATIVES, PHARMACEUTICAL COMPOSITIONS CONTAINING THEM, AND THEIR USE AS ANTIBIOTICS OR DISINFECTANTS

[75] Inventors: Leah L. Frye, Ravena, N.Y.; Michael A. Zasloff, Merion Station; William A. Kinney, Churchville, both of Pa.; Robert Moriarty, Oak Park, Ill.

[73] Assignee: Magainin Pharmaceuticals, Inc., Plymouth Meeting, Pa.

[21] Appl. No.: 290,826

[22] PCT Filed: Mar. 16, 1994

[86] PCT No.: PCT/US94/02397

§ 371 Date: Aug. 18, 1994

§ 102(e) Date: Aug. 18, 1994

[87] PCT Pub. No.: WO94/20520

PCT Pub. Date: Sep. 15, 1994

Related U.S. Application Data

[63] Continuation-in-part of Ser. No. 29,018, Mar. 10, 1993, abandoned.

[51] Int. Cl.[6] .......................... C07J 17/00; C07J 53/00; C07J 41/00
[52] U.S. Cl. .................... 540/106; 540/108; 552/506; 552/507; 552/521; 552/524; 552/540; 552/542; 552/544; 552/548; 552/550; 552/551; 552/552; 552/554; 552/557; 552/559; 552/582; 552/583; 552/584; 552/599; 552/600
[58] Field of Search ............................ 514/182; 552/521, 552/506, 507, 524, 540, 542, 544, 548, 550, 551, 552, 554, 557, 559, 582, 583, 584, 599, 609; 540/106, 108

[56] References Cited

U.S. PATENT DOCUMENTS

| | | |
|---|---|---|
| 3,016,390 | 1/1962 | Counsell . |
| 3,370,070 | 2/1968 | Klimstra et al. . |
| 4,220,598 | 9/1980 | Hixson, Jr. et al. ............... 424/1 |
| 4,372,888 | 2/1983 | Hjelmeland ............... 260/397.1 |
| 4,425,273 | 1/1984 | Iida et al. ............... 262/397.1 |
| 4,514,393 | 4/1985 | Castagnola et al. ............... 260/397.1 |
| 4,545,938 | 10/1985 | Mosbach et al. ............... 260/397.1 |
| 4,550,163 | 10/1985 | Voss et al. ............... 544/244 |
| 4,565,811 | 1/1986 | DiSchiena ............... 514/182 |
| 4,793,948 | 12/1988 | Hatono et al. ............... 260/397.1 |
| 4,966,897 | 10/1990 | Angelastro et al. ............... 514/177 |
| 5,004,737 | 4/1991 | Kim et al. ............... 514/182 |
| 5,057,509 | 10/1991 | Pellicciari et al. ............... 514/182 |
| 5,061,701 | 10/1991 | Pellicciari et al. ............... 514/182 |
| 5,063,222 | 11/1991 | Komoto et al. ............... 514/180 |
| 5,075,464 | 12/1991 | Blohm et al. ............... 552/522 |
| 5,192,756 | 3/1993 | Zasloff et al. ............... 514/182 |
| 5,250,524 | 10/1993 | Kramer et al. ............... 514/177 |

FOREIGN PATENT DOCUMENTS

| | | |
|---|---|---|
| 2361899 | 3/1978 | France . |
| 1565351 | 4/1980 | United Kingdom . |
| WO87/02367 | 4/1987 | WIPO . |

OTHER PUBLICATIONS

CA108:75714, 1986.
K.S. Moore et al., "Squalamine: An aminosterol antibiotic from the shark," Proc. Natl. Acad. Sci. USA, vol. 90, Feb. 1993, pp. 1354–1358.
A.M. Bellini et al., "Antimicrobial Activity of Basic Cholane Derivatives Part IX," Arch. Pharm. (Weinheim), vol. 323, 1990, pp. 201–205.
A.M. Bellini et al., "Antimicrobial activity of basic cholane derivatives, X," Steroids, vol. 56, Jul. 1991, pp. 395–397.
J. McKenna et al., "Bis–steroids as Potential Enzyme Models," J.C.S. Chem. Comm., 1977, pp. 809–811.
S.L. Wehrli et al., "Structure of the novel steroidal antibiotic squalamine determined by two–dimensional NMR spectroscopy," Steriods, vol. 58, No. 8, Aug. 1993.

*Primary Examiner*—Rebecca Cook
*Attorney, Agent, or Firm*—Finnegan, Henderson, Farabow, Garrett & Dunner, L.L.P.

[57] ABSTRACT

Compounds having a broad range of antimicrobial activity generally have a structure including asteroid nucleus with a cationic, preferably polyamine, side chain (X) and an anionic side chain (Y). The invention is also directed to compounds of the Formula III:

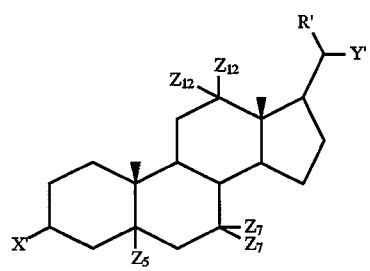

preferably where the steroid ring nucleus is saturated; the steroid ring substituent $Z_5$ is α-H; one $Z_7$ is β-H and the other is α-H or α-OH; both substituents $Z_{12}$ are hydrogen; X' is a polyamine side chain of the formula —NH—$(CH_2)_p$—NH—$(CH_2)_q$—N($R''$)($R'''$) where p and q are each independently 3 or 4, and $R''$ and $R'''$ are each independently hydrogen or methyl; R' is methyl; and Y' is ($C_1$-$C_{10}$)-alkyl substituted with a group such as —$CO_2H$ or —$SO_3H$.

11 Claims, No Drawings

5,637,691

STEROID DERIVATIVES, PHARMACEUTICAL COMPOSITIONS CONTAINING THEM, AND THEIR USE AS ANTIBIOTICS OR DISINFECTANTS

CROSS-REFERENCE TO RELATED APPLICATION

This application is a 371 of PCT/US94/02397 filed Mar. 10, 1994, published as WO94/20520, Sep. 15, 1994 and a continuation-in-part of U.S. patent application Ser. No. 08/029,018, filed Mar. 10, 1993 now abandoned.

BACKGROUND OF THE INVENTION

Squalamine, 3β-(N-[3-aminopropyl]-1,4-butanediamine)-7α,24ζ-dihydroxy-5α-cholestane 24-sulfate, is an aminosterol that has been isolated from the dogfish shark, *Squalus acanthias*. See K. Moore, S. Wehrli, H. Roder, M. Rogers, J. Forrest, D. McCrimmon, and M. Zasloff, *Proc. Nat. Acad. Sci.* (USA), Vol. 90, February 1993, 1354–1358. See also U.S. Pat. No. 5,192,756 to Zasloff et al.

This water-soluble steroid exhibits potent bactericidal activity against both gram-positive and gram-negative bacteria. In addition, squalamine is antifungal and exhibits lytic activity against protozoa. The molecule was initially recovered as a natural product through extraction of several tissues of the dogfish shark, including the stomach, liver, gallbladder and spleen. Its structure was determined by fast atom bombardment mass spectroscopy and NMR spectroscopy (S. Wehrli et al., *Steroids* 58, 1993, 370–378). The chemical structure of squalamine is that of a cationic steroid characterized by a condensation of an anionic bile salt intermediate with spermidine. Squalamine represented the first example of asteroid to which spermidine is covalently coupled and a new class of antibiotics (K. Moore, S. Wehrli, H. Roder, M. Rogers, J. Forrest, D. McCrimmon, and M. Zasloff, *Proc Nat. Aced. Sci.* (USA), Vol. 90, February 1993, 1354–1358).

SUMMARY OF THE INVENTION

One aspect of the present invention relates to sterol antibiotics other than squalamine of the Formula I:

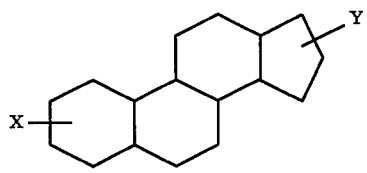

wherein X and Y are each independently selected from a cationic hydrophilic side chain and an anionic hydrophilic side chain; and the steroid ring nucleus is saturated, unsaturated or partially saturated, and is optionally substituted with at least one group selected from —OH, —$NH_2$, —SH, —F and alkyl. The invention also relates to pharmaceutical compositions containing such compounds and their use as antimicrobials or antibiotics. The invention further relates to the use of such compounds as disinfectants or anti-infectives.

Preferred compounds are of the Formula II:

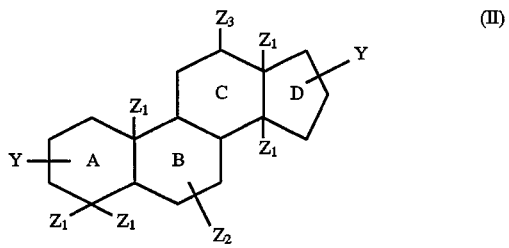

wherein each $Z_1$ is independently selected from H and $C_1$-$C_4$ alkyl; and $Z_2$ and $Z_3$ are each independently selected from H, OH, $NH_2$ and SH.

Another aspect of this invention relates to compounds other than squalamine of the Formula III:

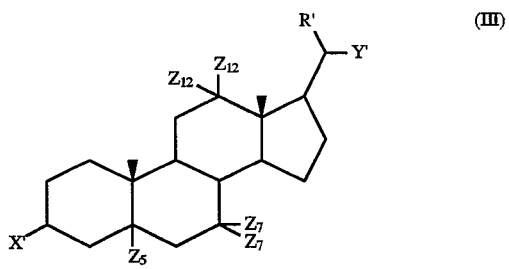

wherein: the steroid ring nucleus is saturated or unsaturated; the steroid ring substituent $Z_5$ is selected from α-H and β-H; each of the steroid ring substituents $Z_7$ is selected from —H, —OH, —SH, —F, —$NH_2$, —($C_1$-$C_3$)-alkyl and —($C_1$-$C_3$)-alkoxy; one of the steroid ring substituents $Z_{12}$ is —H and the other is selected from —H and —OH; X' is a polyamine side chain of the formula —$X_1$—$(CH_2)_p$—$X_2$—$(CH_2)_q$—N($R^{II}$)($R^{III}$), where one of $X_1$ and $X_2$ is —N($R^{IV}$) and the other is independently selected from —N($R^V$), —O, —S and —$CH_2$, with $R^{IV}$ and $R^V$ being independently selected from —H and —($C_1$-$C_3$)-alkyl, p and q are each independently an integer of from 0 to 5 but both p and q are not 0, and $R^{II}$ and $R^{III}$ are each independently selected from —H, —($C_1$-$C_3$)-alkyl and —$(CH_2)_r$—N($R_{10}$)($R_{11}$) where r is an integer from 2 to 5 and $R_{10}$ and $R_{11}$ are each independently selected from —H and —($C_1$-$C_3$)-alkyl; R' is selected from —H and —($C_1$-$C_3$)-alkyl; and Y' is —($C_1$-$C_{10}$)-alkyl optionally substituted with one or more groups selected from —$CO_2$H, —OH, —NH—$SO_2CF_3$, —$SO_3$H, —$PO_3H_2$, —$OSO_3$H, —$CF_3$, —F,

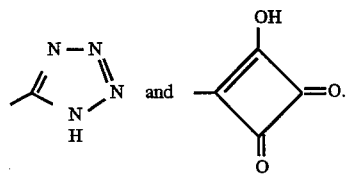

DETAILED DESCRIPTION OF PREFERRED EMBODIMENTS

The present invention is directed to steroid compounds other than squalamine of the Formula I:

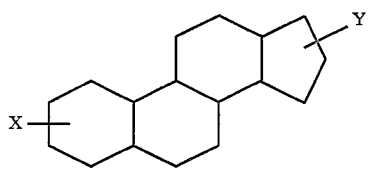

wherein X and Y are each independently selected from a cationic hydrophilic side chain and an anionic hydrophilic side chain; and the steroid ring nucleus,

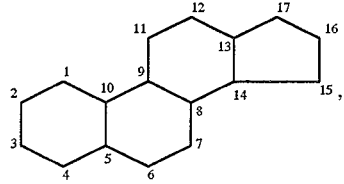

is saturated, partially saturated or unsaturated, and is optionally substituted with at least one group selected from —OH, —NH$_2$, —SH and alkyl, preferably —OH.

Compounds of the Formula I preferably have a net positive charge. Preferably X is a cationic side chain and Y is an anionic side chain. On the steroid ring nucleus, X is preferably at position 3, 15, 16 or 17 and at a position different from that of Y, more preferably at position 3. Y is preferably at position 3, 15, 16 or 17, preferably at position 17. Each side chain, as an independent compound, is hydrophilic and preferably water-soluble.

The anionic side chain, Y, is a hydrocarbon chain substituted with a negatively charged group, preferably sulfate, sulfite, carboxylate or phosphate, more preferably sulfate. The hydrocarbon chain may be, for example, aliphatic, cycloaliphatic or aromatic, and may be saturated or unsaturated. The anionic side chain is hydrophilic and therefore the hydrocarbon generally has no more than twelve carbon atoms.

The anionic side chain may also be a hydrocarbon chain having at least one carboxyl group or carboxylate group, e.g., —R$_1$—COOM wherein R$_1$ is a C$_1$-C$_{12}$ hydrocarbon, such as a C$_1$-C$_{12}$ alkyl, and M is hydrogen or an appropriate ionizable cation, e.g., sodium or potassium. The hydrocarbon chain may further have a negatively charged group, such as sulfate, sulfite or phosphate.

The anionic side chain may also be a substituted amide wherein the substituent group of the amide is a hydrocarbon chain substituted with at least one negatively charged group such as phosphate, sulfate, sulfite, carboxylate, sulfonate or phosphonate, e.g.:

$$-R_2-\overset{O}{\underset{\|}{C}}-NH-R_3$$

wherein R$_2$ is a C$_1$-C$_{12}$ hydrocarbon group and R$_3$ is a hydrocarbon group substituted with a sulfate, sulfite, phosphate, carboxylate, sulfonate or phosphonate group. R$_2$ and R$_3$ may be the same or different hydrocarbon groups. The hydrocarbon groups are preferably aliphatic and contain no more than about nineteen carbon atoms. Thus, for example, R$_3$ may be —(CH$_2$)$_2$—SO$_3$H.

The anionic side chain Y may also contain an oxygen, nitrogen or sulfur atom linking Y to the C-17 position of the steroid ring nucleus.

Particularly preferred anionic side chains include the following:

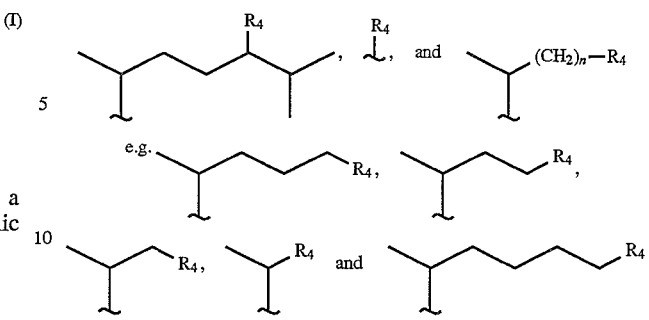

where R$_4$ is OSO$_3{}^-$, OPO$_3{}^-$, CO$_2{}^-$ or OSO$_2$—, and n is an integer of from 1 to 18.

The cationic side chain, X, is a hydrophilic amine which has at least one amino group that is not directly linked to the steroid ring nucleus. The amine may be, for example, an aliphatic amine, cycloaliphatic amine, heterocyclic amine or aromatic amine, provided that there is at least one positively charged amine group in the side chain. The cationic side chain, which includes at least one positively charged amine group, may be linked to the steroid ring nucleus through one of the following groups: —NR$_5$—, where R$_5$ is a hydrocarbon, more particularly an alkyl, or hydrogen; —S—; or —O—.

Thus, the cationic side chain may be depicted by the formula R$_6$—Z, wherein Z is —NR$_5$ as defined above, —S— or —O—, and R$_6$ is an organic amine. The organic amine may be a hydrocarbon amine wherein the amine group is in the hydrocarbon chain (such as in a polyamine or heterocyclic amine) or where the amine group is a substituent group on the hydrocarbon side chain. Thus, for example, the cationic side chain may be an aliphatic polyamine containing two or more amine groups, such as spermidine or ethylene diamine; or a heterocyclic amine such as pyridine or pyrrolidine; or an organic amine, such as an alkylamine. The organic amine may also be a peptide or an amino acid containing at least one positively charged amino group. Thus, for example, the peptide may include arginine, lysine or histidine, or R$_6$ may be an amino acid such as arginine, lysine, etc. The organic amine may also be an amine substituted sugar such as glucosamine and galactosamine.

As hereinabove indicated, the cationic side chain is hydrophilic and therefore the number of carbon atoms in the hydrocarbon moieties is such as to retain hydrophilicity. In general, the hydrocarbon moieties contain no more than 12 carbon atoms.

Particularly preferred cationic side chains include:

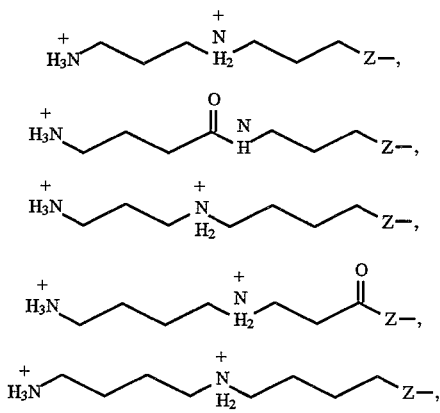

-continued

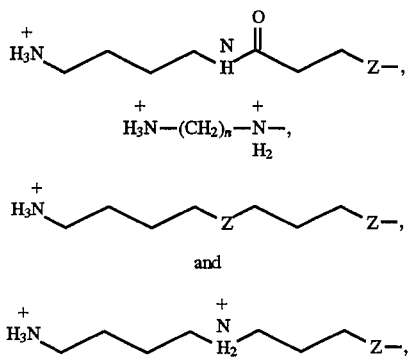

wherein Z is O, S or NR$_5$, where R$_5$ is hydrogen or alkyl; and n is an integer of from 2 to 12.

The steroid ring nucleus may be saturated, partially saturated or unsaturated, and is preferably saturated. The steroid ring also preferably includes at least one hydrophilic substituent group at a position on the steroid ring nucleus different from both the X and Y side chains. Such hydrophilic substituent group is generally —OH, —NH$_2$ or —SH, preferably —OH.

Preferred compounds of the invention are those of the Formula II:

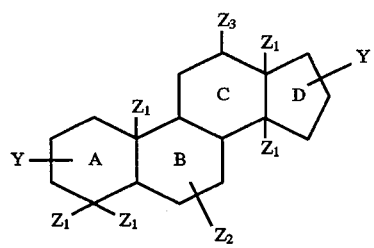

(II)

wherein each Z$_1$ is independently selected from H and C$_1$-C$_4$ alkyl; and Z$_2$ and Z$_3$ are each independently selected from H, OH, NH$_2$ and SH. Preferably, the Z$_2$ and Z$_3$ hydrophilic substituent groups are located at position 6, 7, 11 and/or 12 of the steroid ring nucleus.

The alkyl group of Z$_1$ is preferably substituted at position 10 and/or 13, more preferably at both positions, of the steroid ring nucleus. When the steroid ring nucleus includes an alkyl substituent group(s), it is preferably located in a plane opposite to the plane of the hydrophilic substituent group(s). Thus, if the hydrophilic group(s) are alpha group(s), the alkyl group(s) are beta group(s) and vice-versa.

Preferred compounds are of the following formulae, wherein X, Y, Z$_1$, Z$_2$ and Z$_3$ are as defined above:

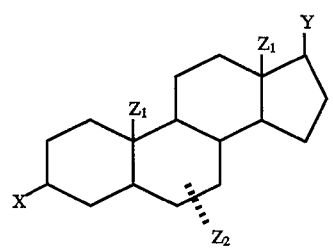

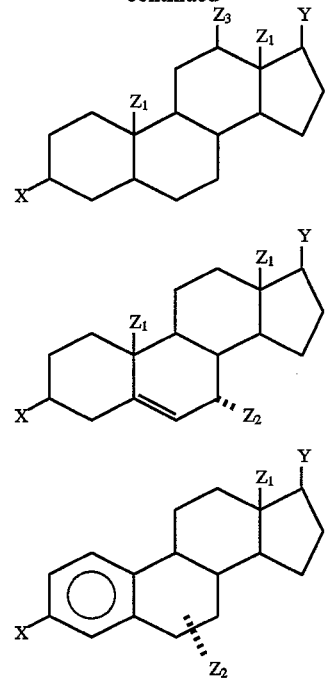

The invention is also directed to compounds other than squalamine of the Formula III:

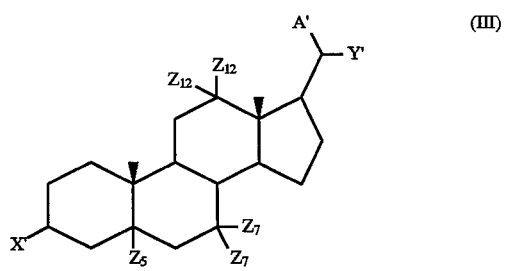

(III)

wherein:

the steroid ring nucleus is saturated or unsaturated (e.g., with double bonds at positions C1-C2, C8-C9, C9-C11 and/or C8-C14);

the steroid ring substituent Z$_5$ is selected from α-H and β-H;

each of the steroid ring substituents Z$_7$ is selected from —H, —OH, —F, —(C$_1$-C$_3$)-alkyl and —(C$_1$-C$_3$)-alkoxy;

one of the steroid ring substituents Z$_{12}$ is —H and the other is selected from —H and —OH;

X' is a polyamine side chain of the formula

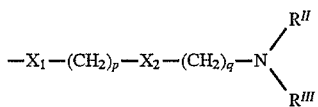

where one of $X_1$ and $X_2$ is —$N(R^{IV})$ and the other is independently selected from —$N(R^V)$, —O, —S and —$CH_2$, where $R^{IV}$ and $R^V$ are each independently selected from —H and —($C_1$-$C_3$)-alkyl, p and q are each independently an integer of from 0 to 5 but both p and q are not 0, and $R^{II}$ and $R^{III}$ are each independently selected from —H, —($C_1$-$C_3$)-alkyl and —$(CH_2)_r$—$N(R_{10})(R_{11})$ where r is an integer from 2 to 5 and $R_{10}$ and $R_{11}$ are each independently selected from —H and —($C_1$-$C_3$)-alkyl;

R' is selected from —H and —($C_1$-$C_3$)-alkyl; and

Y' is —($C_1$-$C_{10}$)-alkyl optionally substituted with at least one of the following groups: —$CO_2H$, —OH, —NH—$SO_2CF_3$, —$SO_3H$, —$PO_3H_2$, —$OSO_3H$, —$CF_3$, —F,

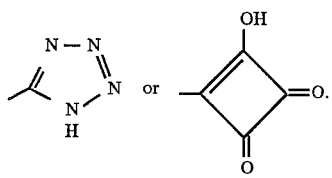

Preferably: the steroid ring nucleus is saturated; $Z_5$ is α-H; one $Z_7$ is β-H, and the other $Z_7$ is α-H or α-OH; and one $Z_{12}$ is β-H, and the other $Z_{12}$ is α-H or α-OH, more preferably α-H. Preferred substituted steroid nuclei include:

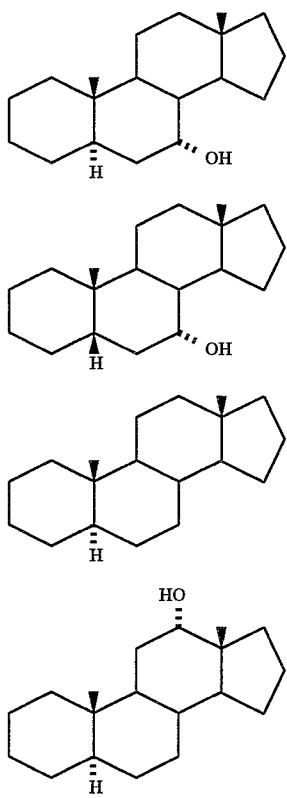

Preferably, the polyamine side chain X' is β to the steroid ring nucleus, and p and q are independently selected from integers of from 1 to 5. More preferably, one of $X_1$ and $X_2$ is —$N(R^{IV})(R^V)$ and the other is independently selected from —$N(R^{IV})(R^V)$, —O and —S, where $R^{IV}$ and $R^V$ are each independently selected from —H and —($C_1$-$C_3$)-alkyl, and p and q are each independently an integer of from 2 to 5. Particularly preferred polyamine side chains include those where $X_1$ and $X_2$ are both —NH, p and q are independently 3 or 4, and $R^{II}$ and $R^{III}$ are independently selected from hydrogen, methyl and —$(CH_2)_r$—$N(R_{10})(R_{11})$ where r is an integer of 3 or 4 and $R_{10}$ and $R_{11}$ are each independently selected from hydrogen and methyl. Preferred polyamine side chains include the following:

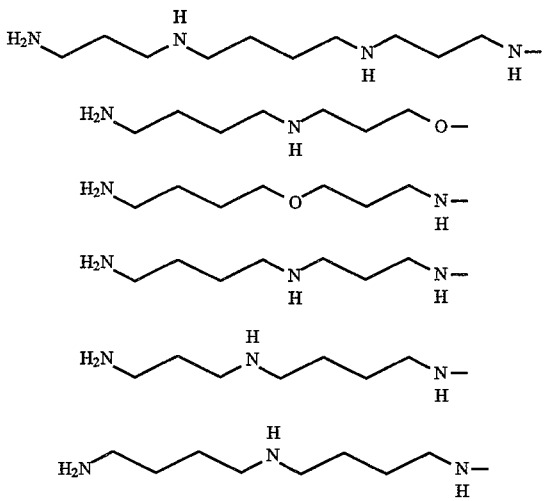

Preferably, R' is α-methyl, and the side chain containing Y' is β to the steroid ring nucleus with Y' being —($C_2$-$C_8$)-alkyl that is unsubstituted or substituted with one of the groups defined above, more preferably —$SO_3H$ or —$CO_2H$. Preferred Y' chains include:

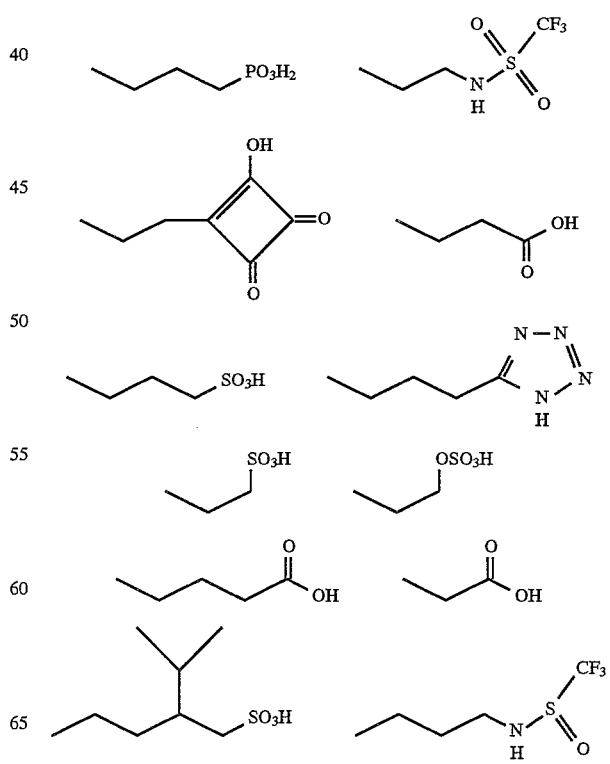

9
-continued

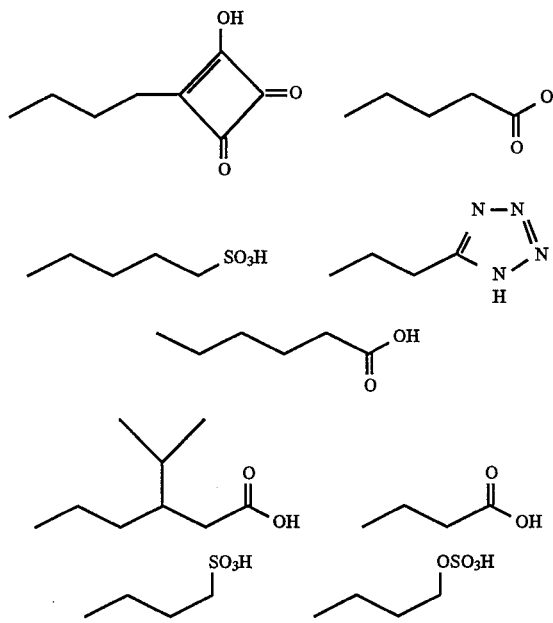

Particularly preferred Y' chains include those of the formula —(CH$_2$)$_s$CH(R$_{12}$)(R$_{13}$), where s is an integer of from 0 to 8, and one of R$_{12}$ and R$_{13}$ is selected from hydrogen and —(C$_1$-C$_3$)-alkyl and the other is selected from —CO$_2$H, —NH—SO$_2$CF$_3$, —SO$_3$H, —PO$_3$H$_2$, —OSO$_3$H, —OH,

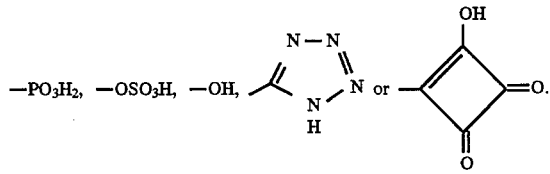

Especially preferred compounds other than squalamine, which are useful as anti-infectives or disinfectants, are of the Formula III wherein:

the steroid ring nucleus is saturated;

the steroid ring substituent Z$_5$ is α-H;

one Z$_7$ is β-H and the other is α-H or α-OH;

both substituents Z$_{12}$ are hydrogen;

10

X' is a polyamine side chain of the formula

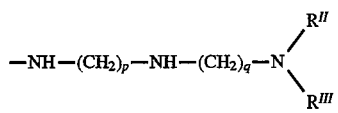

where p and q are each independently 3 or 4, and R$^{II}$ and R$^{III}$ are each independently selected from hydrogen and methyl;

R' is α-methyl; and

Y' is —(C$_1$-C$_{10}$)-alkyl optionally substituted with —CO$_2$H, —SO$_3$H, —PO$_3$H$_2$, —OSO$_3$H, —NHSO$_2$CF$_3$,

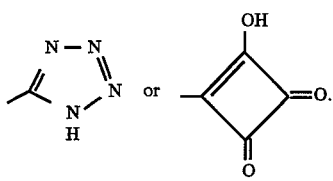

A particularly preferred polyamine side chain X' is spermine, i.e., —NH—(CH$_2$)$_3$—NH—(CH$_2$)$_4$—NH—(CH$_2$)$_3$—NH$_2$. A preferred Y' chain has the formula

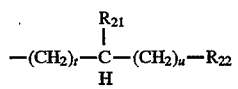

where one of R$_{21}$ and R$_{22}$ is —H or —(C$_1$-C$_3$)-alkyl and the other is —CO$_2$H, —OH, —NH—SO$_2$CF$_3$, —SO$_3$H, —PO$_3$H$_2$, —OSO$_3$H, —CF$_3$, —F,

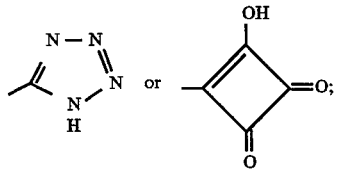

and t is an integer of from 0 to 5, and u is an integer of from 0 to 3.

Where reference is made herein to "hydrocarbon" or "alkyl" groups, it will be understood that these groups may be branched or straight chain.

The compounds of the invention include stereoisomers of compounds of the general formulae and prodrugs thereof, as well as pharmaceutically acceptable salts of such compounds. The compounds of the invention include those of the above general Formulae I, II or III and their salts, as optically pure stereoisomers or as a mixture of stereoisomers.

Preferred compounds of the invention include the following:

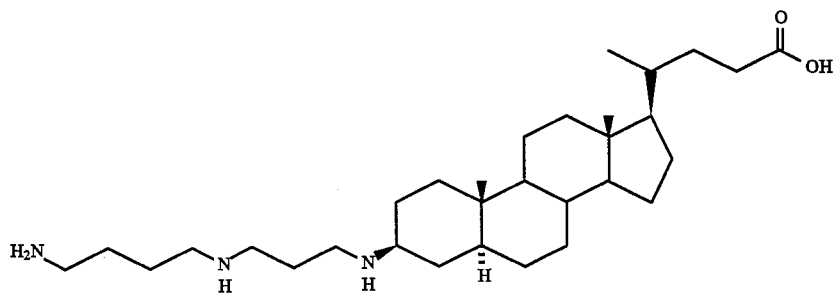

-continued
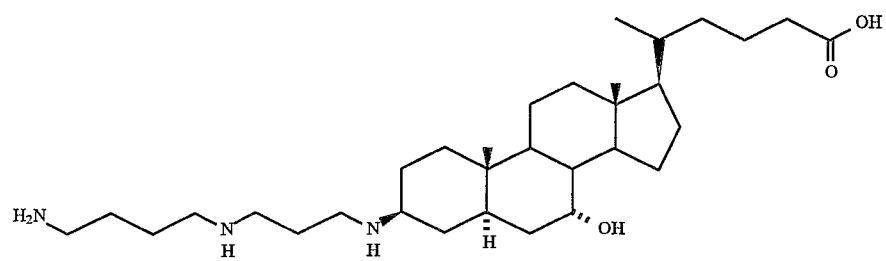
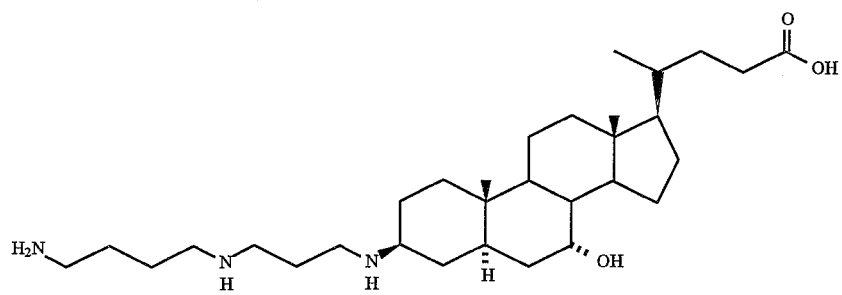
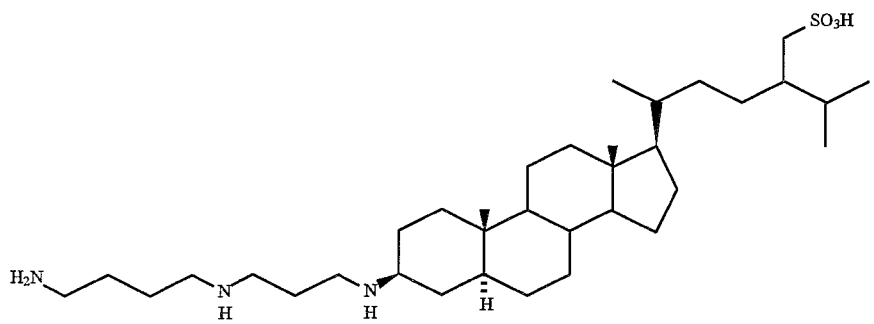
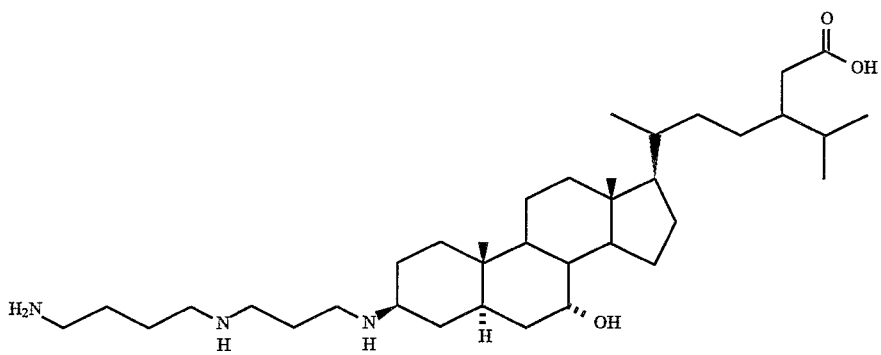
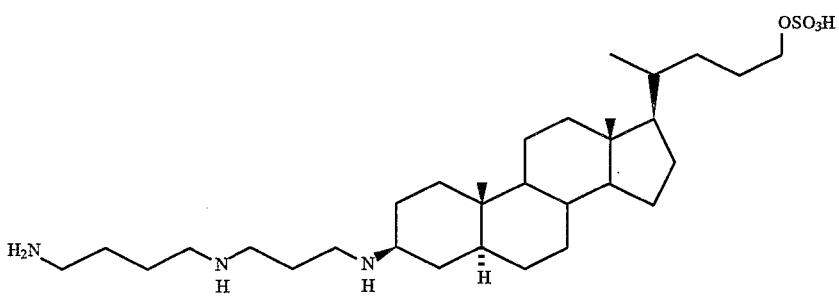

-continued
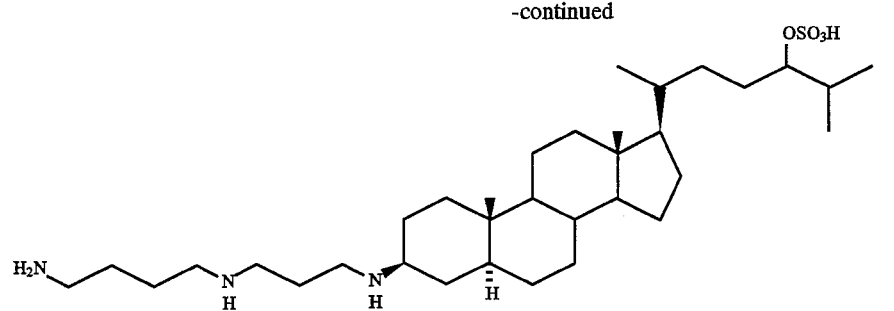
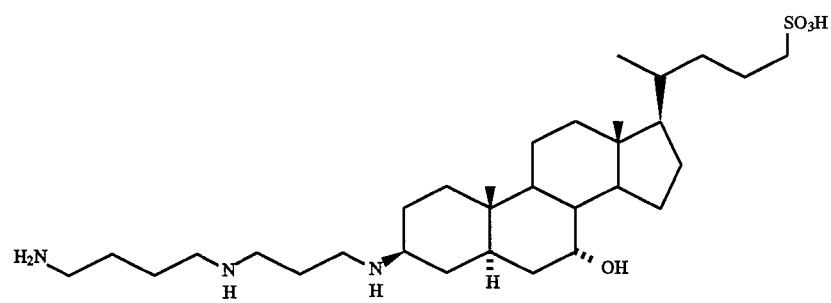
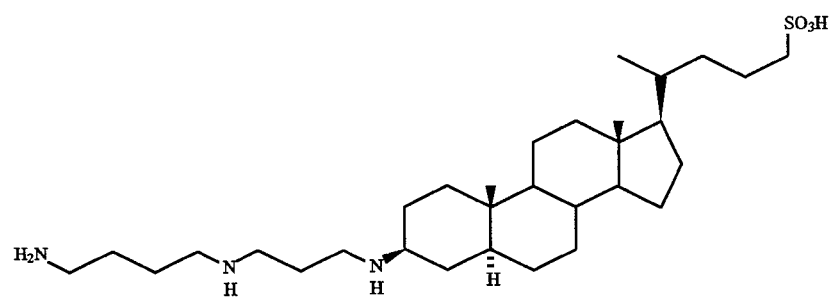
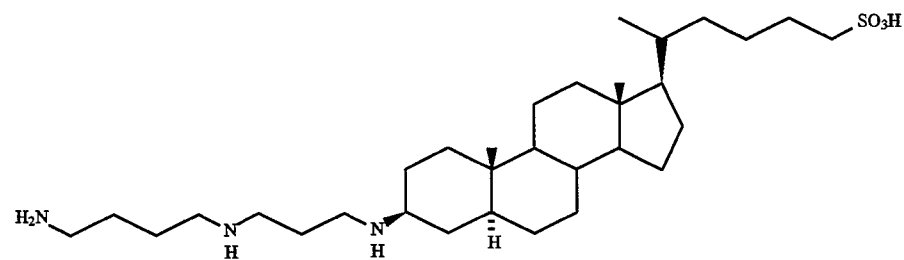
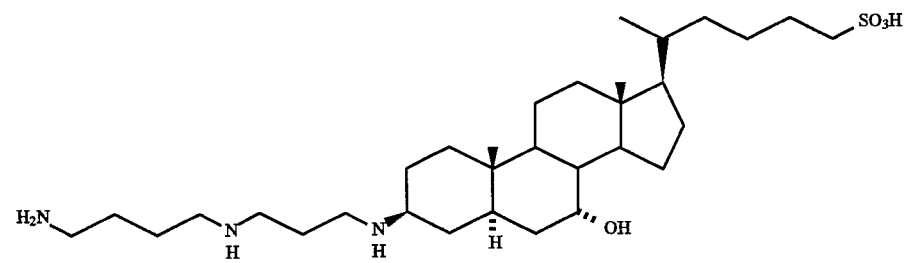
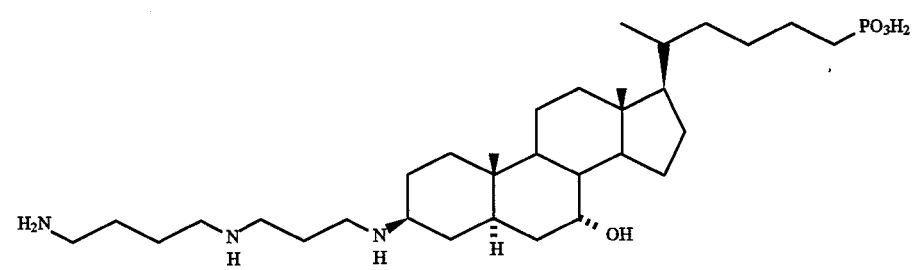

-continued
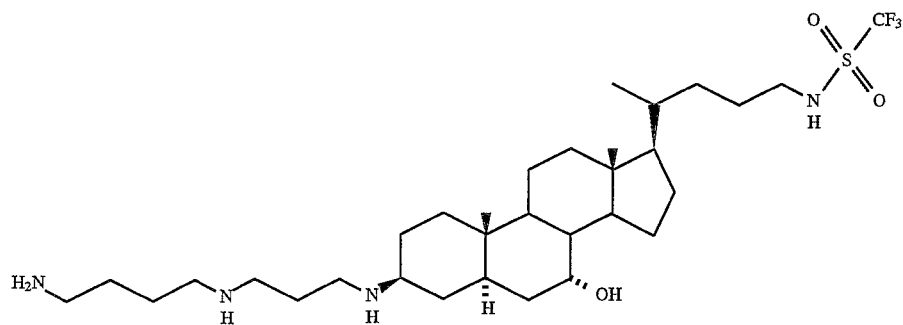
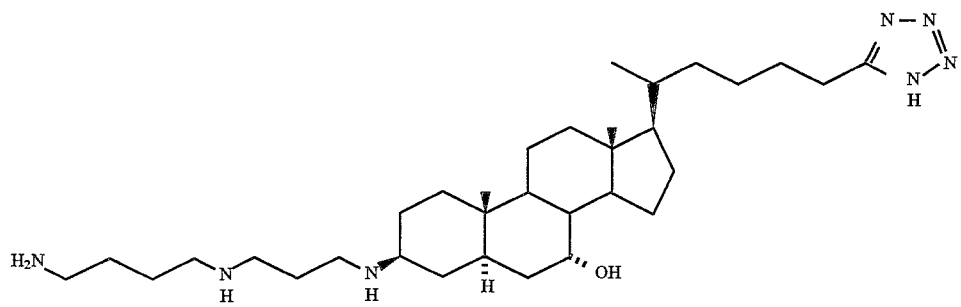
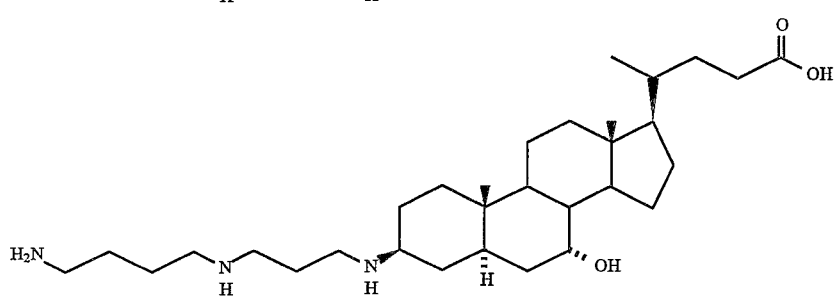
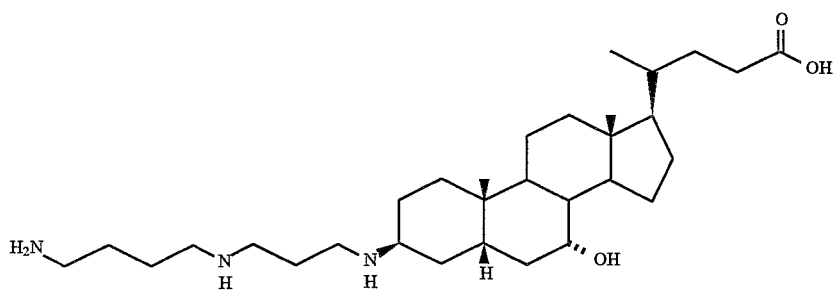
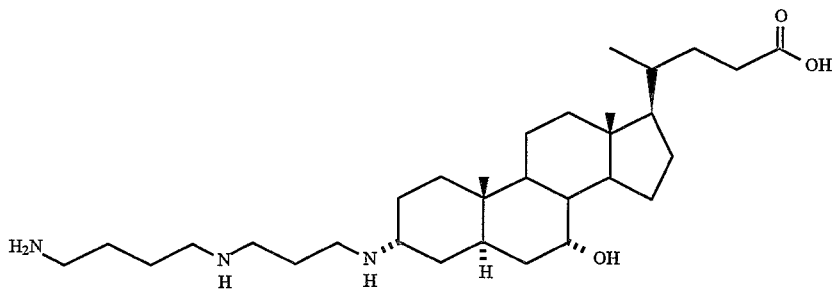

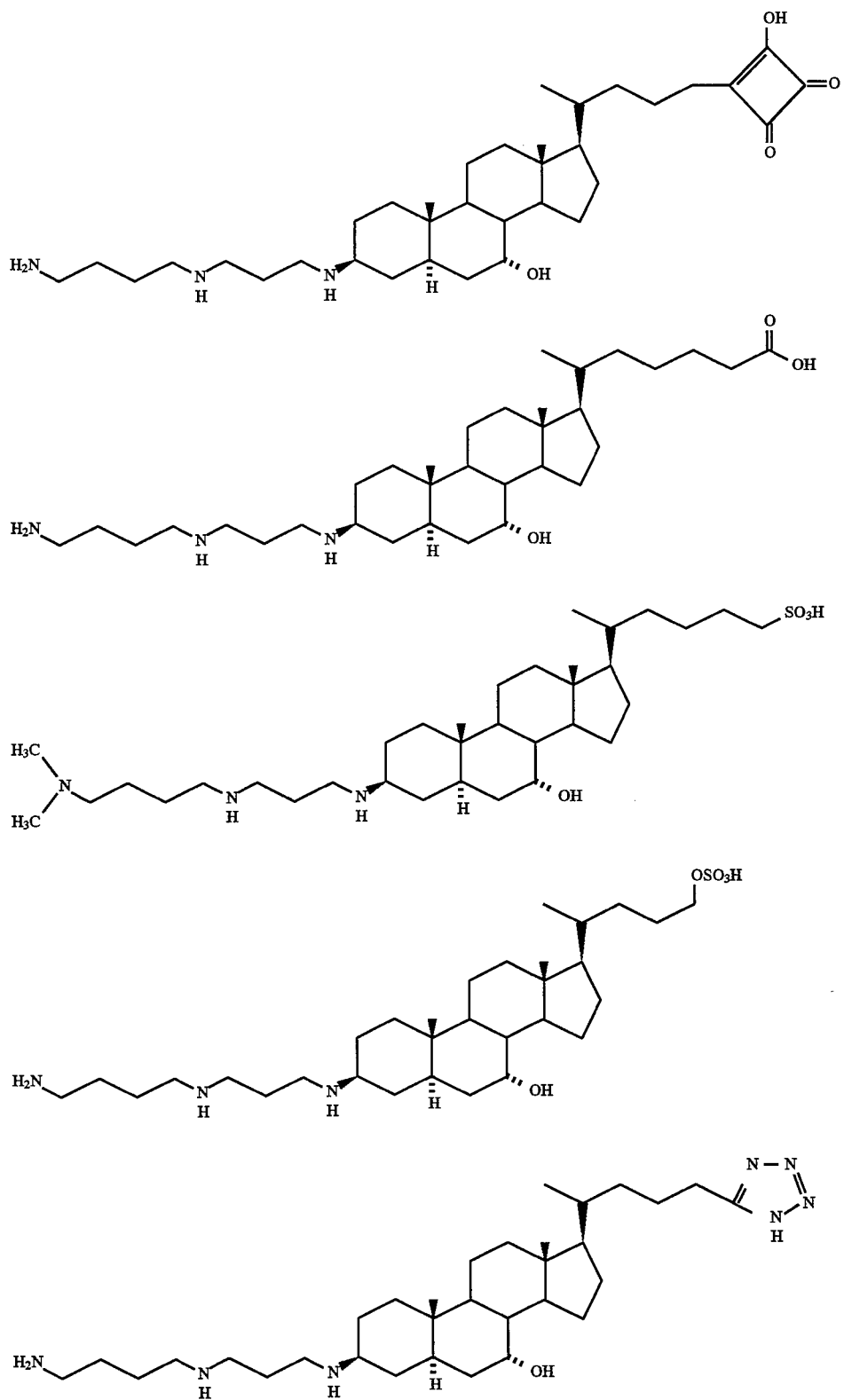

-continued
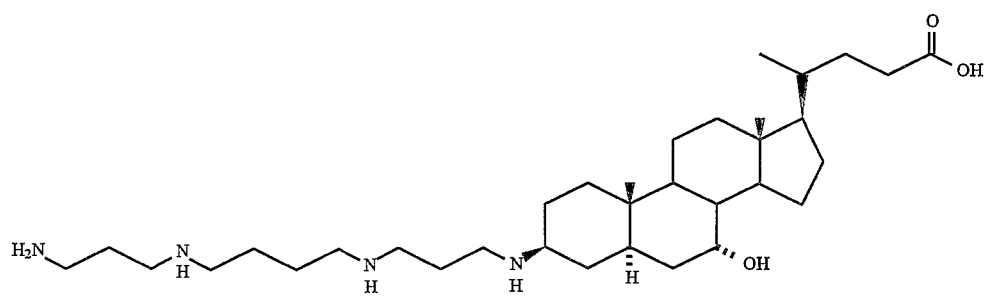
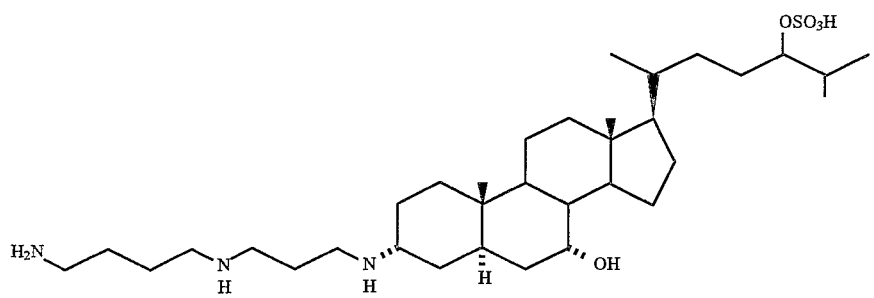
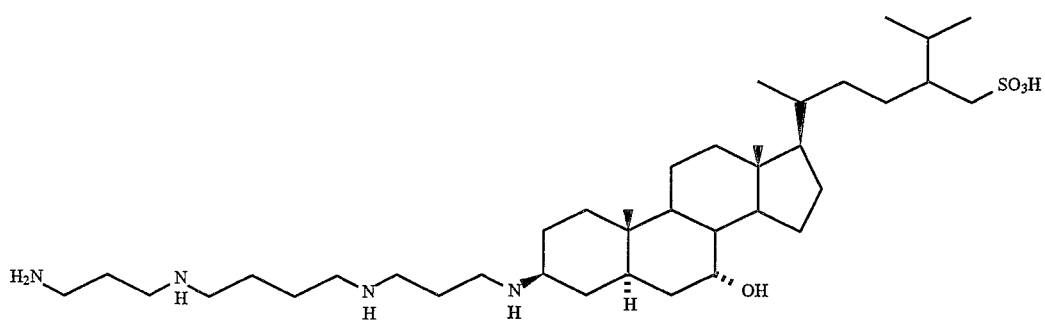
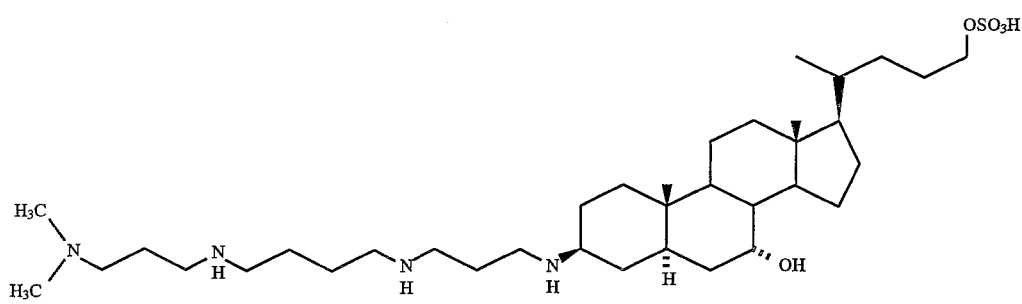
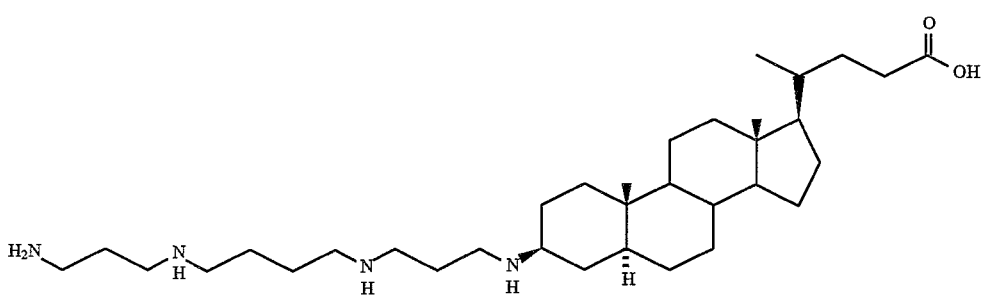

-continued
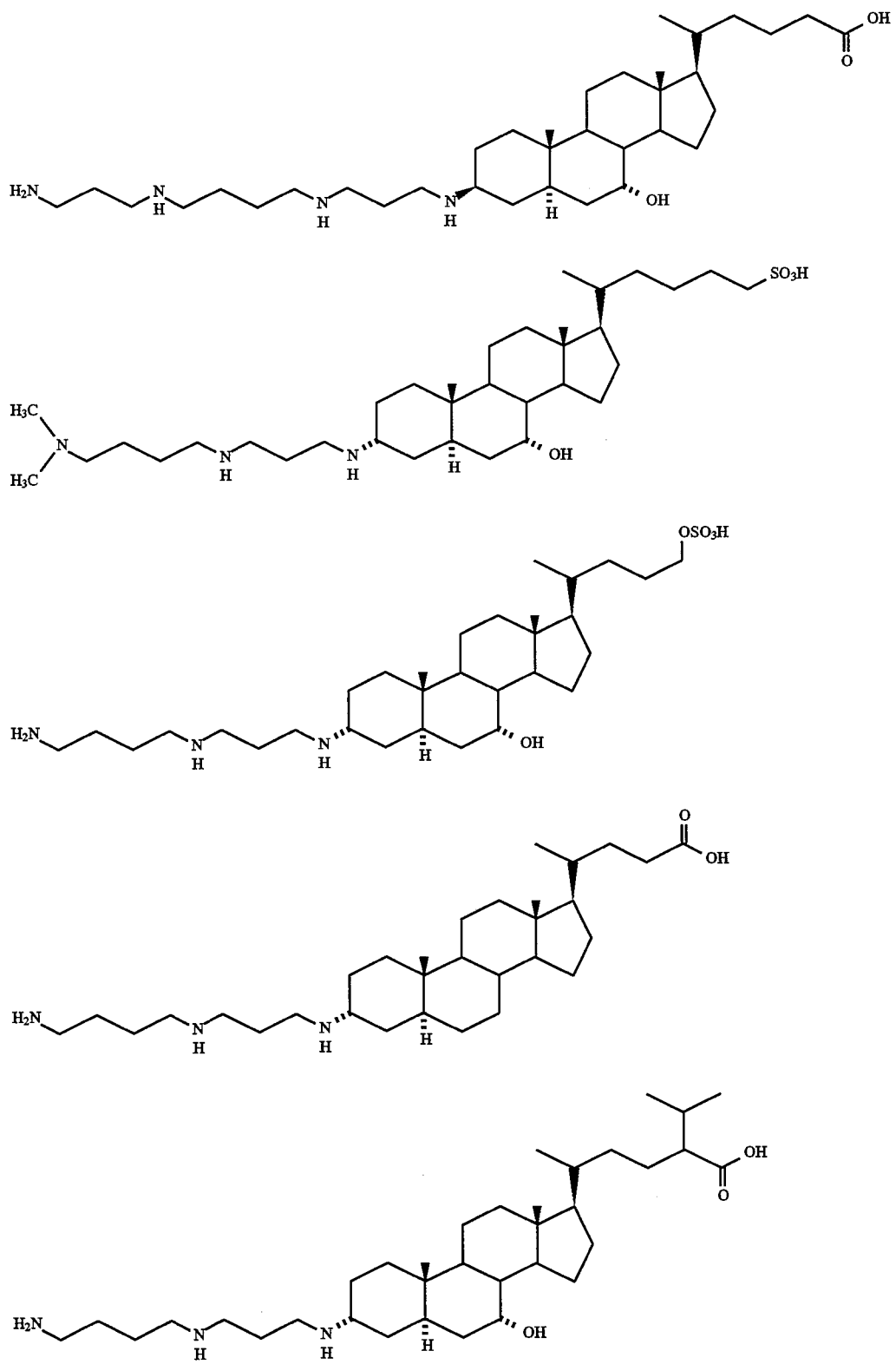

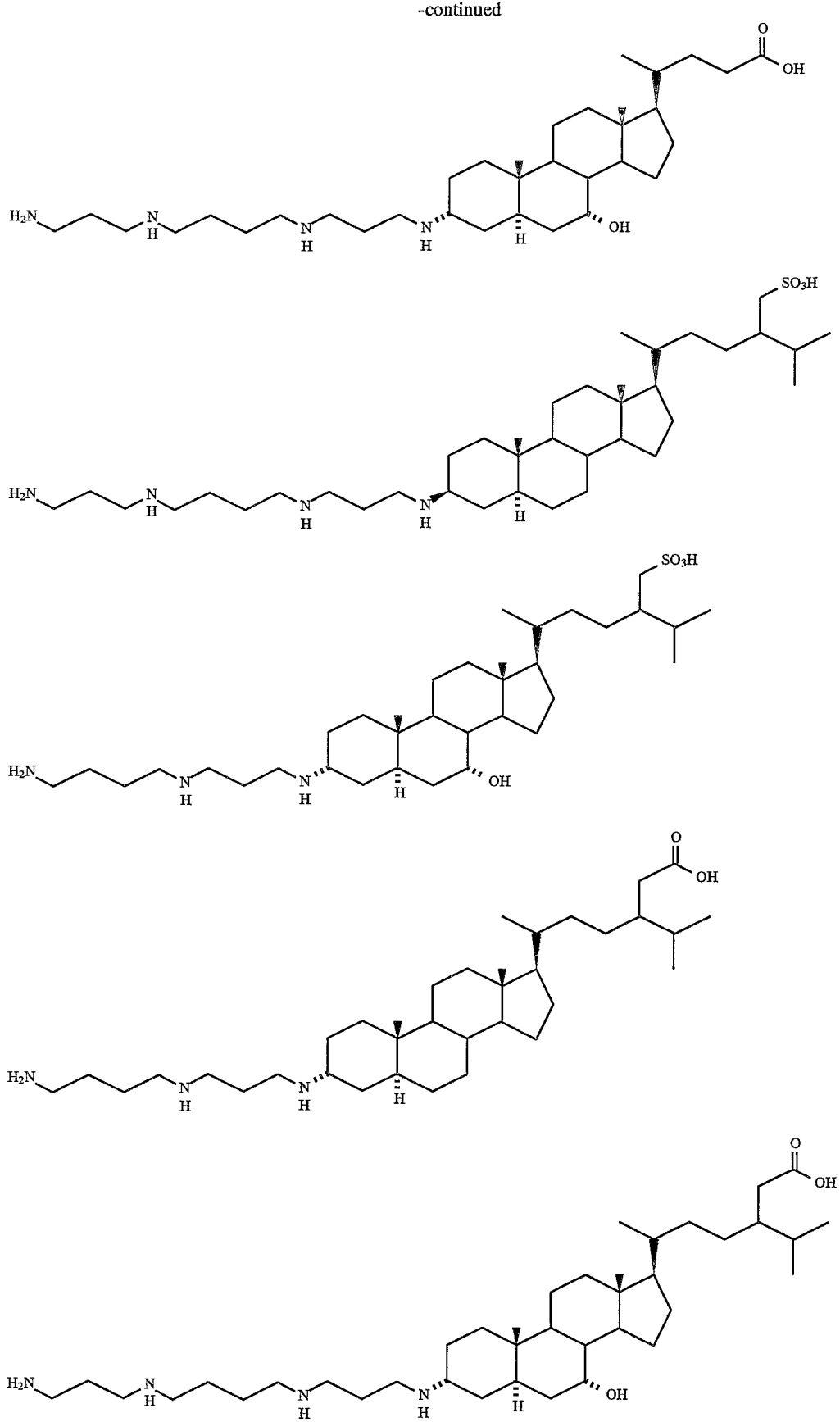

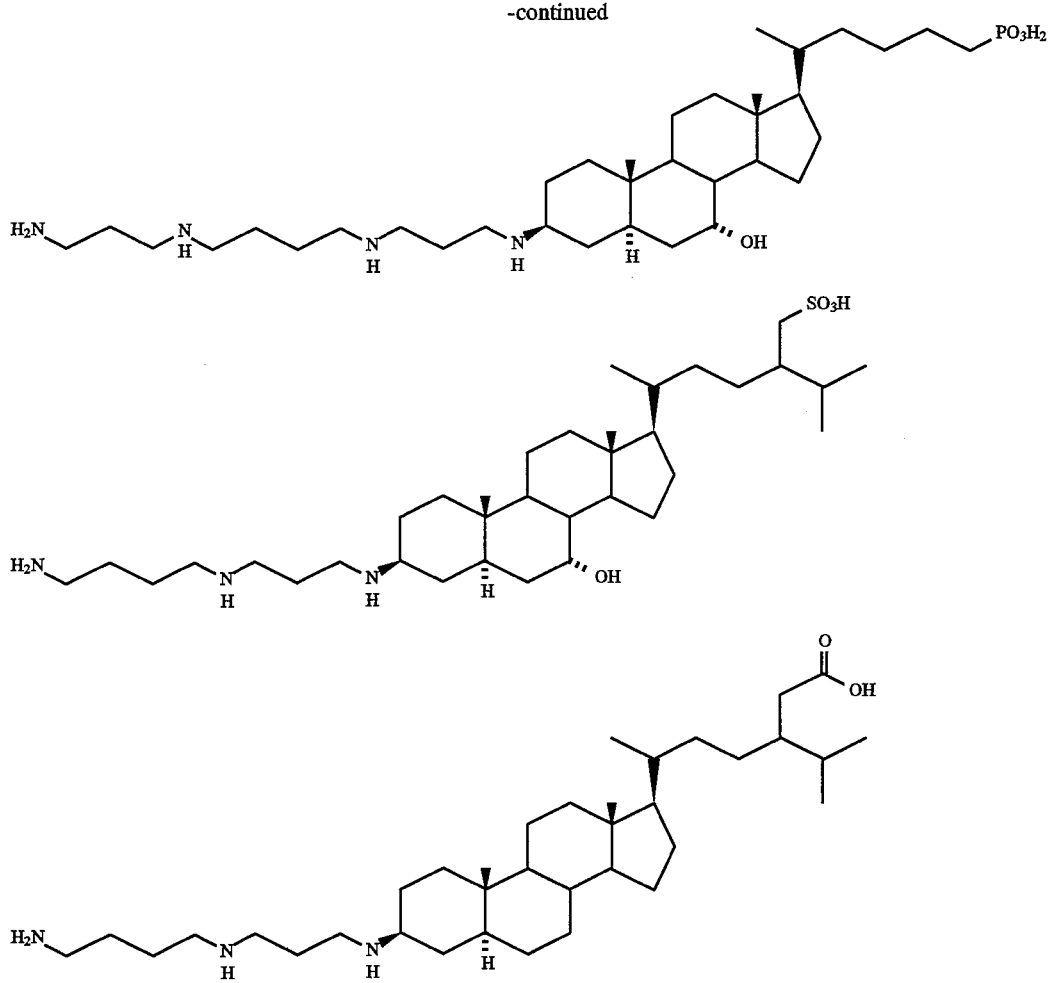

Preferred compounds of the invention are also set forth in the examples below.

Syntheses

Compounds of the invention may be synthesized as described in the examples below.

EXAMPLE A

A suitably protected flat ring nucleus is constructed. In many cases, this flat ring system already has an attached side chain which will become the anionic side chain. Flat ring systems with the anionic side chain attached are synthesized as described in Examples A(1)–(8). Flat ring systems which have at least part of the anionic side chain added are synthesized as described in Examples A(9)–(12). Preparation of the cationic side chain is described in Example A(13). Attachment of the cationic side chain through the C-3 amine, alcohol or thiol is exemplified in Example A(14). Introduction of an anionic group into an anionic side chain is then exemplified. Sulfation is illustrated by Example A(15). Introduction of phosphate is illustrated by Example A(16). Preparation of carboxylates is illustrated by Example A(17).

EXAMPLE A(1)
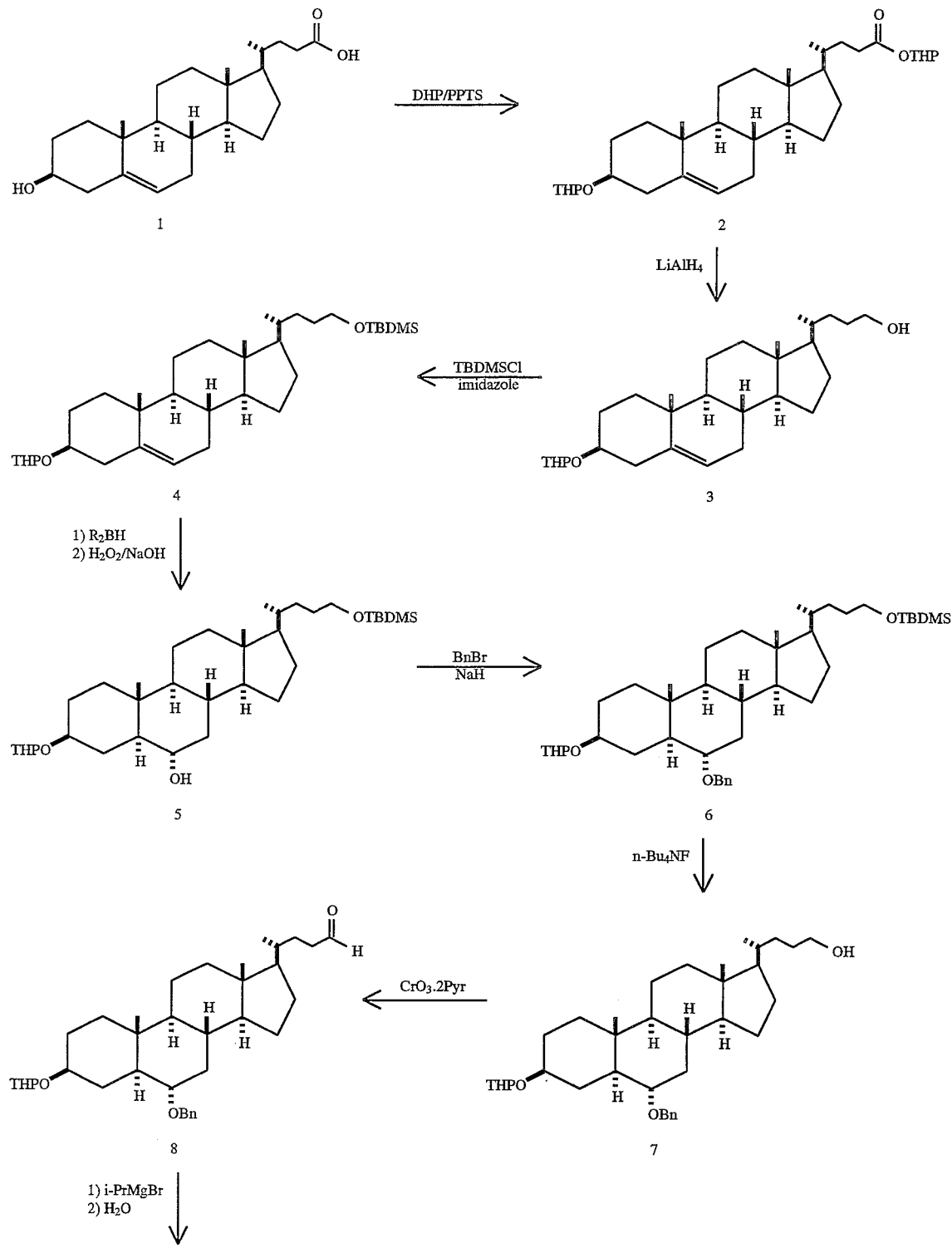

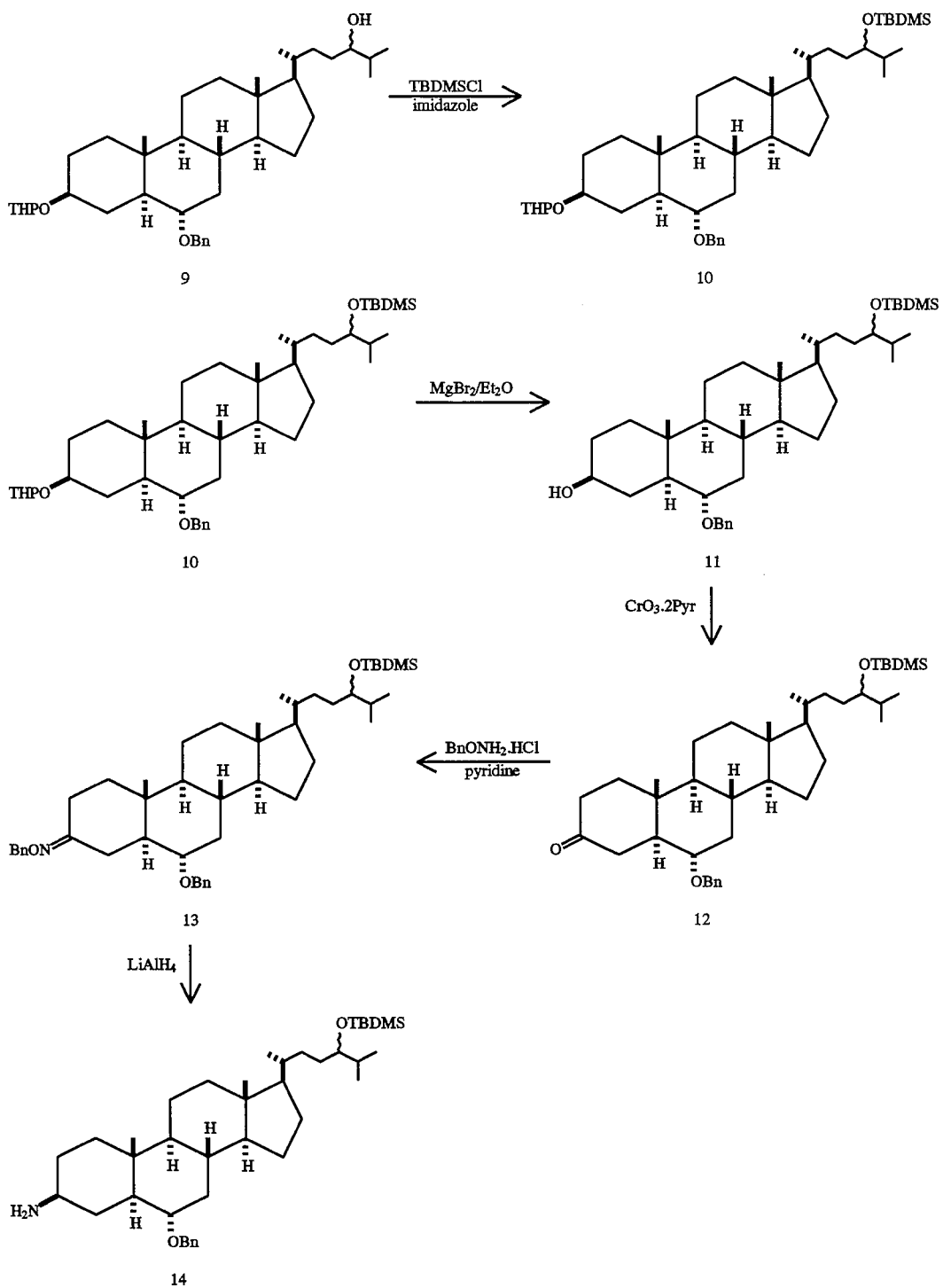
-continued

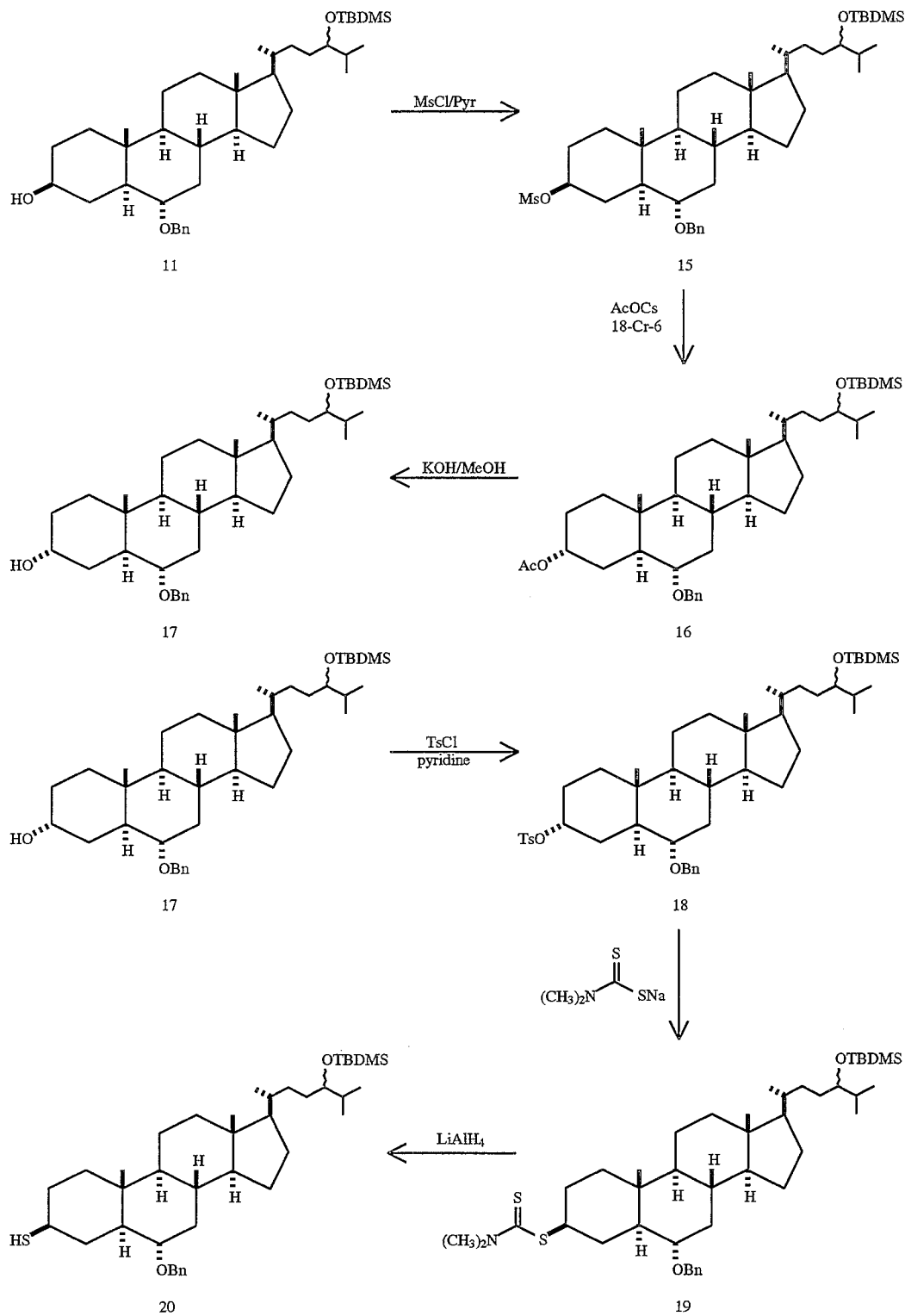

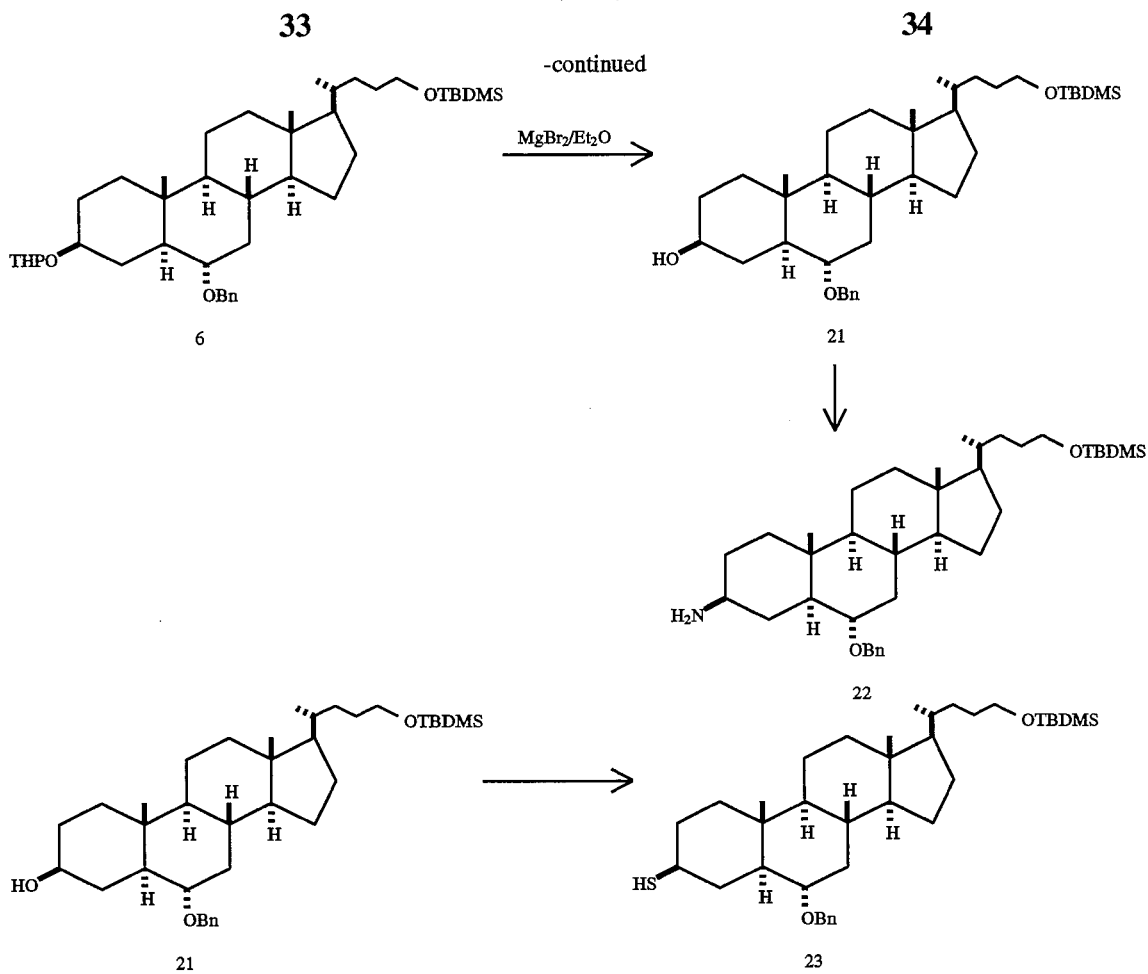

Cholenic acid 1 is treated with dihydropyran (DHP) and a catalytic amount of pyridinium p-toluenesulfonate (PPTS) (M. Miyashita, A. Yoshikoshi, P. A. Grieco, *J. Org. Chem.* 42, 1977, 3772) to give compound 2. Reduction of compound 2 with lithium aluminum hydride or similar reducing agent gives 24-alcohol 3. The 24-alcohol is then protected as the t-butyldimethylsilyl (TBDMS) ether by treatment with TBDMS chloride and imidazole (E. J. Corey, A. Venkateswarlu, *J. Am. Chem. Soc.* 94, 1972, 6190). Hydroboration-oxidation of compound 4 results in formation of 6α-alcohol 5 with the desired trans A-B ring junction (S. Wolfe, M. Nussim, Y. Mazur, F. Sondheimer, *J. Org. Chem.* 24, 1959, 1034; K. Burgess, J. Cassidy, M. J. Ohlmeyer, *J. Org. Chem.* 56, 1991, 1020). The 6α-alcohol is then protected as the benzyl ether by treatment with benzyl bromide (BnBr) and sodium hydride (J. D. White, G. N. Reddy, G. O. Spessard, *J. Am. Chem. Soc.* 110, 1988, 1624) to give compound 6. The TBDMS protecting group is then removed by treatment with tetra-n-butylammonium fluoride to give compound 7 (E. J. Corey, A. Venkateswarlu, *J. Am. Chem. Soc.* 94, 1972, 6190). Oxidation of the resultant 24-alcohol with Collin's reagent (CrO₃·2Pyr) gives aldehyde 8. Treatment of this aldehyde with isopropylmagnesium bromide followed by quenching with water gives alcohol 9. The resultant 24-alcohol is then protected as the TBDMS ether to give compound 10 as described above for the protection of compound 3. The 3β-tetrahydropyranyl (THP) protecting group is then selectively removed by treatment with magnesium bromide in ether to give 3β-alcohol 11 (S. Kim, J. H. Park, *Tetrahedron Lett.* 28, 1987, 439). Oxidation with Collin's reagent followed by treatment with benzyloxyamine hydrochloride and pyridine gives oxime 13. Reduction with lithium aluminum hydride gives 3β-amine 14.

The 3β-alcohol of compound 11 is inverted by the method described by Adam et al. (P. Adam, J. -C. Schmid, P. Albrecht, *Tetrahedron Lett.* 32, 1991, 2955) to give 3α-alcohol 17. This is accomplished by treatment with mesyl chloride in pyridine to give compound 15, displacement with cesium acetate to give compound 16, and hydrolysis with methanolic potassium hydroxide. Treatment of 3α-alcohol 17 with p-toluenesulfonyl chloride in pyridine gives tosylate 18. Displacement of the tosylate is mediated by treatment with sodium N,N-dimethyldithiocarbamate to give compound 19, which is reduced with lithium aluminum hydride to give compound 20 (J. L. Wardell, "The Chemistry of the Thiol Group," S. Patai (ed.), John Wiley and Sons, New York, 1974, 519).

Selective deprotection of the 3β-THP of compound 6 with magnesium bromide gives compound 21 (S. Kim, J. H. Park, *Tetrahedron Lett.* 28, 1987, 439). The resultant 3β-alcohol is converted to 3β-amine 22 in a manner analogous to the conversion of compound 11 to compound 14.

Compound 21 is converted to the corresponding 3β-thiol 23 in a manner analogous to the conversion of compound 11 to compound 20.

EXAMPLE A(2)
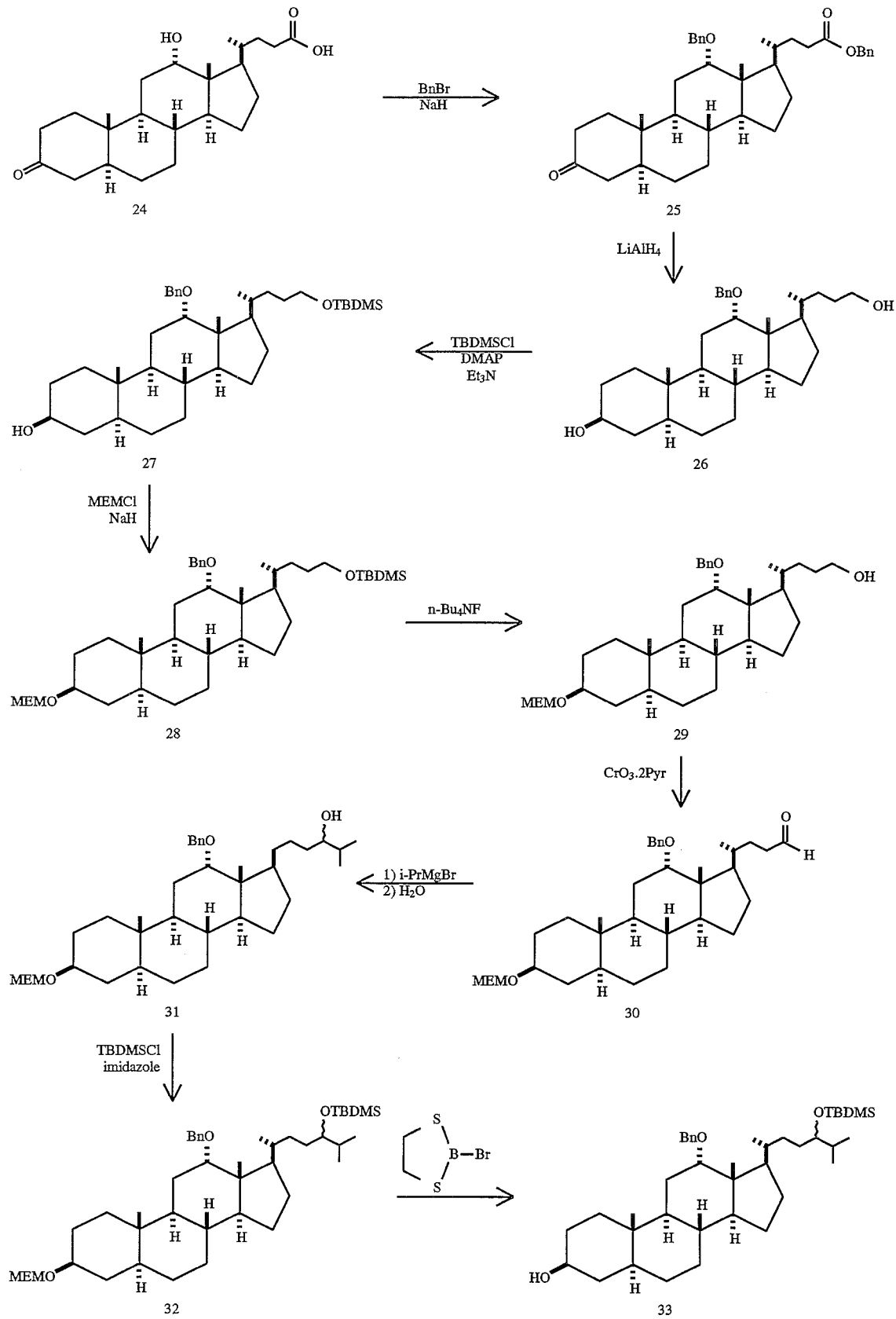

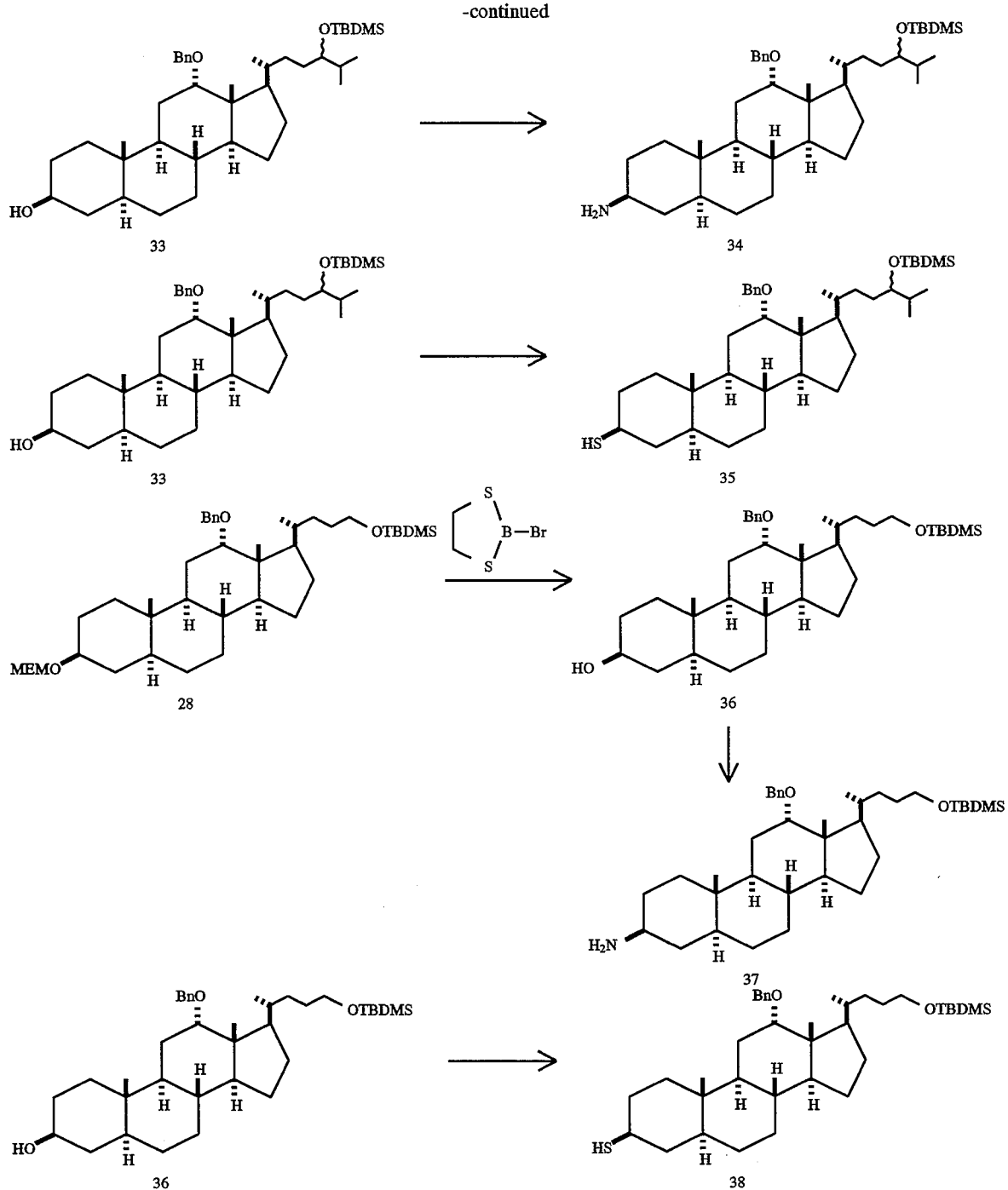

Treatment of known cholenic acid derivative 24 (M. N. Iqbal, W. H. Elliot, *Steroids* 53, 1989, 413) with benzyl bromide and sodium hydride gives compound 25 (J. D. White, G. N. Reddy, G. O. Spessard, *J. Am. Chem. Soc.* 110, 1988, 1624). Reduction with lithium aluminum hydride gives 3β,24-diol 26. Selective protection of the primary alcohol with TBDMS chloride, dimethylaminopyridine (DMAP), and triethylamine gives compound 27 (S. K. Chaudhary, O. Hernandez, *Tetrahedron Lett.*, 1979, 99). The secondary 3β-alcohol of compound 27 is then protected as the 2-methoxyethoxymethyl (MEM) ether by treatment with MEM chloride and NaH (E. J. Corey, J. -L. Gras, P. Ulrich, *Tetrahedron Lett.*, 1976, 809) to give compound 28.

Removal of the TBDMS ether with tetra-n-butylammonium fluoride (E. J. Corey, A. Venkateswarlu, *J. Am. Chem. Soc.* 94, 1972, 6190) (giving compound 29), oxidation with Collin's reagent (giving compound 30), and treatment with isopropylmagnesium bromide gives compound 31. Protection of the 24-alcohol with TBDMS chloride yields compound 32 (E. J. Corey, A. Venkateswarlu, *J. Am. Chem. Soc.* 94, 1972, 6190). Selective removal of the MEM protecting group of the 3β-alcohol gives compound 33 (D. R. Williams, S. Sakdarat, *Tetrahedron Lett.* 24, 1983, 3965).

3β-Alcohol 33 is converted to the corresponding 3β-amine 34 in a manner analogous to the conversion of compound 11 to compound 14. 3β-Alcohol 33 is converted to the corresponding 3β-thiol 35 in a manner analogous to the conversion of compound 11 to compound 20.

The MEM protecting group of the 3β-alcohol of compound 28 is selectively removed to give compound 36 (D. R. Williams, S. Sakdarat, *Tetrahedron Lett.* 24, 1983, 3965). 3β-Alcohol 36 is converted to 3β-amine 37 in a manner analogous to the conversion of compound 11 to compound 14. Compound 36 is converted the corresponding 3β-thiol, compound 38, in a manner analogous to the conversion of compound 11 to compound 20.

EXAMPLE A(3)

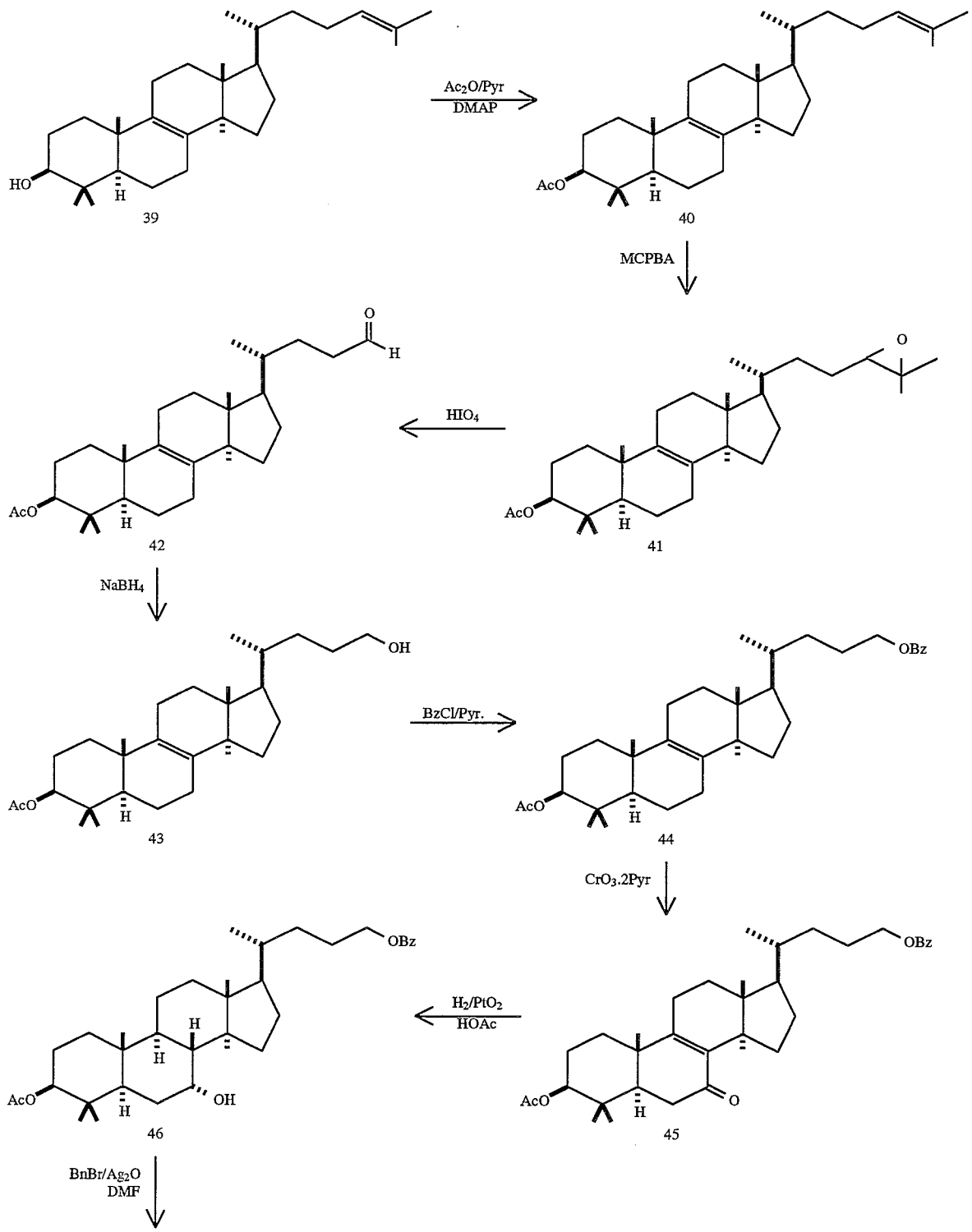

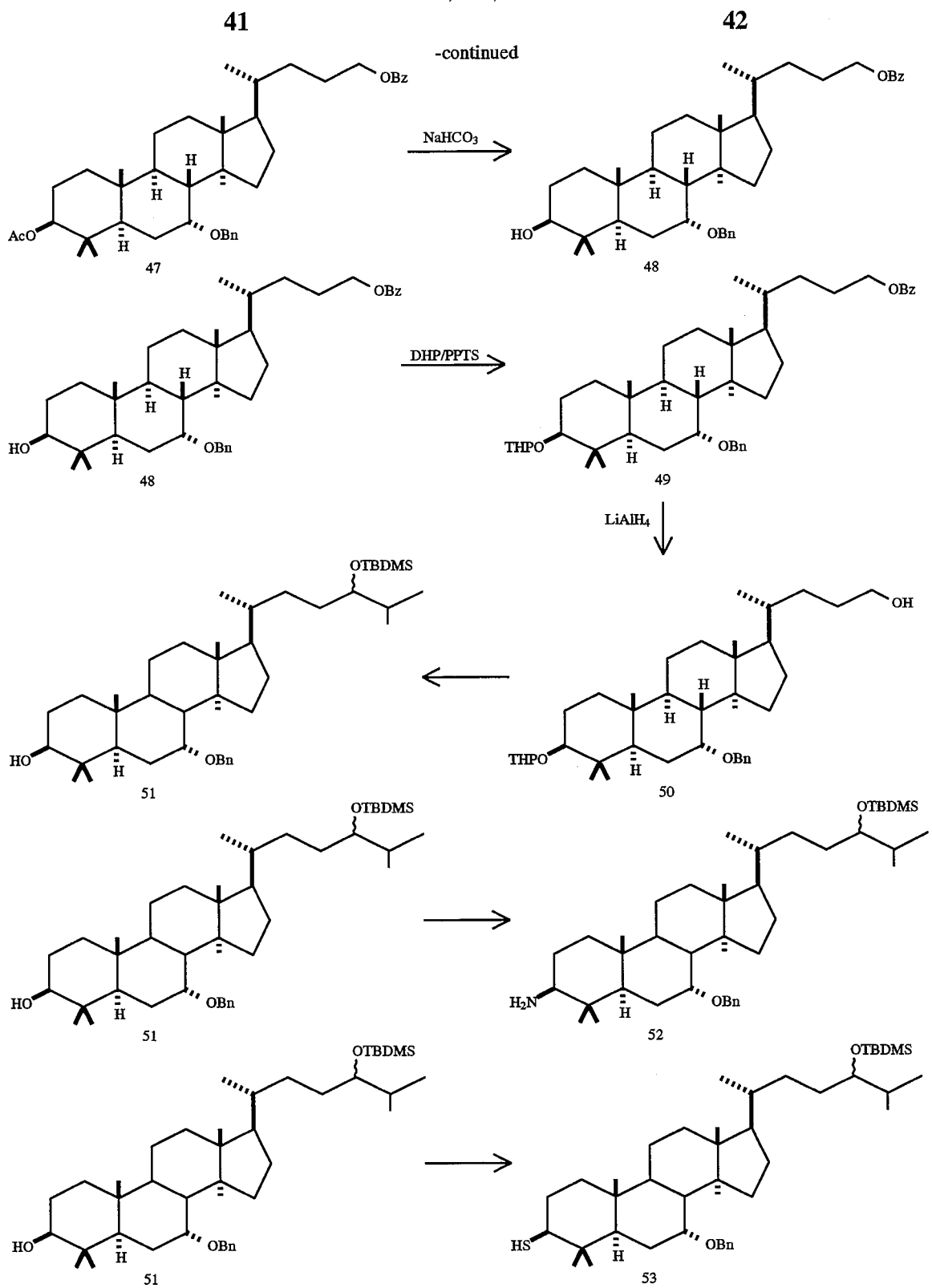

Lanosterol 39 is acetylated by treatment with acetic anhydride, pyridine, and a catalytic amount of DMAP to give compound 40. The 24-double bond is selectively epoxidized by treatment with m-chloroperoxybenzoic acid (MCPBA) as described by Sato and Sonoda (Y. Sato, Y. Sonoda, *Chem. Pharm. Bull.* 29, 1987, 356). The epoxide 41 is oxidatively cleaved by treatment with periodic acid to give aldehyde 42 (J. P. Nagarkatti, K. R. Ashley, *Tetrahedron Lett.*, 1973, 4599). Reduction of 24-aldehyde 42 with sodium borohydride or other appropriate reducing agent gives alcohol 43. Treatment with benzoyl chloride and pyridine gives compound 44. Treatment of compound 44 with Collin's reagent results in allylic oxidation product 45 (W. G. Salmond, M. A. Barta, J. L. Havens, *J. Org. Chem.*

43, 1978, 2057). Reduction of the double bond, epimerization, followed by reduction of the ketone is accomplished by treatment of compound 45 with hydrogen in acetic acid with a catalytic amount of Adam's catalyst (PtO$_2$) (Y. Sonoda, Y. Tanoue, M. Yamaguchi, Y. Sato, *Chem. Pharm. Bull.* 35, 1987, 394) to give compound 46. Protection of the 7α-alcohol as the benzyl ether with benzyl bromide and silver oxide gives compound 47 (L. Van Hijfte, R. D. Little, *J. Org. Chem.* 50, 1985, 3940). The acetate at C-3 of compound 47 is then removed by treatment with sodium bicarbonate. The resultant alcohol 48 is then protected as the THP ether to give compound 49 (M. Miyashita, A. Yoshikoshi, P. A. Grieco, *J. Org. Chem.* 42, 1977, 3772).

The benzoate protecting group of the 24-alcohol is removed with lithium aluminum hydride to give compound 50. Compound 50 is then converted to compound 51 in a manner analogous to the conversion of compound 7 to compound 11.

3β-Alcohol 51 is converted to 3β-amine 52 in a manner analogous to the conversion of compound 11 to compound 14.

3β-Alcohol 51 is converted to 3β-thiol 53 in a manner analogous to the conversion of compound 11 to compound 20.

EXAMPLE A(4)

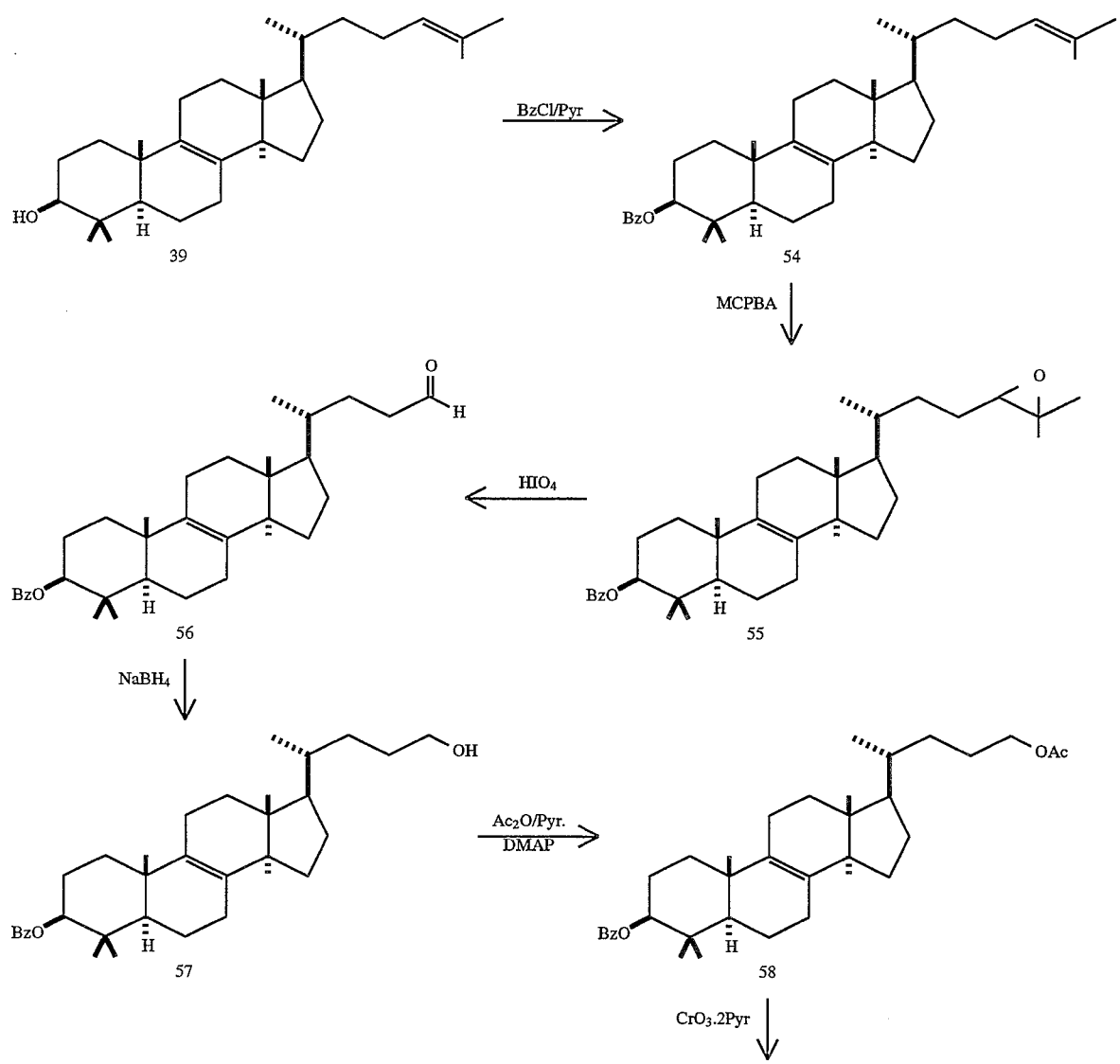

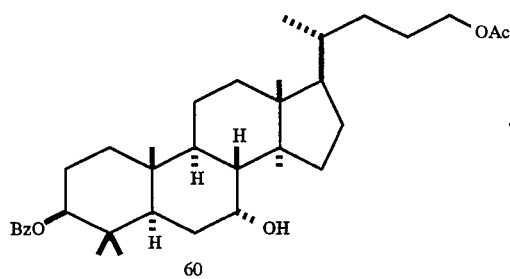
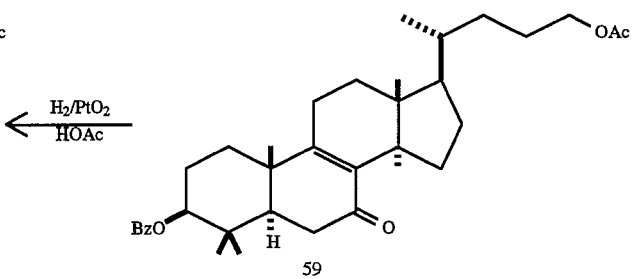
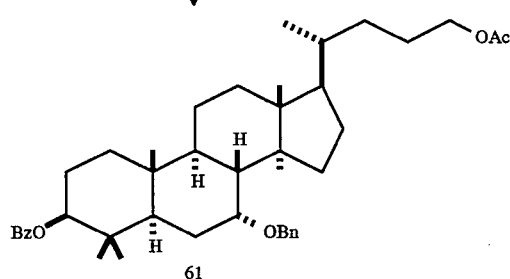
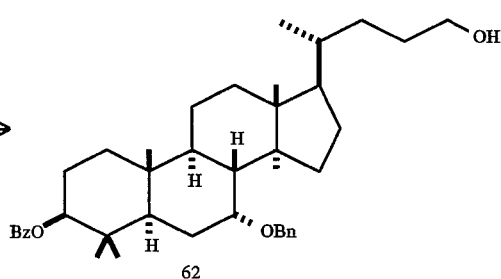
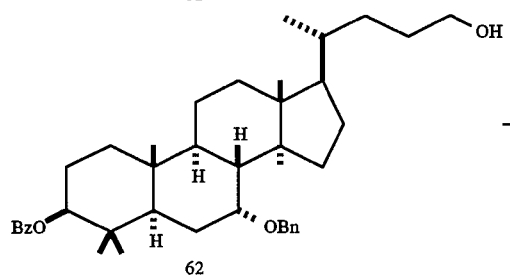
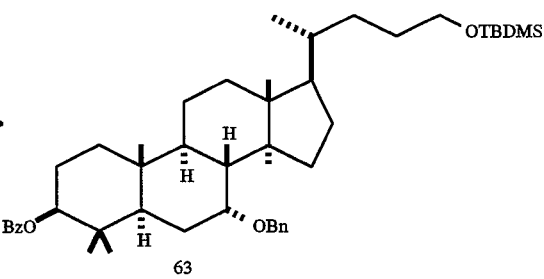
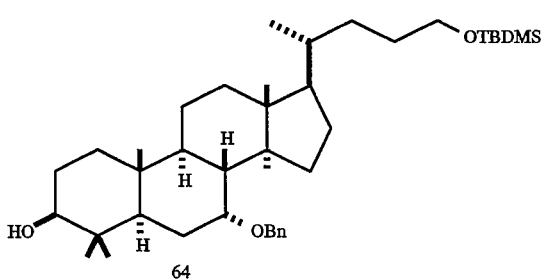
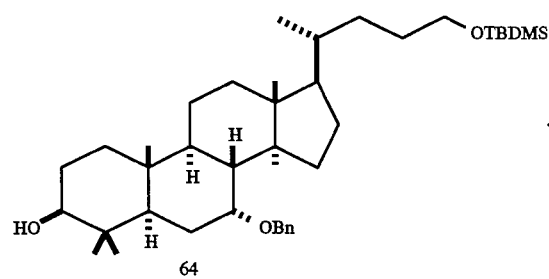
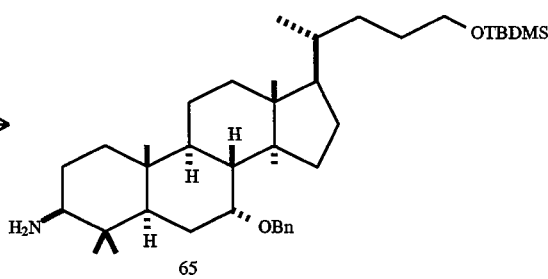

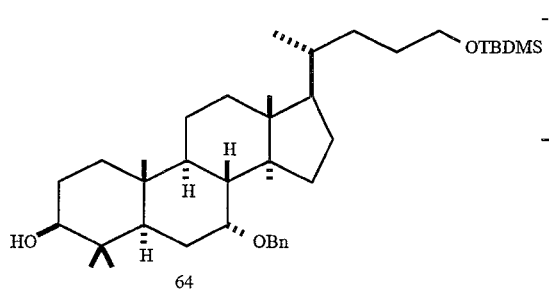

47

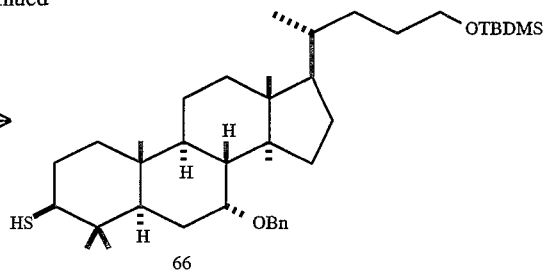

48

-continued

Lanosterol 39 is treated with benzoyl chloride/pyridine to give compound 54, MCPBA to give compound 55, and periodic acid to give aldehyde 56 in a manner similar to the conversion of compound 39 to compound 42. Reduction with sodium borohydride gives compound 57. The resultant alcohol 57 is protected as the corresponding acetate 58. Allylic oxidation (giving compound 59) followed by reduction gives compound 60. The resultant 7α-alcohol is protected as the benzyl ether by treatment with benzyl bromide and silver oxide in DMF (L. Van Hijfte, R. D. Little, *J. Org. Chem.* 50, 1985, 3940) to give compound 61. The acetate is removed by treatment with sodium bicarbonate and the resultant alcohol 62 is protected as the TBDMS ether by treatment with TBDMS chloride and imidazole, giving compound 63. 3β-Alcohol 64 is obtained by reductive removal of the benzoate by treatment with lithium aluminum hydride.

Compound 64 is converted to 3β-amino compound 65 in a manner analogous to the conversion of compound 11 to compound 14.

Compound 64 is converted to the corresponding 3β-thiol, compound 66, in a manner analogous to the conversion of compound 11 to compound 20.

EXAMPLE A(5)

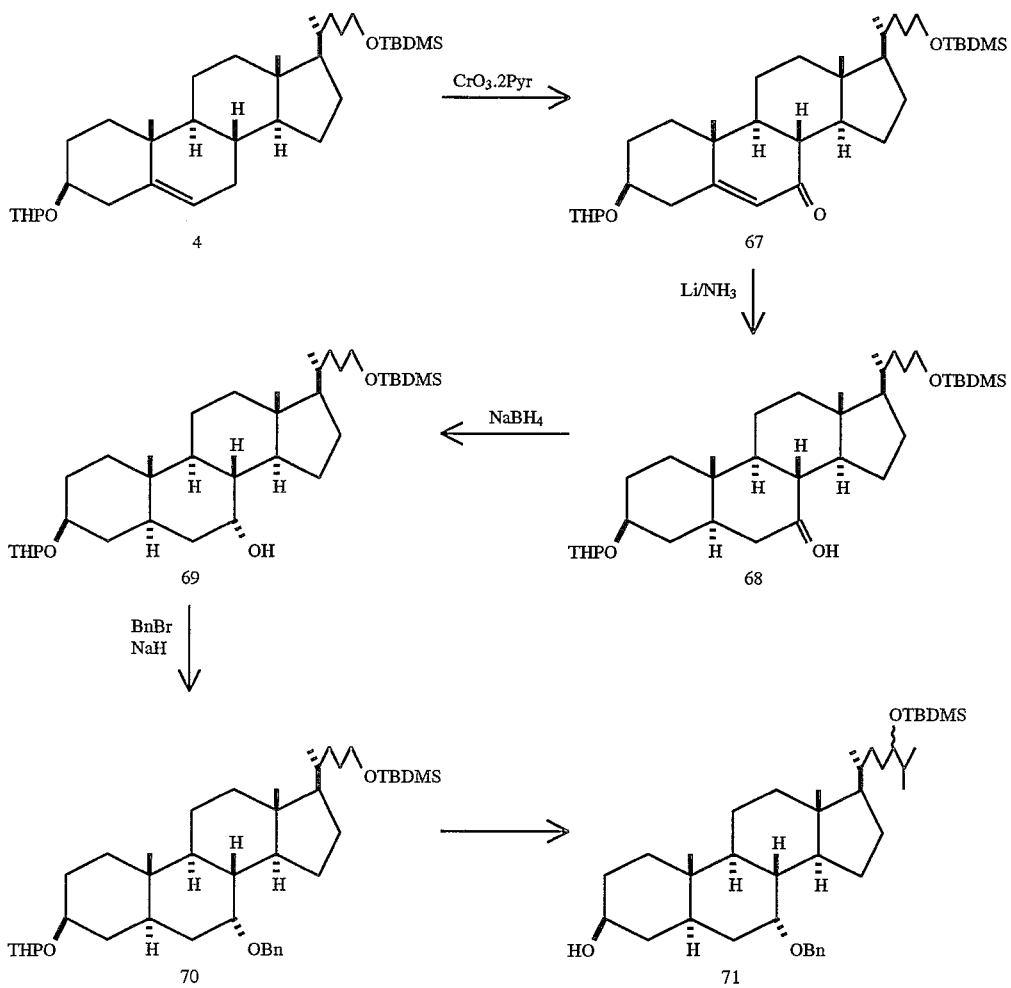

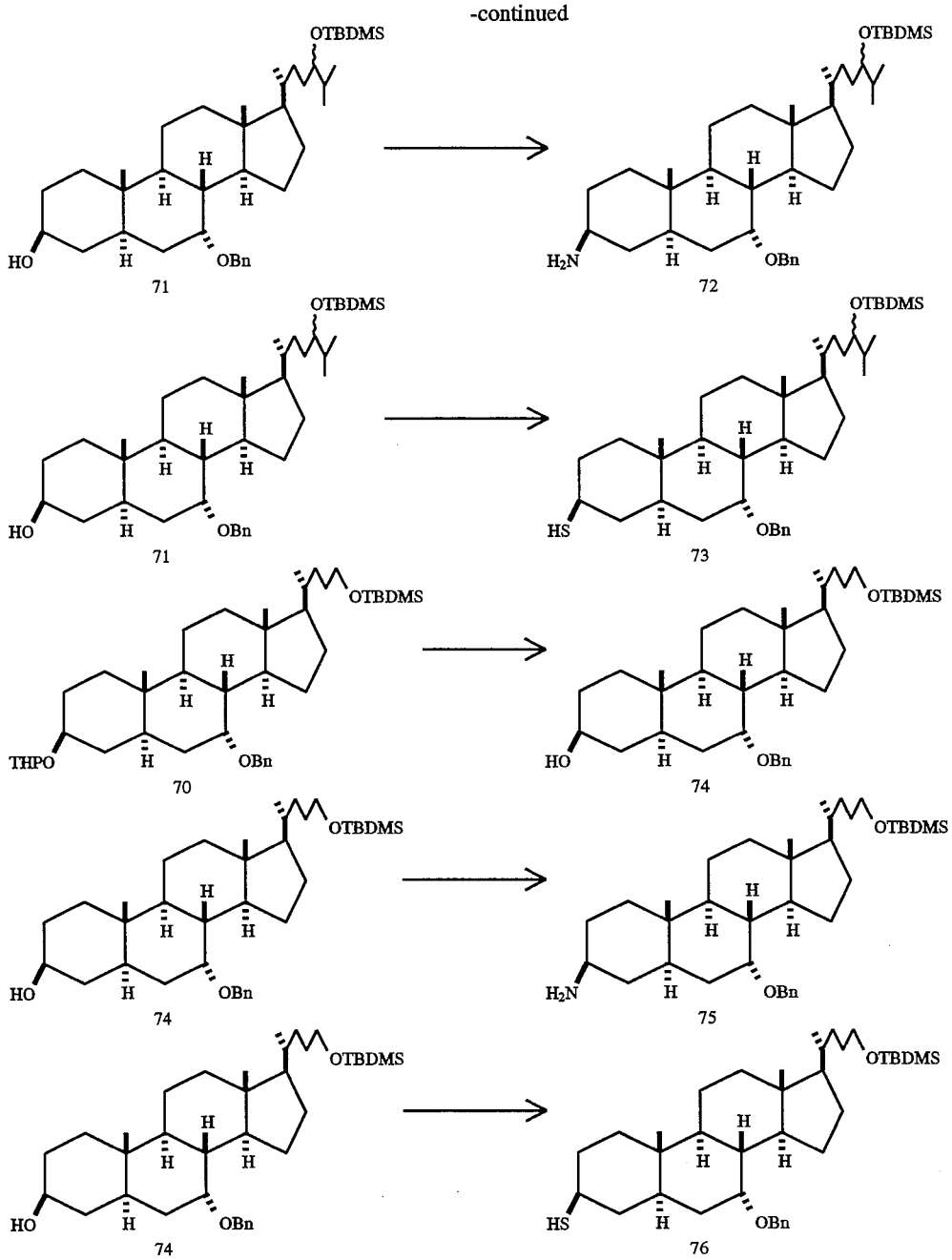

Allylic oxidation of compound 4 with Collin's reagent (W. G. Salmond, M. A. Barta, J. L. Havens, *J. Org. Chem.* 43, 1978, 2057) gives enone 67. Reduction of the resultant enone with lithium in ammonia (H. L. Dryden, Jr., "Organic Reactions in Steroid Chemistry," vol. 1, J. Fried and J. A. Edwards (eds.), Van Norstrand Reinhold Co., New York, 1972, 27–31) results in formation of ketone 68. Reduction of compound 68 with sodium borohydride followed by protection of the resultant alcohol 69 as the benzyl ether gives compound 70. Compound 70 is converted to compound 71 in a manner analogous to the conversion of compound 6 to compound 11. 3β-Alcohol 71 is transformed into the corresponding 3β-amine 72 in a manner analogous to the conversion of compound 11 to compound 14. 3β-Thiol 73 is prepared from compound 71 in a manner analogous to the conversion of compound 11 to compound 20.

Selective removal of the THP protecting group of compound 70 to give compound 74 is accomplished by treatment with magnesium bromide in ether (S. Kim, J. H. Park, *Tetrahedron Lett.* 28, 1987, 439). Compound 74 is converted to the corresponding 3β-amine 75 in a manner analogous to the conversion of compound 11 to compound 14. Compound 74 is converted to compound 76 in a manner analogous to the conversion of compound 11 to compound 20.

EXAMPLE A(6)
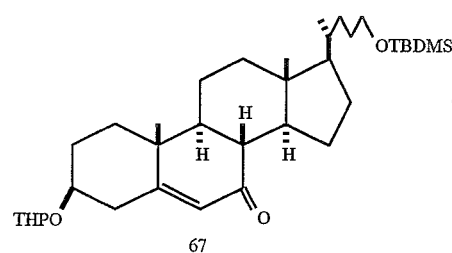
67
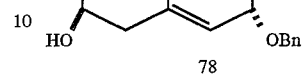
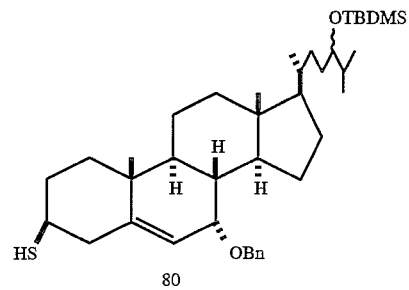
78
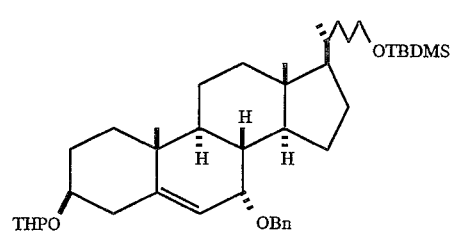
77
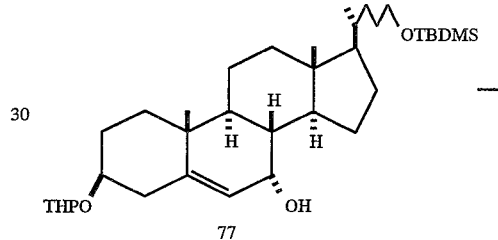
80
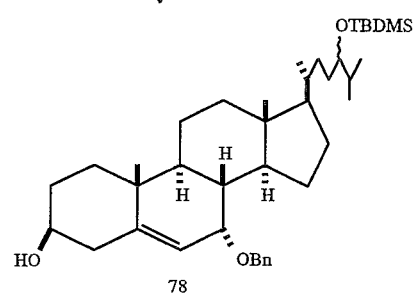
78
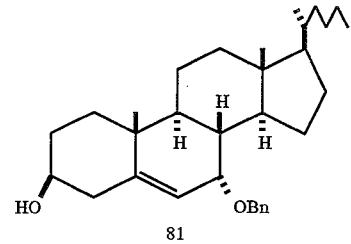
77
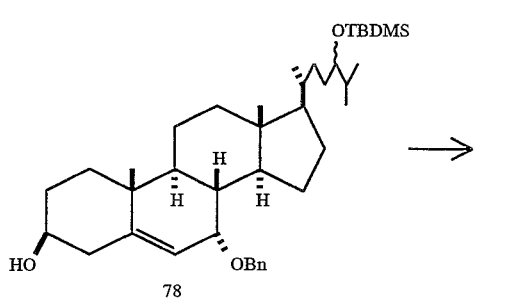
78
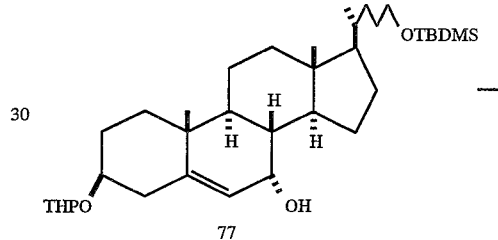
81
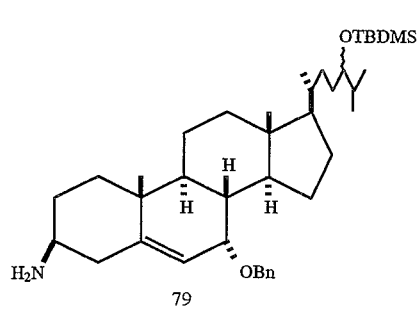
79
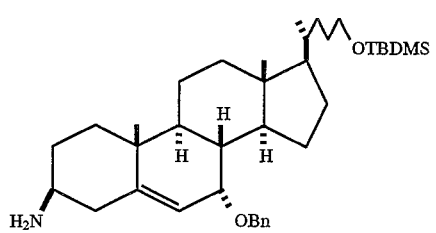
82

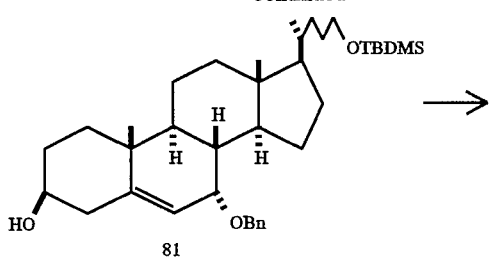

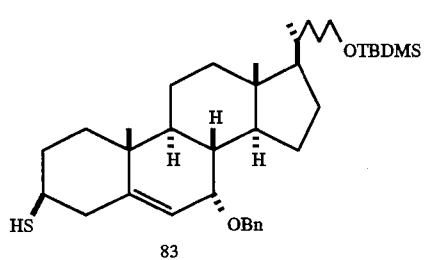

Enone 67 is reduced with sodium borohydride to give allylic alcohol 77. Compound 77 is then converted to compound 78 in a manner analogous to the conversion of compound 5 to compound 11. Compound 78 is converted to compound 79 in a manner analogous to the conversion of compound 11 to compound 14. 3β-Alcohol 78 is converted to 3β-thiol 80 in a manner analogous to the conversion of compound 11 to compound 20.

Protection of allylic alcohol 77 with benzyl bromide and sodium hydride followed by removal of the THP protecting group at C-3 by treatment with magnesium bromide (S. Kim, J. H. Park, *Tetrahedron Lett.* 28, 1987, 439) gives compound 81. Conversion of 3β-alcohol 81 to the corresponding 3β-amine, compound 82, is accomplished in a manner analogous to the conversion of compound 11 to compound 14. Compound 81 is converted to compound 83 in a manner analogous to the conversion of compound 11 to compound 20.

EXAMPLE A(7)

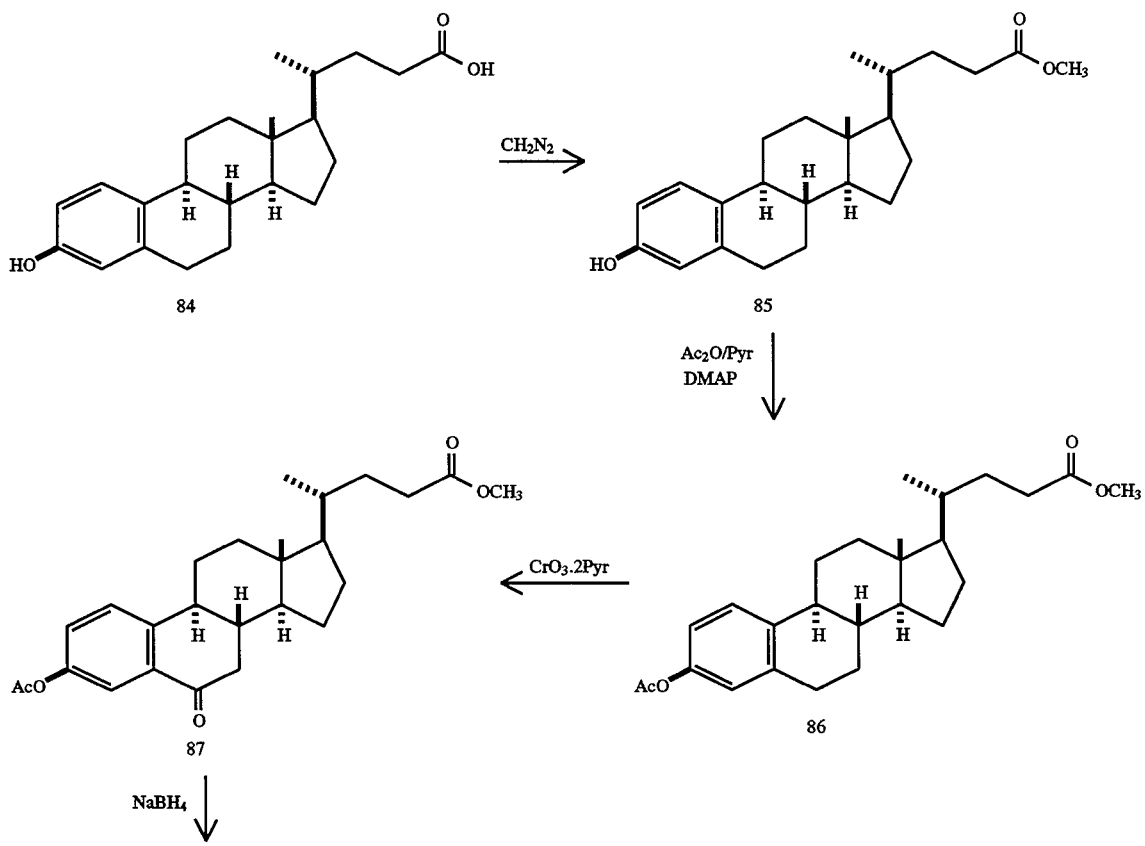

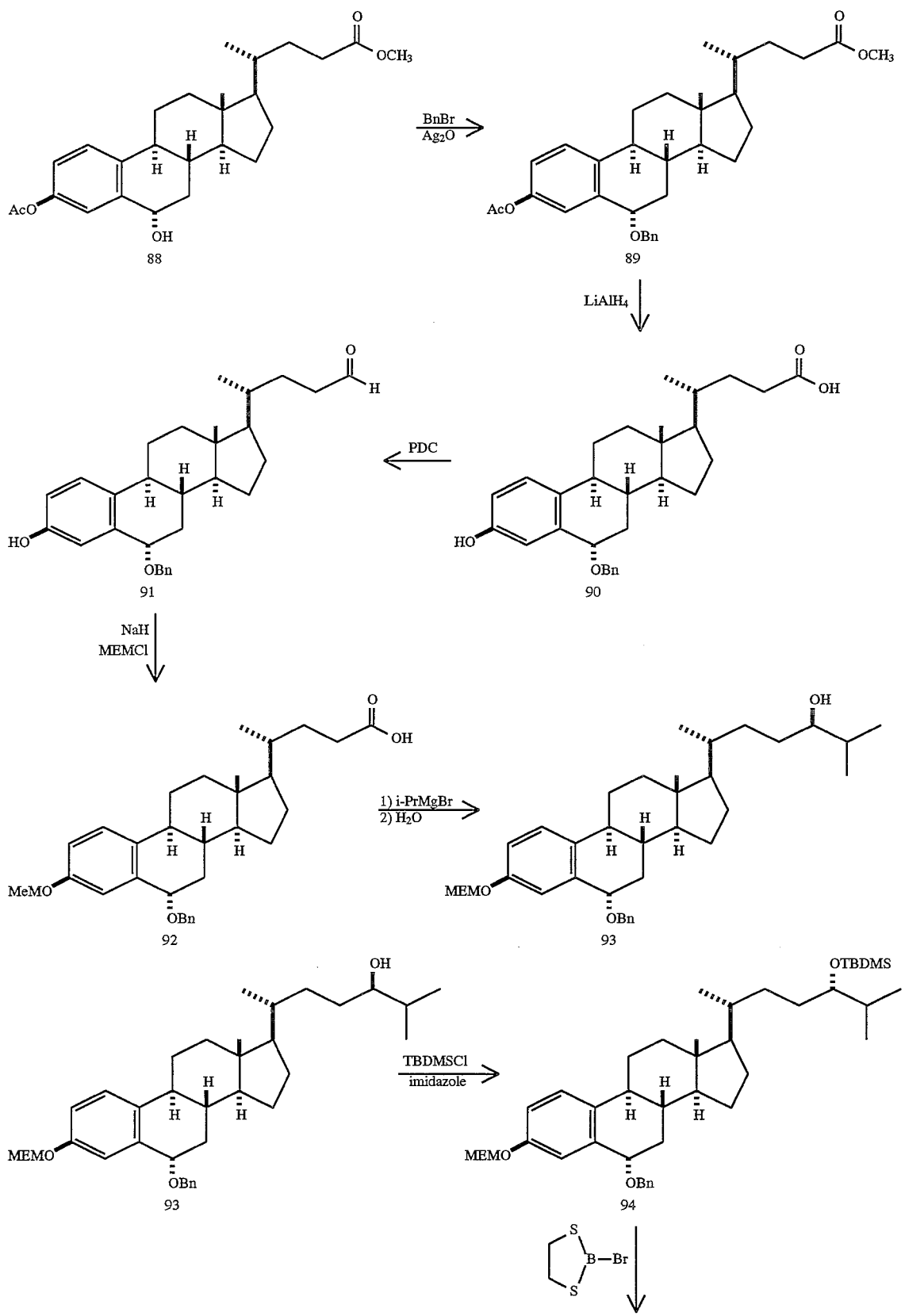

-continued

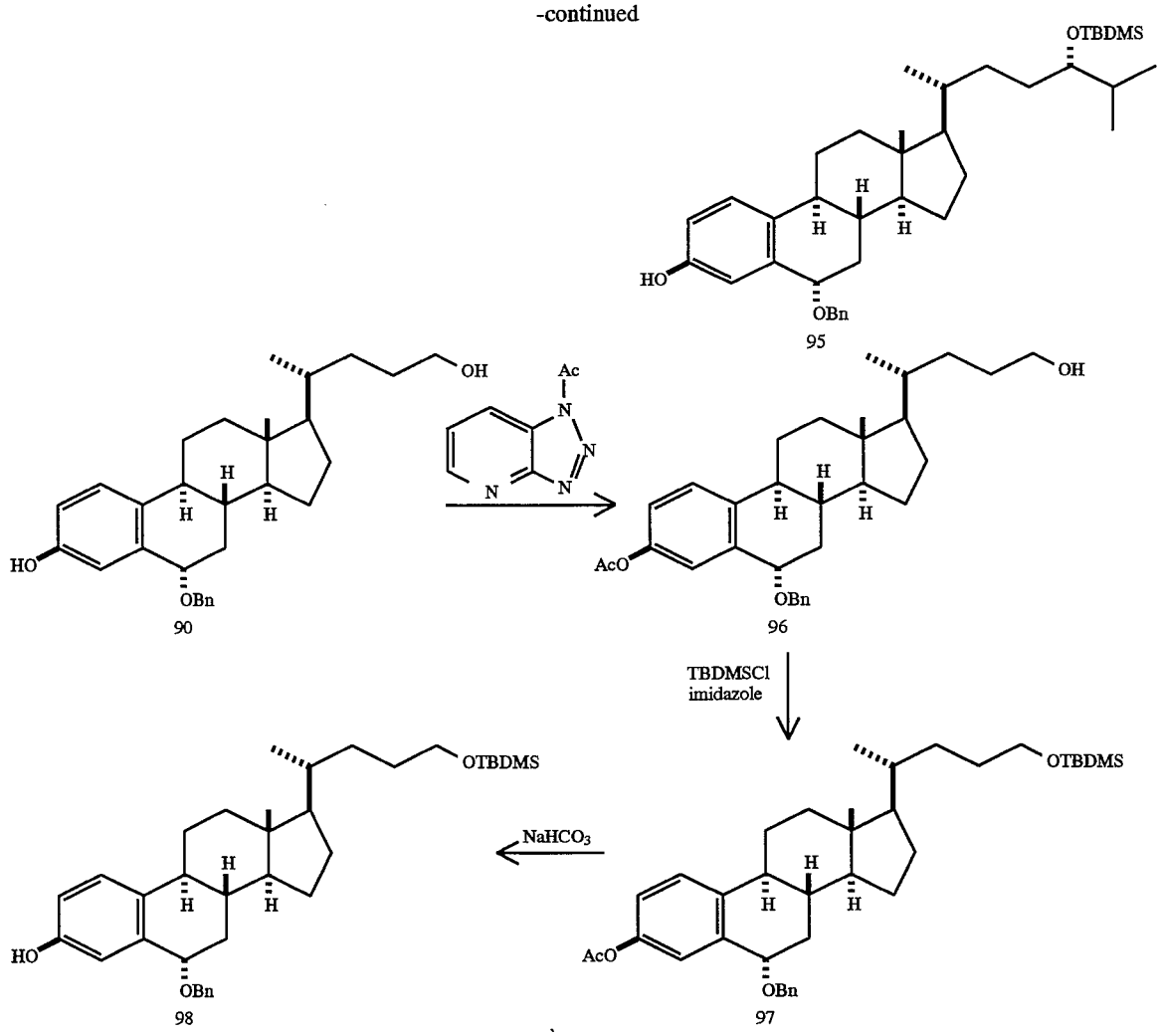

Known estrogen analog 84 (T. Namba, T. Hirota, S. Hayakawa, *J. Lipid Res.* 29, 1988, 809) is treated with diazomethane to afford methyl ester 85. The phenolic hydroxyl is then acetylated with acetic anhydride/pyridine in the presence of a catalytic amount of DMAP. Benzylic oxidation of compound 86 with Collin's reagent (G. A. Garza, P. N. Rao, *Steroids* 42, 1983, 469) gives ketone 87. Reduction of this ketone with sodium borohydride gives 7α-alcohol 88 (O. Wintersteiner, M. Moore, *J. Am. Chem. Soc.* 81, 1959, 442). Protection of the resultant alcohol as the benzyl ether (giving compound 89) followed by reduction of the esters with lithium aluminum hydride gives compound 90. Oxidation of the primary alcohol of compound 90 with pyridinium dichromate (PDC) (E. J. Corey, G. Schmidt, *Tetrahedron Lett.*, 1979, 399) gives aldehyde 91. Protection of the phenolic alcohol as MEM ether (E. J. Corey, J. -L. Gras, P. Ulrich, *Tetrahedron Lett.*, 1976, 809) (giving compound 92) followed by treatment with isopropylmagnesium bromide and subsequent hydrolysis yields compound 93. Protection of the resultant 24-alcohol as TBDMS ether (E. J. Corey, A. Venkateswarlu, *J. Am. Chem. Soc.* 94, 1972, 6190) (giving compound 94) and selective removal of the MEM protecting group (D. R. Williams, S. Sakdarat, *Tetrahedron Lett.* 24, 1983, 3965) gives compound 95.

Selective protection of the phenolic alcohol of compound 90 by treatment with 1-acetyl-v-triazolo-[4,5-b]pyridine (M. P. Paradist, G. P. Zecchini, I. Torrini, *Tetrahedron Lett.* 27, 1986, 5029) gives compound 96. The 24-alcohol of compound 96 is protected as the TBDMS ether (giving compound 97) and the acetate is removed by treatment with sodium bicarbonate to give compound 98.

EXAMPLE A(8)
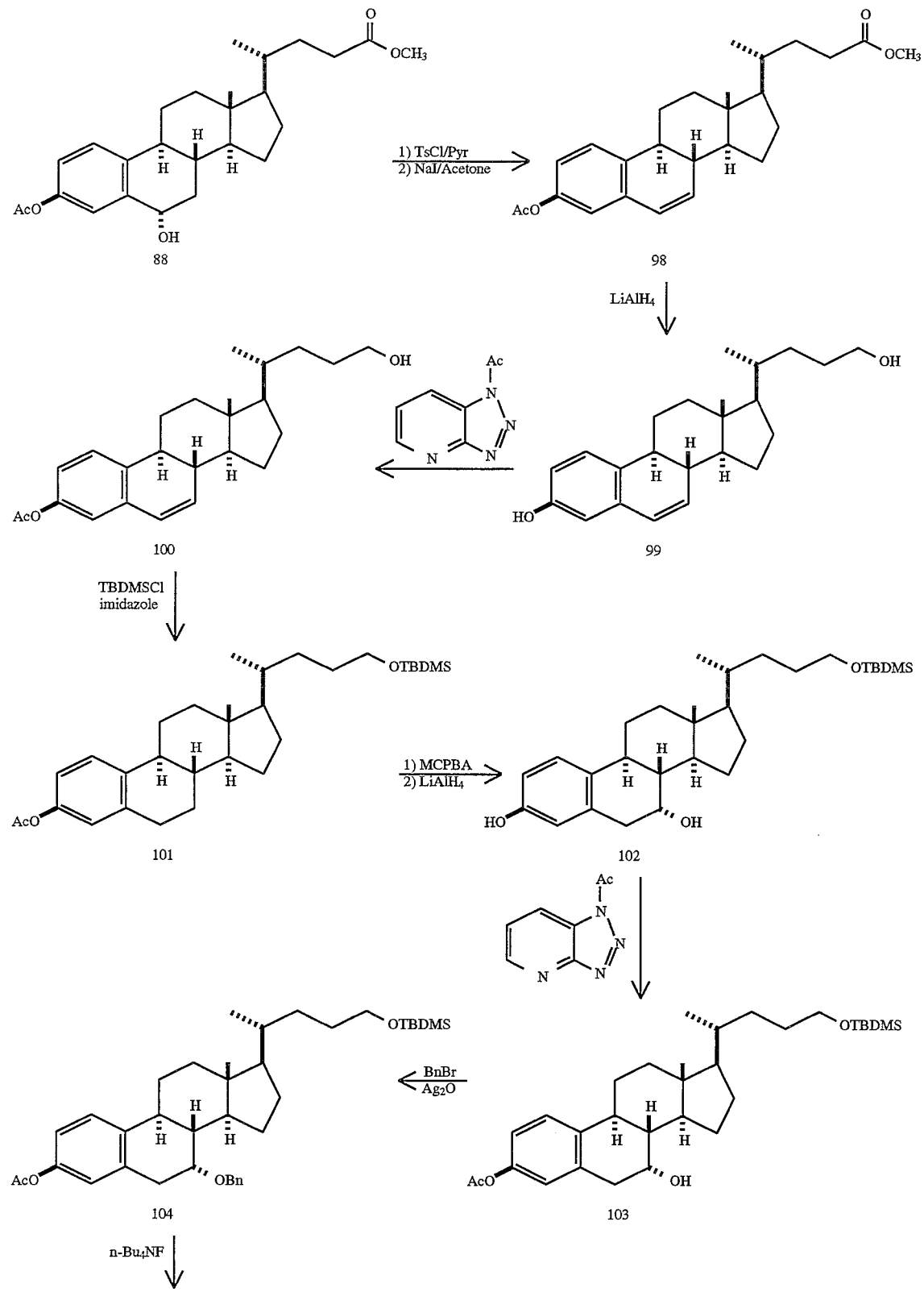

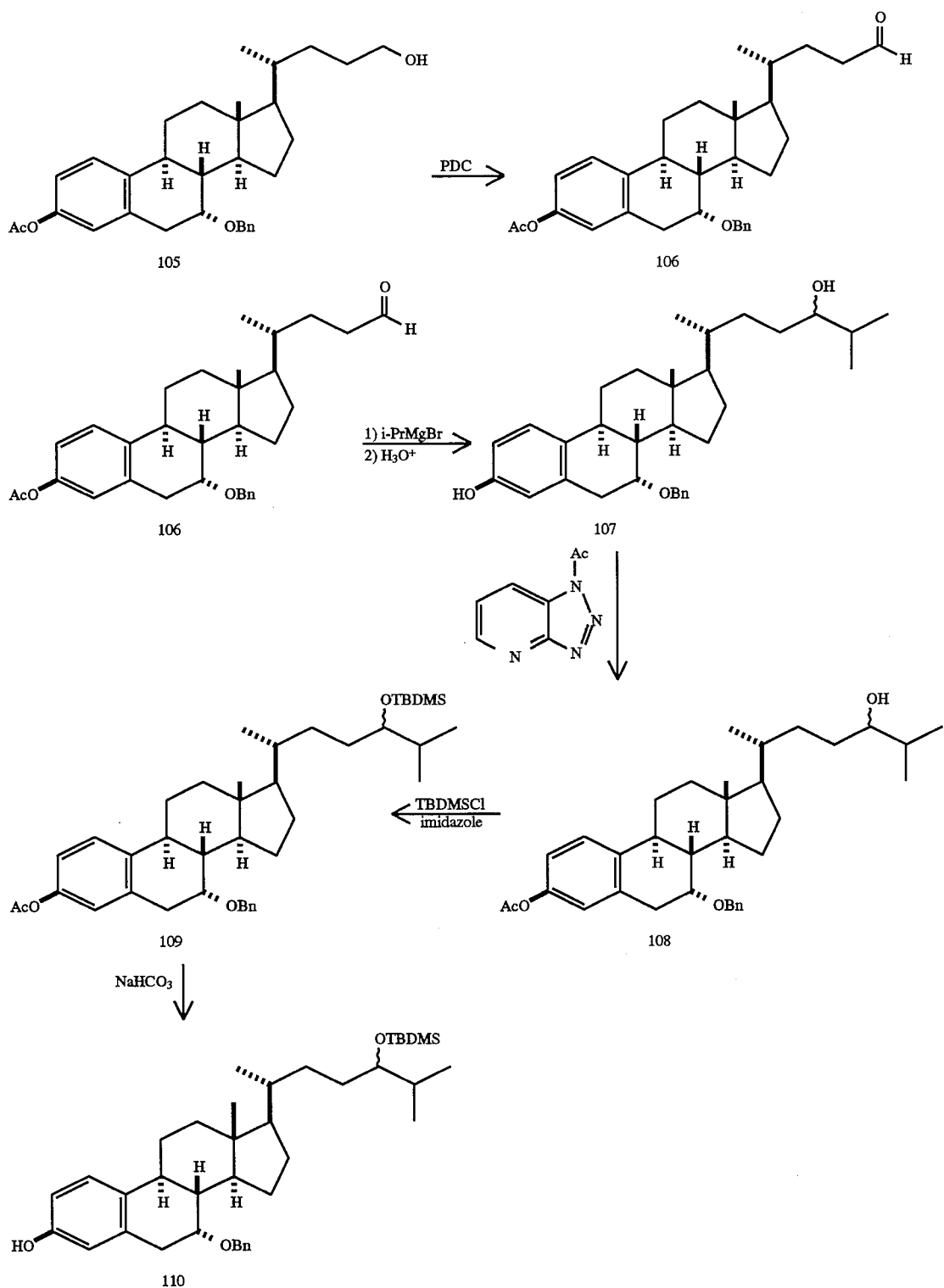

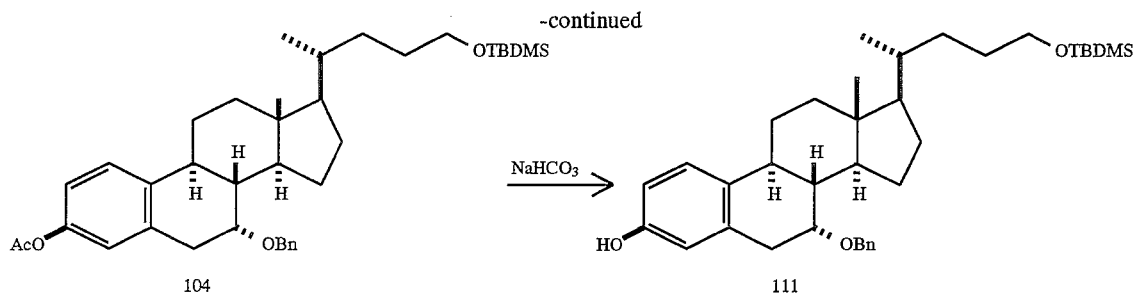

Compound 88 is treated with tosyl chloride and pyridine followed by sodium iodide in acetone to give unsaturated compound 98 (T. Arunachalam, C. Longcope, E. Caspi, *J. Org. Chem.* 254, 1979, 5900). Reduction of the esters with lithium aluminum hydride, giving compound 99, followed by selective acetylation (M. P. Paradist, G. P. Zecchini, I. Torrini, *Tetrahedron Lett.* 27, 1986, 5029) gives compound 100. The 24-alcohol is then protected as the TBDMS ether to yield compound 101. Treatment with MCPBA affords the 6α,7α-oxide, which is reduced with lithium aluminum hydride to yield 7α-alcohol 102 (J. Iriarte, H. J. Ringoid, C. Djerassi, *J. Am. Chem. Soc.* 80, 1958, 6105). The phenolic alcohol is then reprotected as the acetate (giving compound 103) and the 7α-alcohol is protected as the benzyl ether (L.

Van Hijfte, R. D. Little, *J. Org. Chem.* 50, 1985, 3940) to give compound 104. Removal of the TBDMS protecting group (giving compound 105) followed by oxidation with PDC (E. J. Corey, G. Schmidt, *Tetrahedron Lett.*, 1979, 399) gives aldehyde 106. This aldehyde is treated with isopropylmagnesium bromide to give 24-alcohol 107. Selective acetylation of the phenolic alcohol (giving compound 108), protection of the 24-alcohol as the TBDMS ether (compound 109), and removal of the phenolic acetate yields compound 110.

Compound 104 is deprotected by treatment with sodium bicarbonate to give compound 111.

EXAMPLE A(9)

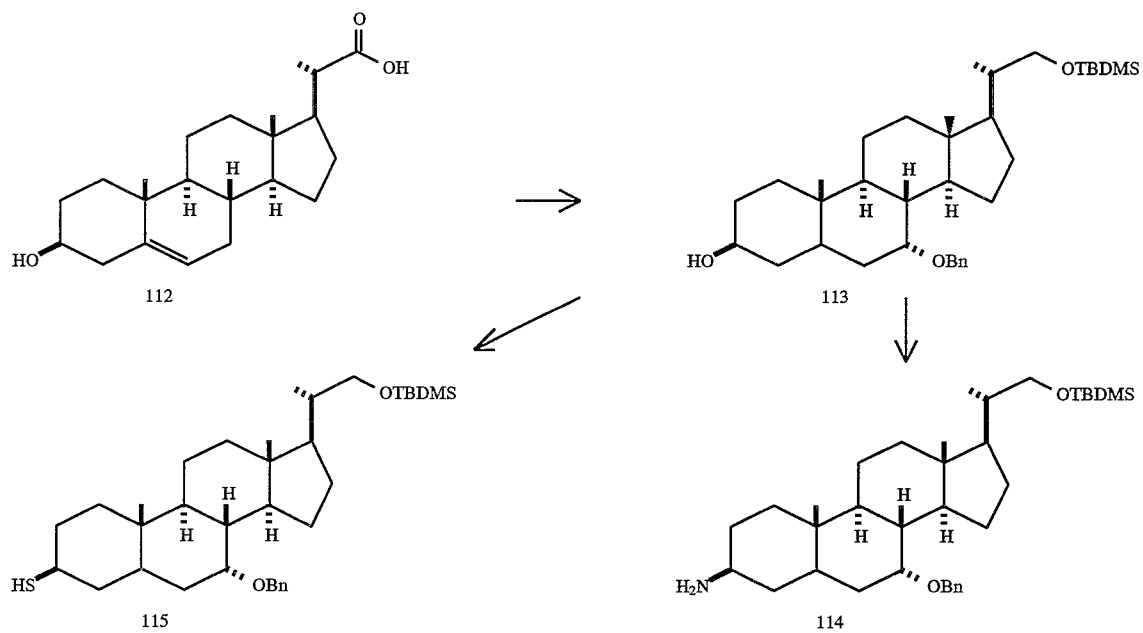

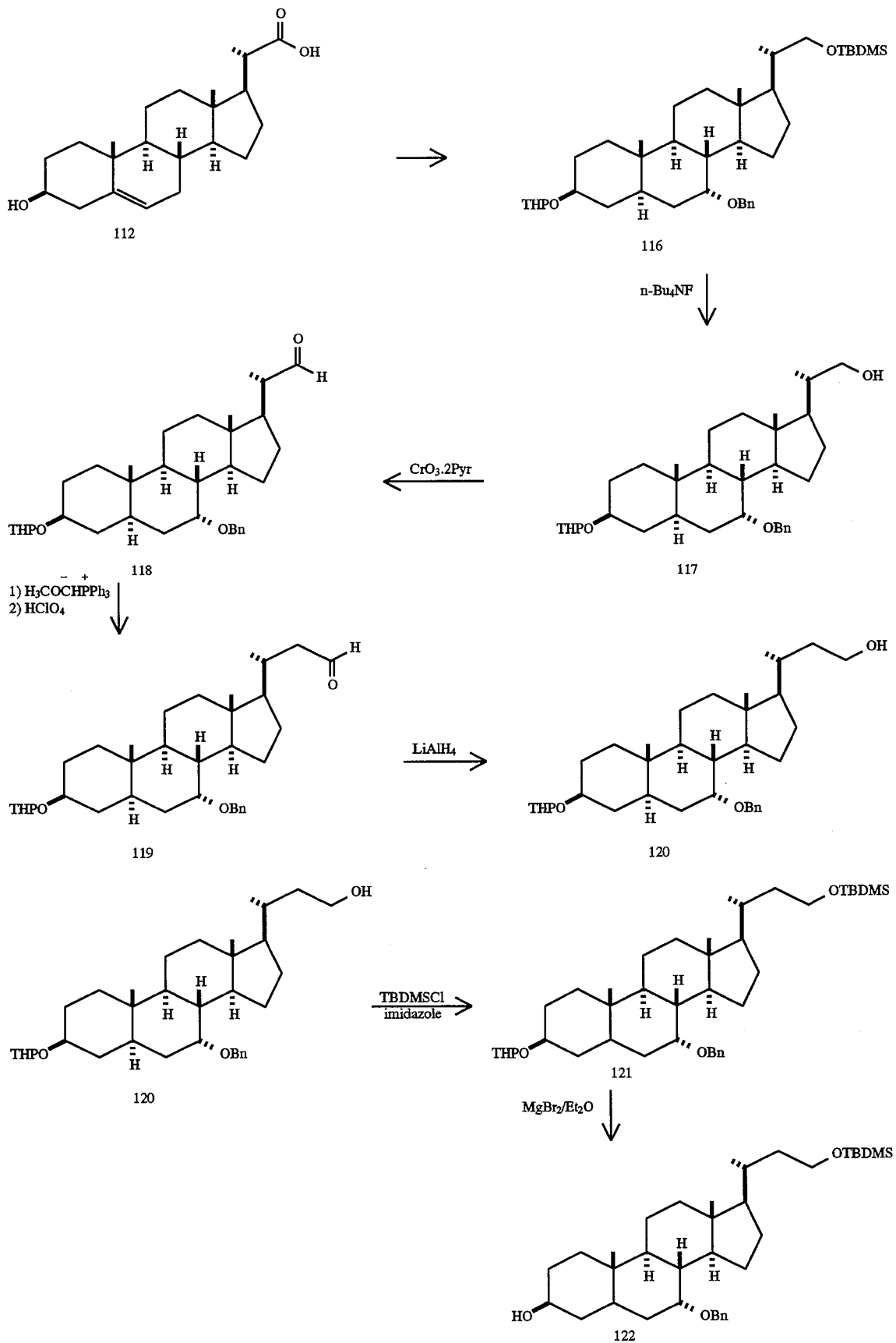

67

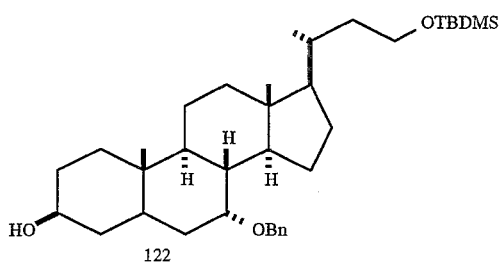
122

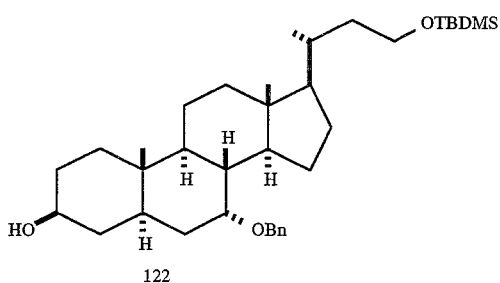
122

68

-continued

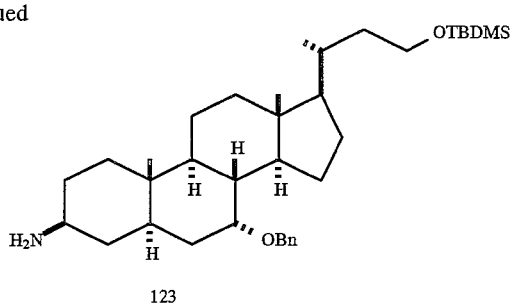
123

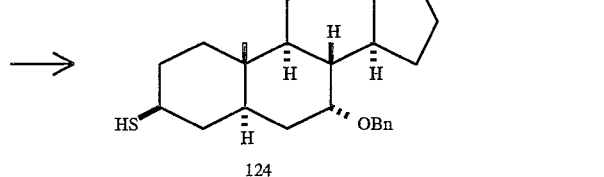
124

23,24-Bisnorcholenic acid 112 is converted to compound 113 in a manner analogous to the conversion of compound 1 to compound 4 (Example A(1)) and conversion of compound 4 to compound 71 (Example A(5)). The 3β-alcohol of compound 113 is converted to the corresponding 3β-amine, compound 114, in a manner analogous to the conversion of compound 11 to compound 14. Compound 113 is converted to compound 115 in a manner analogous to the conversion of compound 11 to compound 20.

23,24-Bisnorcholenic acid 112 is converted to compound 116 in a manner analogous to the conversion of compound 1 to compound 4 (Example A(1)) and compound 4 to compound 70 (Example A(5)). Removal of the TBDMS protecting group from the 22-alcohol of compound 116 followed by oxidation of the resultant primary alcohol 117 with Collin's reagent gives aldehyde 118. This aldehyde is then homologated by treatment with the ylide prepared from methoxymethyltriphenylphosphonium bromide followed by hydrolysis of the resultant enol ether to give compound 119 (L. L. Frye, C. H. Robinson, *J. Org. Chem.* 55, 1990, 1579). Aldehyde 119 is then reduced with lithium aluminum hydride, the resultant 23-alcohol 120 is protected as the TBDMS ether 121, and the THP protecting group at C-3 is selectively removed to give compound 122.

Compound 122 is converted to 3β-amine 123 in a manner analogous to the conversion of compound 11 to compound 14. 3β-Alcohol 122 is converted to the corresponding thiol, compound 124, in a manner analogous to the conversion of compound 11 to compound 20.

EXAMPLE A(10)

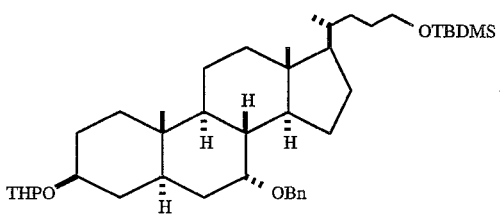
70

-continued

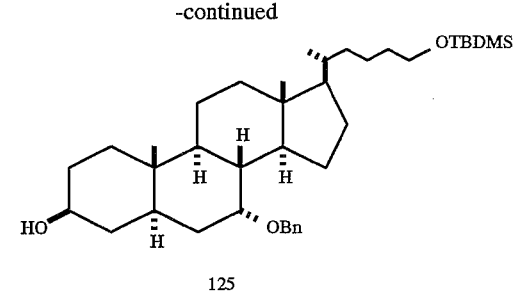
125

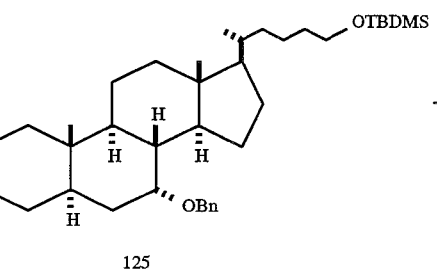
125

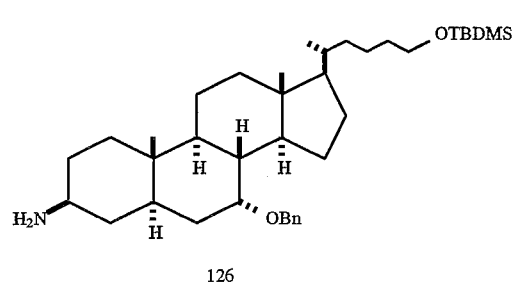
126

69
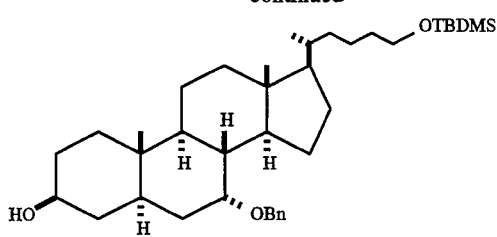
125
70
Compound 70 is converted to homologated compound 125 in a manner analogous to the conversion of compound 116 to compound 122. Compound 125 is converted to the corresponding 3β-amine, compound 126, in a manner analogous to the conversion of compound 11 to compound 14. 3β-Alcohol 125 is converted to 3β-thiol 127 in a manner analogous to the conversion of compound 11 to compound 20.
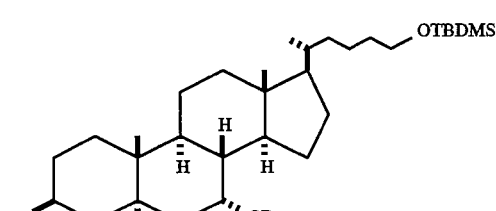
127
EXAMPLE A(11)
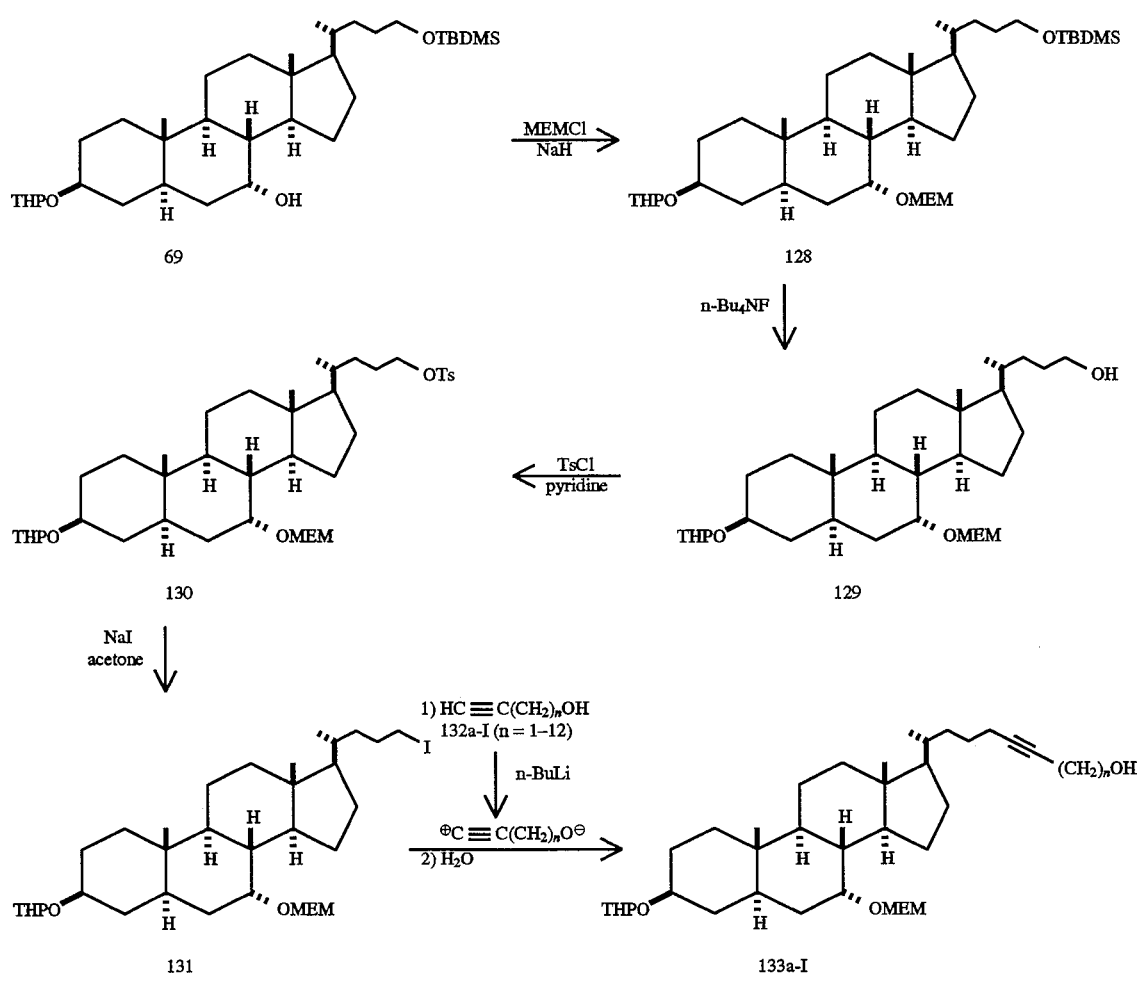

-continued
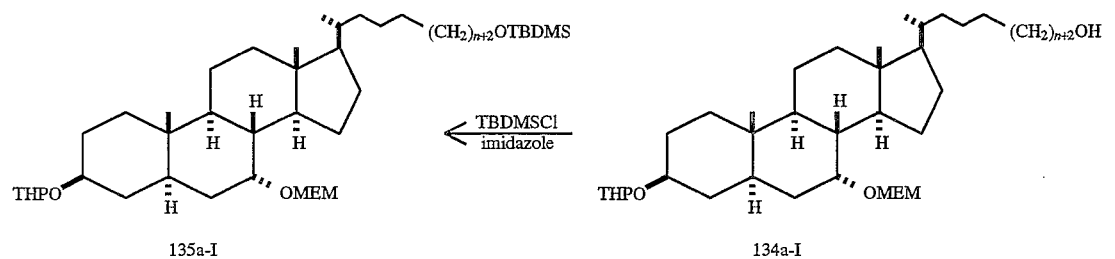
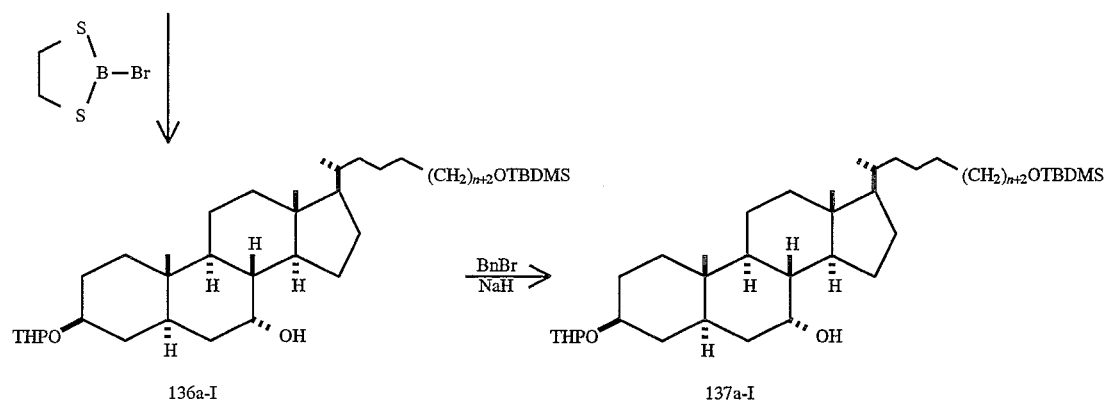
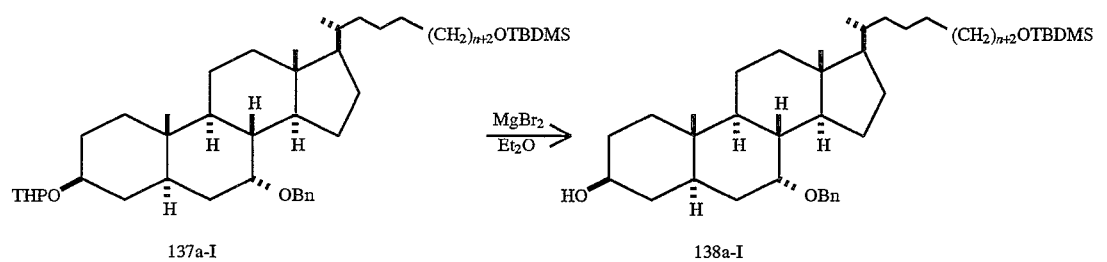
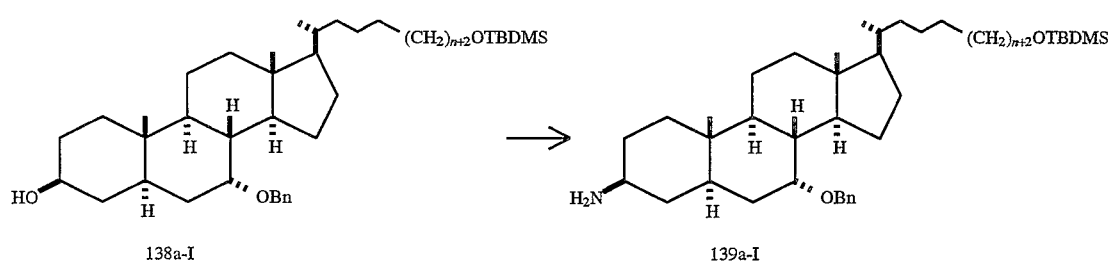
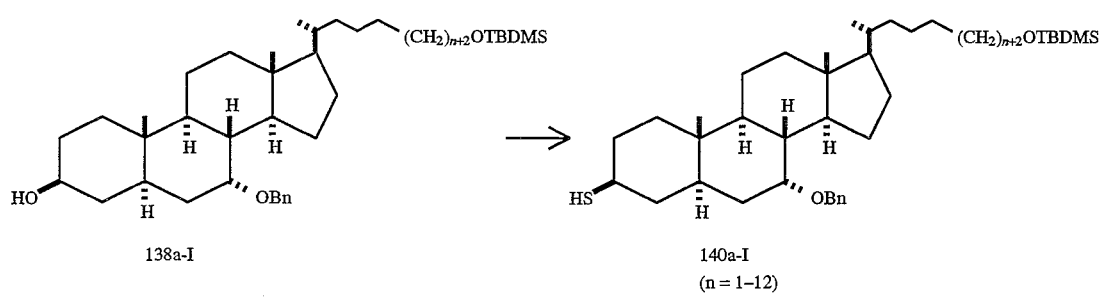

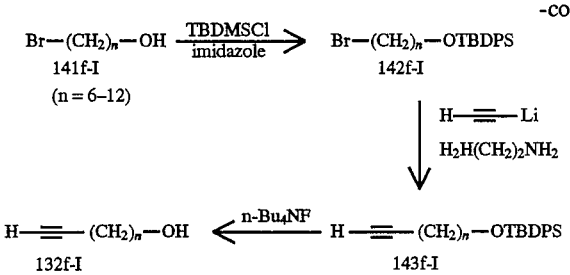

The 7α-alcohol of compound 69 is protected as the MEM ether (E. J. Corey, J. -L. Gras, P. Ulrich, *Tetrahedron Lett.*, 1976, 809) to give compound 128. The TBDMS protecting group of the 24-alcohol is removed by treatment with tetra-n-butyl-ammonium fluoride (E. J. Corey, A. Venkateswarlu, *J. Am. Chem. Soc.* 94, 1972, 6190) to yield alcohol 129. Treatment with tosyl chloride (giving compound 130) followed by sodium iodide in acetone gives compound 131. Displacement of the primary iodide of compound 131 with the dianion of a variety of acetylenic alcohols (compounds 132a-1) (S. Hahn, I. L. Stoilov, T. B. Tam Ha, D. Raederstorfff G. A. Doss, H. -T. Li, C. Djerassi, *J. Am. Chem. Soc.* 110, 1988, 8117) affords compounds 133a-1. Catalytic hydrogenation of the acetylene moieties (giving compounds 134a-1) followed by protection of the terminal alcohols as the TBDMS ethers yields compounds 135a-1. Selective removal of the MEM protecting groups (D. R. Williams, S. Sakdarat, *Tetrahedron Lett.* 24, 1983, 3965) followed by protection of the resultant 7α-alcohols 136a-1 with benzyl bromide and sodium hydride affords compounds 137a-1. The THP protecting groups of the 3α-alcohols are then removed by treatment with magnesium bromide in diethyl ether (S. Kim, J. H. Park, *Tetrahedron Lett.* 28, 1987, 439) to give compounds 138a-1. Compounds 138a-1 are converted to the corresponding 3β-amines 139a-1 in a manner analogous to the conversion of compound 11 to compound 14. Compounds 138a-1 are converted to the corresponding 3α-thiols 140a-1 in a manner analogous to the conversion of compound 11 to compound 20.

Acetylenic alcohols 132a-e (n=1-5) are commercially available. Acetylenic alcohols 132f-1 are prepared from the corresponding bromo alcohols 141f-1. The terminal alcohols of compounds 141f-1 are protected as the t-butyldiphenylsilyl (TBDPS) ethers (S. Hanessian, P. Lavallee, Can. *J. Chem.* 53, 1975, 2975) by treatment with TBDPS chloride and imidazole to give compounds 142f-1. Displacement of the bromide of these compounds with lithium acetylide/ethylene diamine yields compounds 143f-1, which are deprotected with tetra-n-butylammonium fluoride to give the acetylenic alcohols 132f-1.

EXAMPLE A(12)

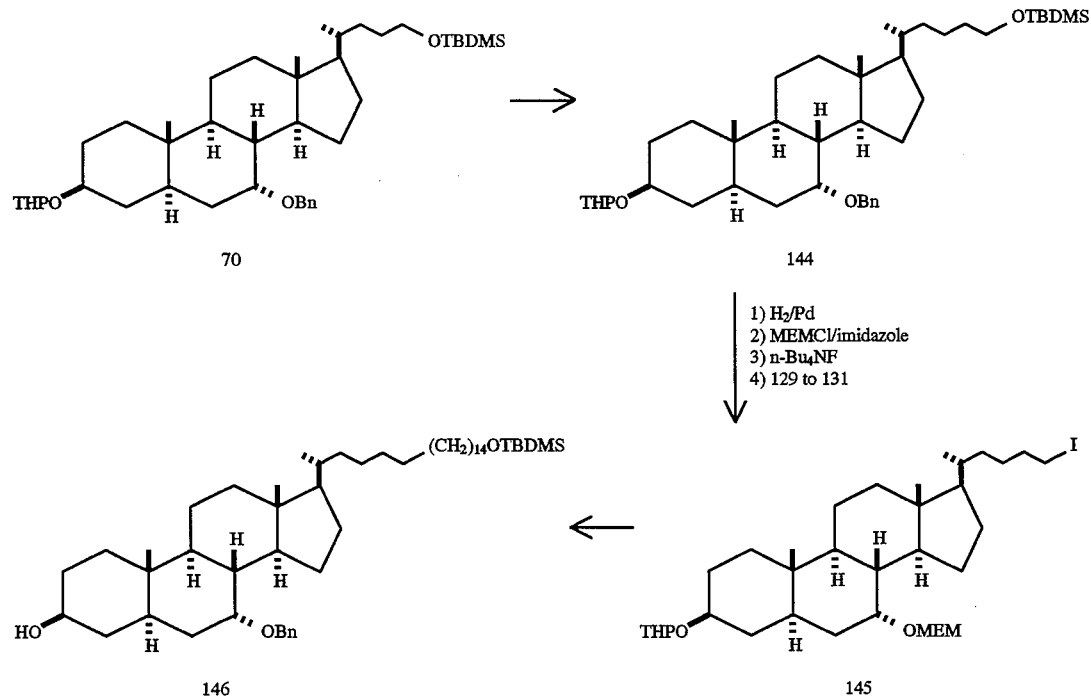

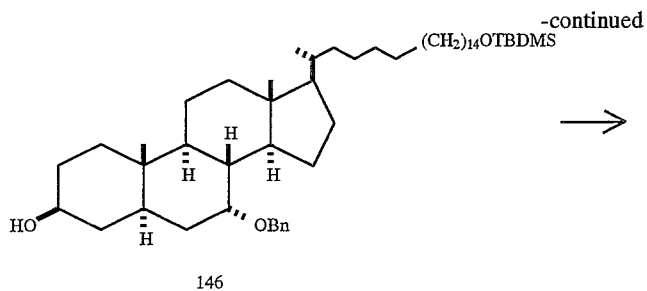

146

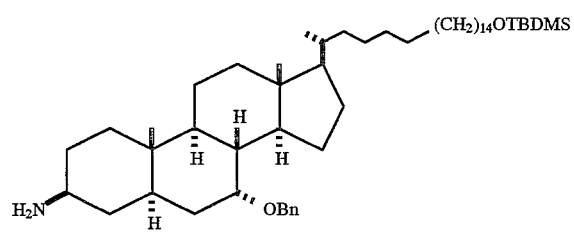

147

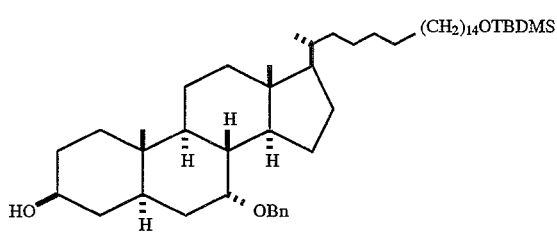

146

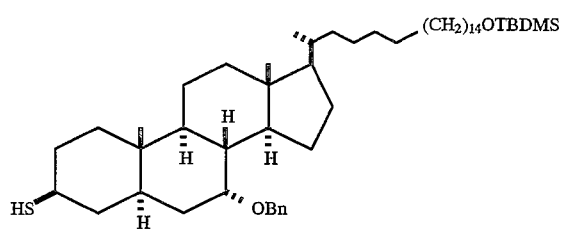

148

Compound 70 is converted to compound 144 in a manner analogous to the conversion of compound 116 to compound 121. Compound 144 is converted to iodide 145 by conversion of the benzyl protecting group to an MEM protecting group (hydrogenation followed by treatment with MEMCl and imidazole), removal of the TBDMS protecting group of the 25-alcohol, and conversion of this alcohol to the corresponding iodide, compound 145, in a manner analogous to the conversion of compound 129 to compound 131. Compound 145 is converted to compound 146 in a manner analogous to the conversion of compound 131 to compounds 138a-l utilizing acetylenic alcohol 1321 (n=12).

Compound 146 is converted to compound 147 in a manner analogous to the conversion of compound 11 to compound 14. Compound 146 is converted to compound 148 in a manner analogous to the conversion of compound 11 to compound 20.

EXAMPLE A(13)

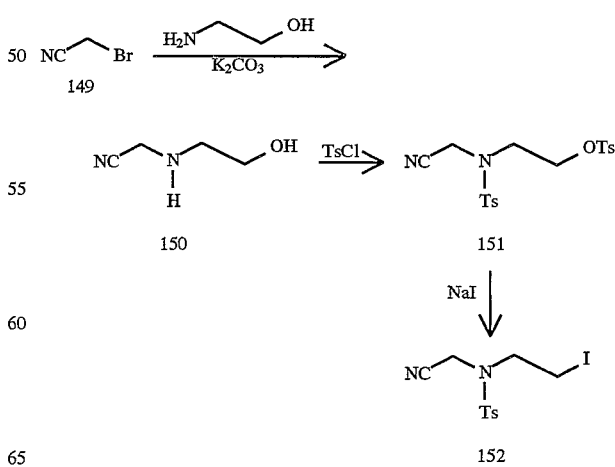

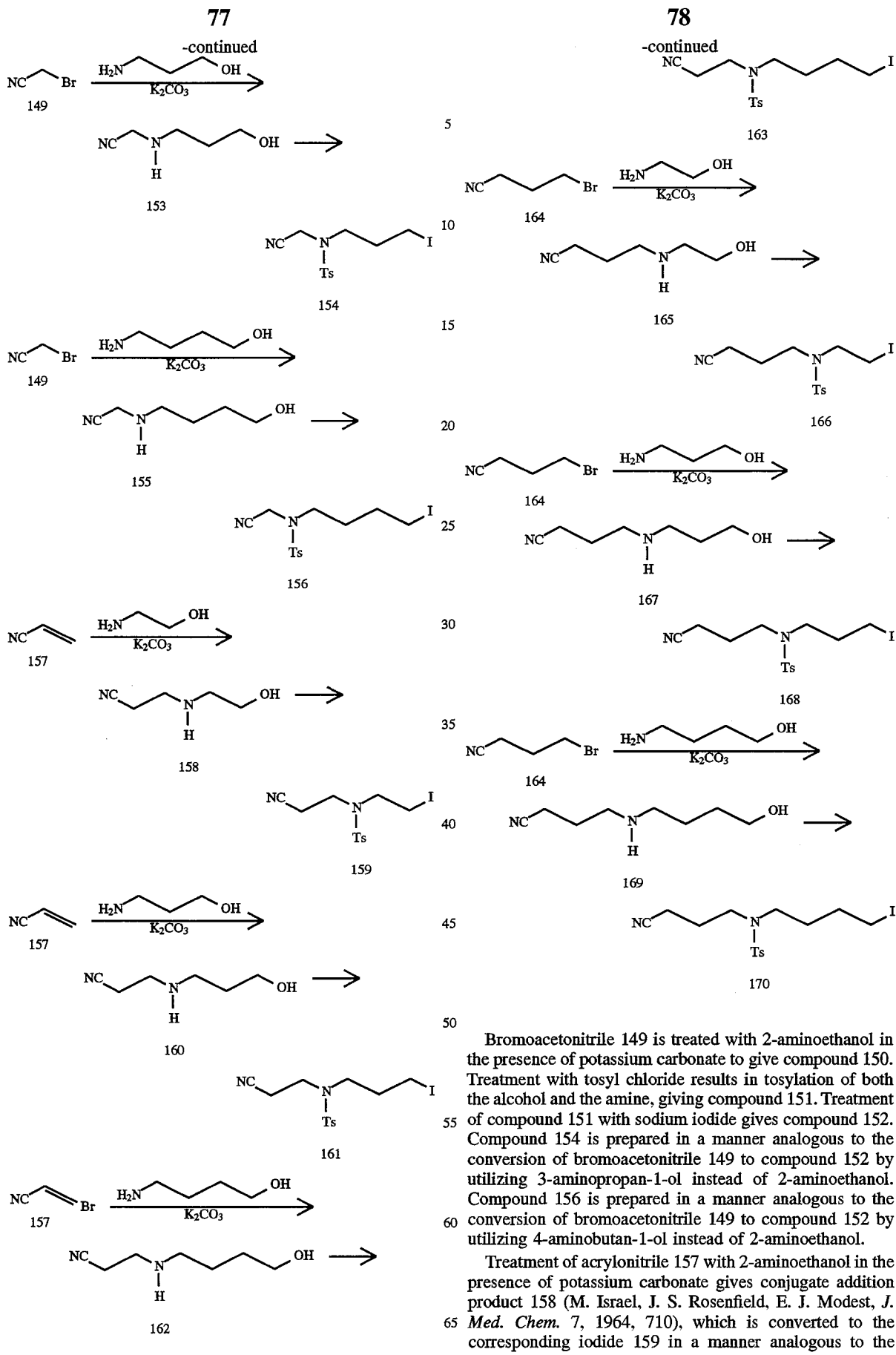

Bromoacetonitrile 149 is treated with 2-aminoethanol in the presence of potassium carbonate to give compound 150. Treatment with tosyl chloride results in tosylation of both the alcohol and the amine, giving compound 151. Treatment of compound 151 with sodium iodide gives compound 152. Compound 154 is prepared in a manner analogous to the conversion of bromoacetonitrile 149 to compound 152 by utilizing 3-aminopropan-1-ol instead of 2-aminoethanol. Compound 156 is prepared in a manner analogous to the conversion of bromoacetonitrile 149 to compound 152 by utilizing 4-aminobutan-1-ol instead of 2-aminoethanol.

Treatment of acrylonitrile 157 with 2-aminoethanol in the presence of potassium carbonate gives conjugate addition product 158 (M. Israel, J. S. Rosenfield, E. J. Modest, *J. Med. Chem.* 7, 1964, 710), which is converted to the corresponding iodide 159 in a manner analogous to the conversion of compound 150 to compound 152. Similarly, compound 161 is prepared from compound 157 in a manner analogous to the conversion of compound 157 to compound 159 utilizing 3-aminopropan-1-ol instead of 2-aminoethanol. Compound 163 is prepared from compound 157 in a manner analogous to the conversion of compound 157 to compound 159 utilizing 4-aminobutan-1-ol instead of 2-aminoethanol.

Compound 166 is prepared from compound 164 in a manner analogous to the conversion of bromoacetonitrile 149 to compound 152 using compound 164 instead of bromoacetonitrile 149. Compound 168 is prepared from compound 164 in a manner analogous to the conversion of bromoacetonitrile 149 to compound 154 using compound 164 instead of bromoacetonitrile 149. Compound 170 is prepared from compound 164 in a manner analogous to the conversion of bromoacetonitrile 149 to compound 156 using compound 164 instead of bromoacetonitrile 149.

EXAMPLE A(14)

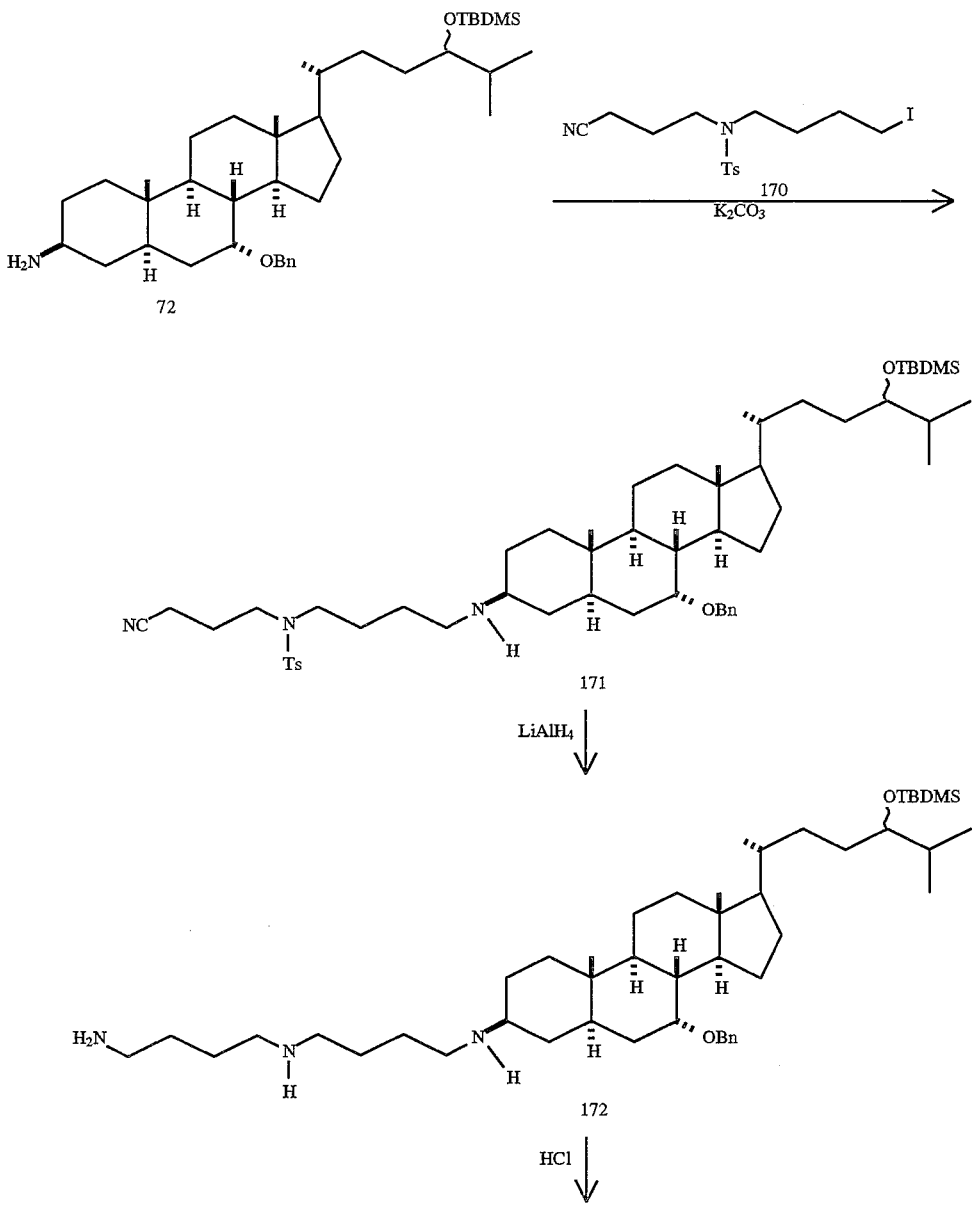

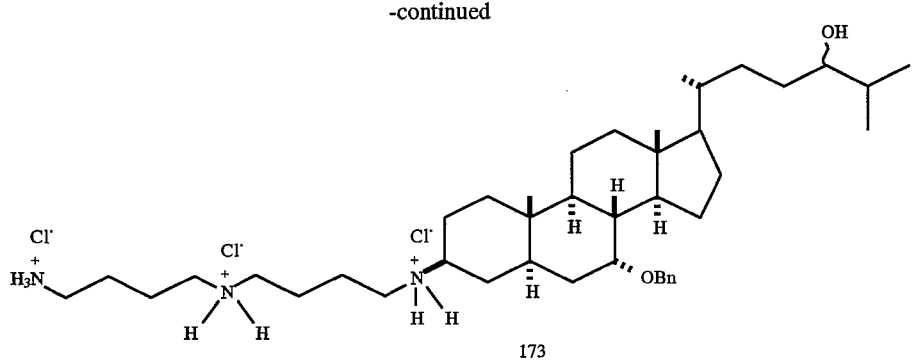

173

The cationic side chains (compounds 152, 154, 156, 159, 161, 163, 166, 168, and 170) are attached to the suitably protected flat ring systems (compounds 11, 14, 20, 21, 22, 23, 33, 34, 35, 36, 37, 38, 51, 52, 53, 64, 65, 66, 71, 72, 73, 74, 75, 76, 78, 79, 80, 81, 82, 83, 95, 98, 110, 111, 113, 114, 115, 122, 123, 124, 125, 126, 127, 138a-1, 139a-1, 140a-1, 146, 147, and 148) as illustrated for the conversion of compound 72 to compound 173. Thus, compound 72 is treated with the iodide 170 in the presence of potassium carbonate to give compound 171. Reduction of the nitrile to the corresponding amine and removal of the tosyl protecting group from the amine (T. W. Greene, P. G. M. Wuts, "Protective Groups in Organic Synthesis," 2nd ed., John Wiley and Sons, New York, 1991, 380) by treatment with lithium aluminum hydride yields compound 172. Treatment with HCl results in the formation of the trisammonium salt and removal of the TBDMS protecting group, giving compound 173.

EXAMPLE A(15)

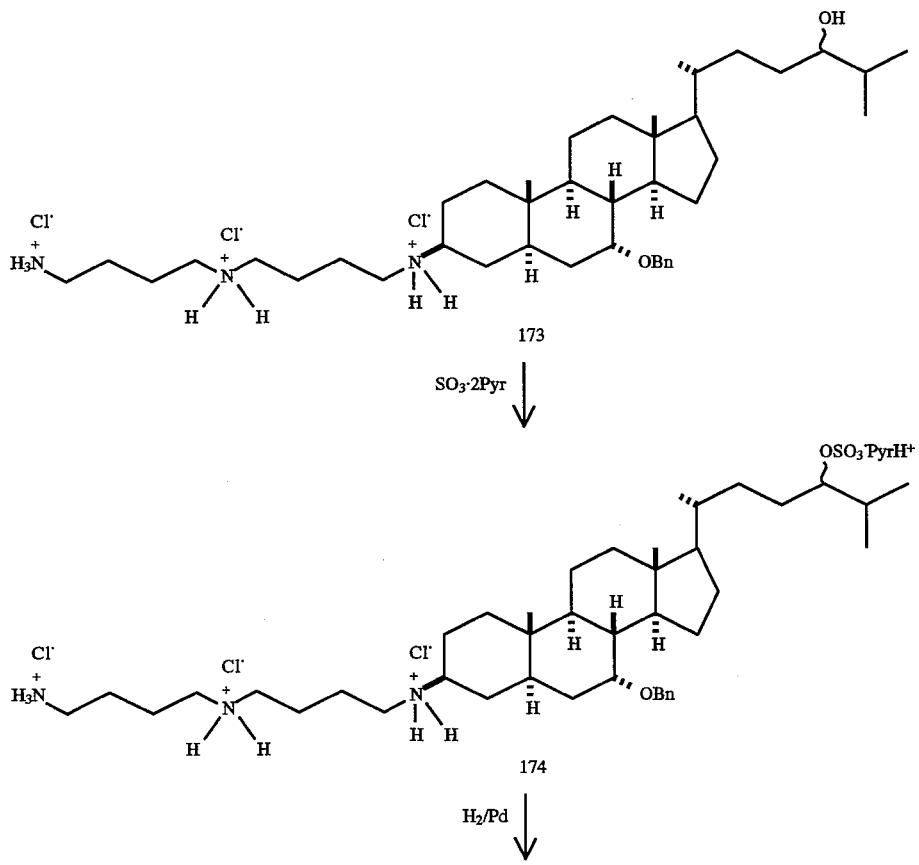

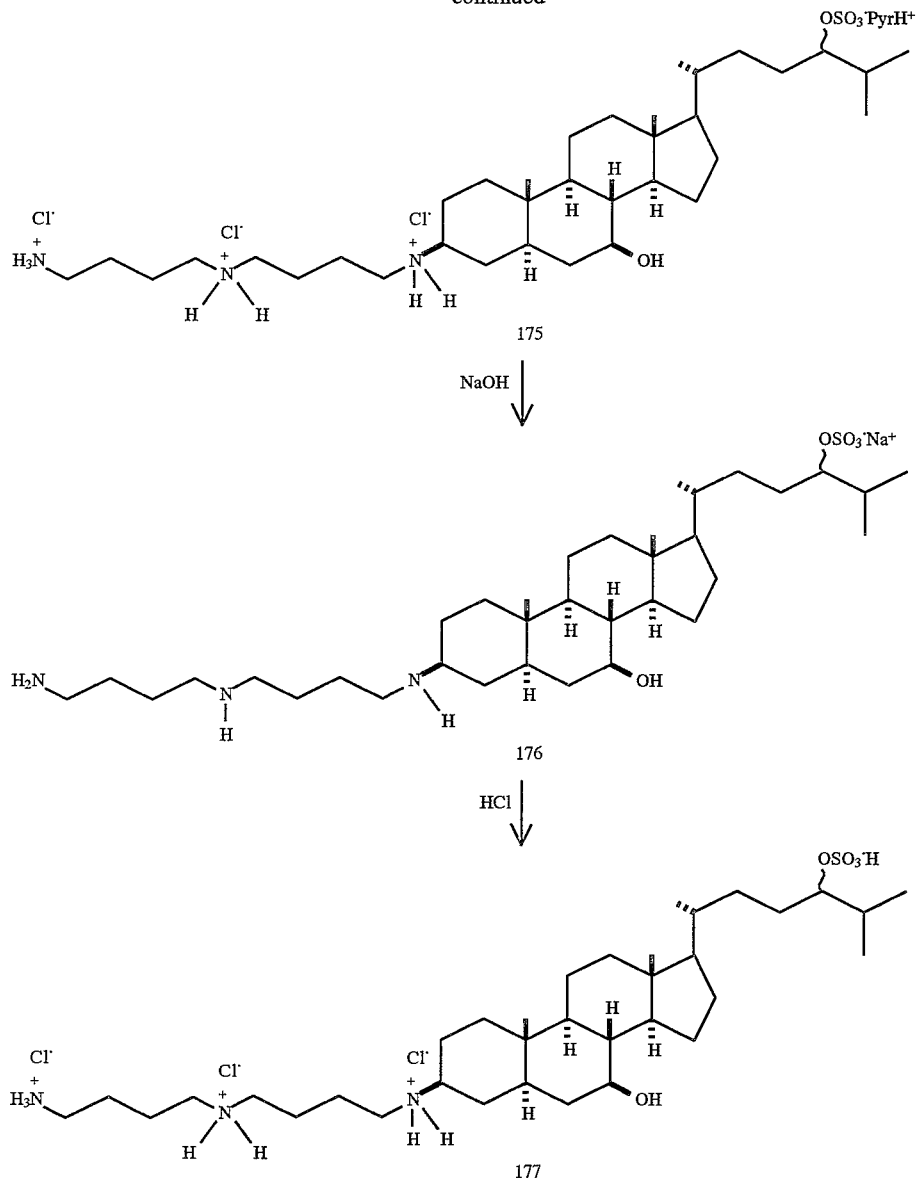

The introduction of a sulfate into the anionic side chain of a flat ring system with a cationic side chain attached is illustrated by the conversion of compound 173 to compound 177. Compound 173 is treated with sulfur trioxide dipyridine (S. Bernstein, J. P. Dusza, J. P. Joseph, "Chemical and Biological Aspects of Steroid Bioconjugation," S. Bernstein and S. Solomon (eds.), Springer-Verlag, New York, 1970, 25–36) to yield pyridinium sulfate 174. The benzyl protecting group is typically removed by hydrogenation with palladium as illustrated in the conversion of compound 174 to compound 175. It should be noted that in the cases where the flat ring system contains a double bond or the link between the flat ring system and the cationic side chain is a sulfur atom, other methods are used to remove the benzyl protecting group such as treatment with $Ph_3C^+BF_4^-$ (T. R. Hoye, A. J. Caruso, J. F. Dellaria, Jr., M. J. Kurth, *J. Am. Chem. Soc.* 104, 1982, 6704). Treatment of compound 175 with sodium hydroxide (giving compound 176) followed by HCl results in the formation of compound 177.

EXAMPLE A(16)
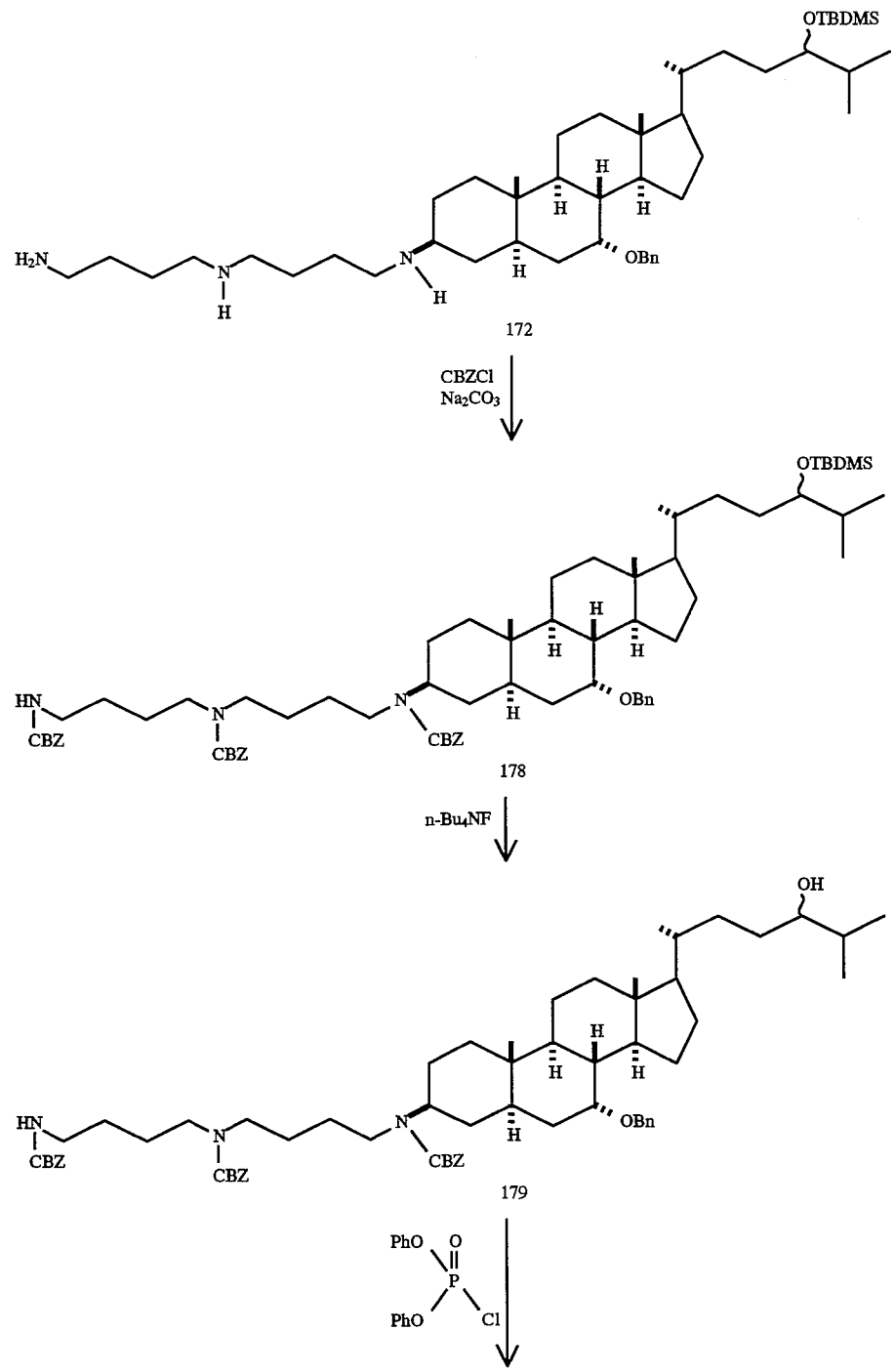

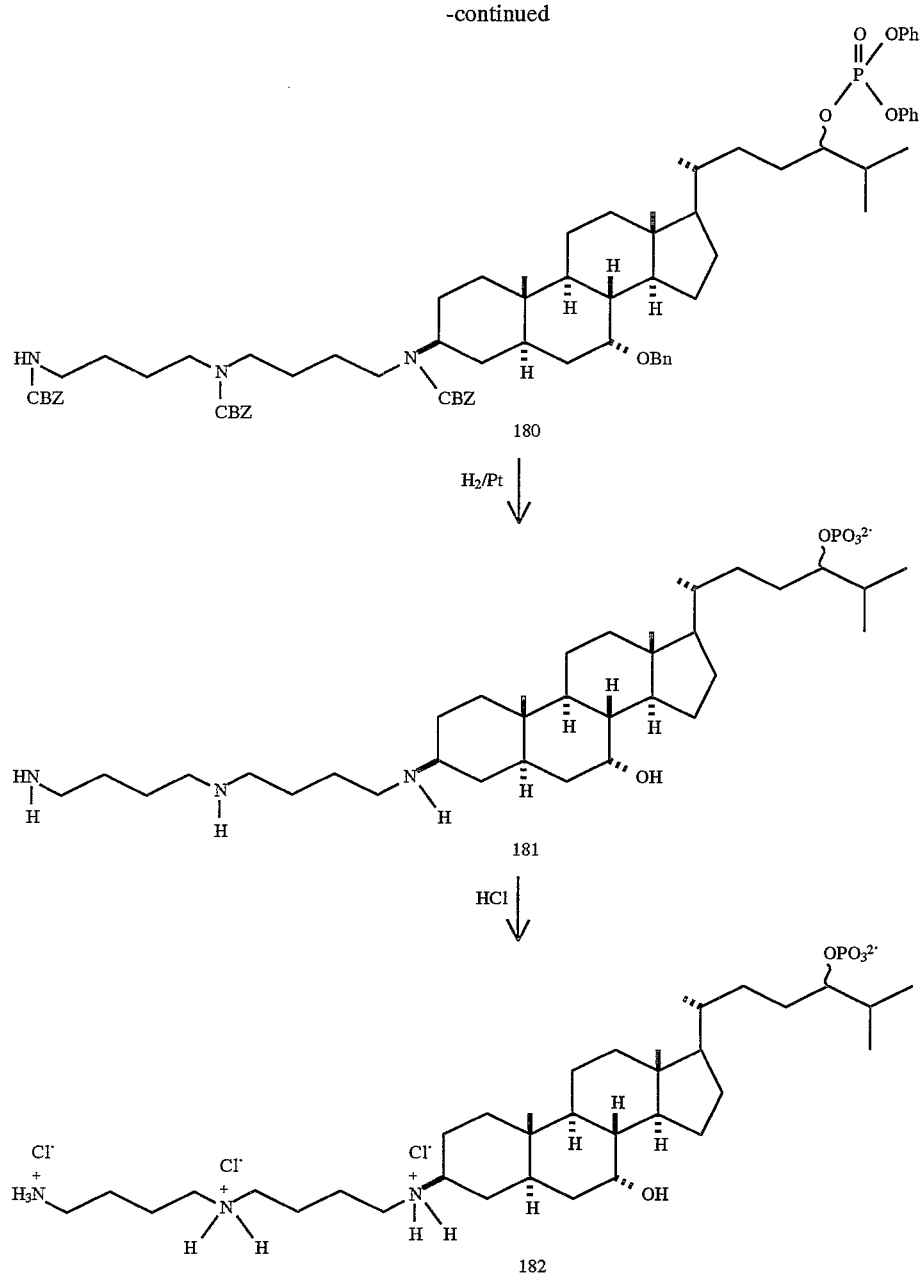

The introduction of a phosphate into the anionic side chain of a flat ring system with a cationic side chain attached is illustrated by the conversion of compound 172 to 181. The amines of compound 172 are protected as the benzyl carbamates to give compound 178 by treatment with PhCH$_2$OCOCl (CBZCl) in the presence of sodium carbonate. The TBDMS protecting group is then removed by treatment with tetra-n-butylammonium fluoride to give alcohol 179. Treatment of compound 179 with diphenyphosphoryl chloride gives compound 180 (H. G. Khorana, "Some Recent Developments in the Chemistry of Phosphate Esters of Biological Interest," John Wiley and Sons, New York, 1961, 16). Reduction of compound 180 with hydrogen/platinum followed by treatment with HCl results in the formation of compound 182.

EXAMPLE A(17)
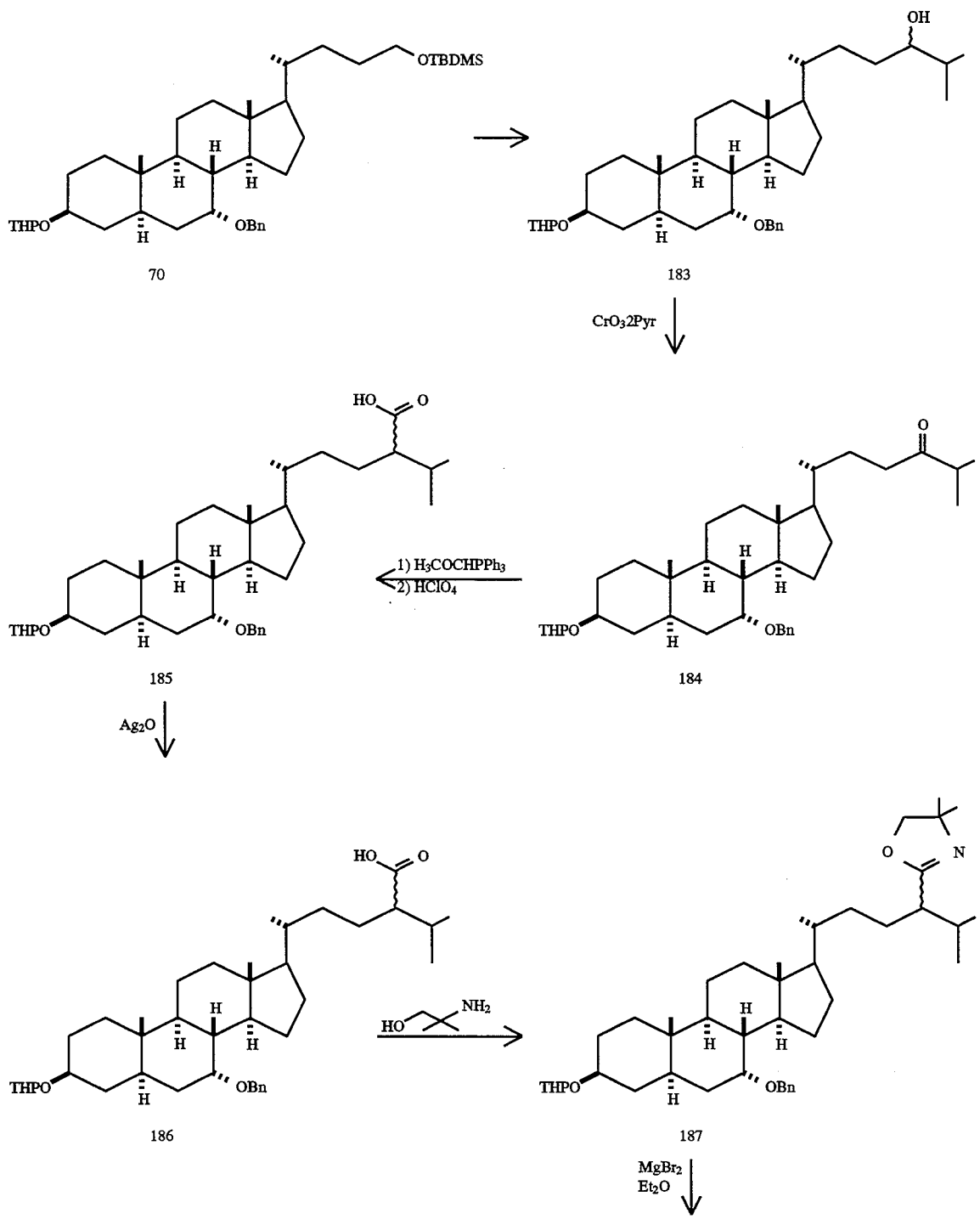

-continued
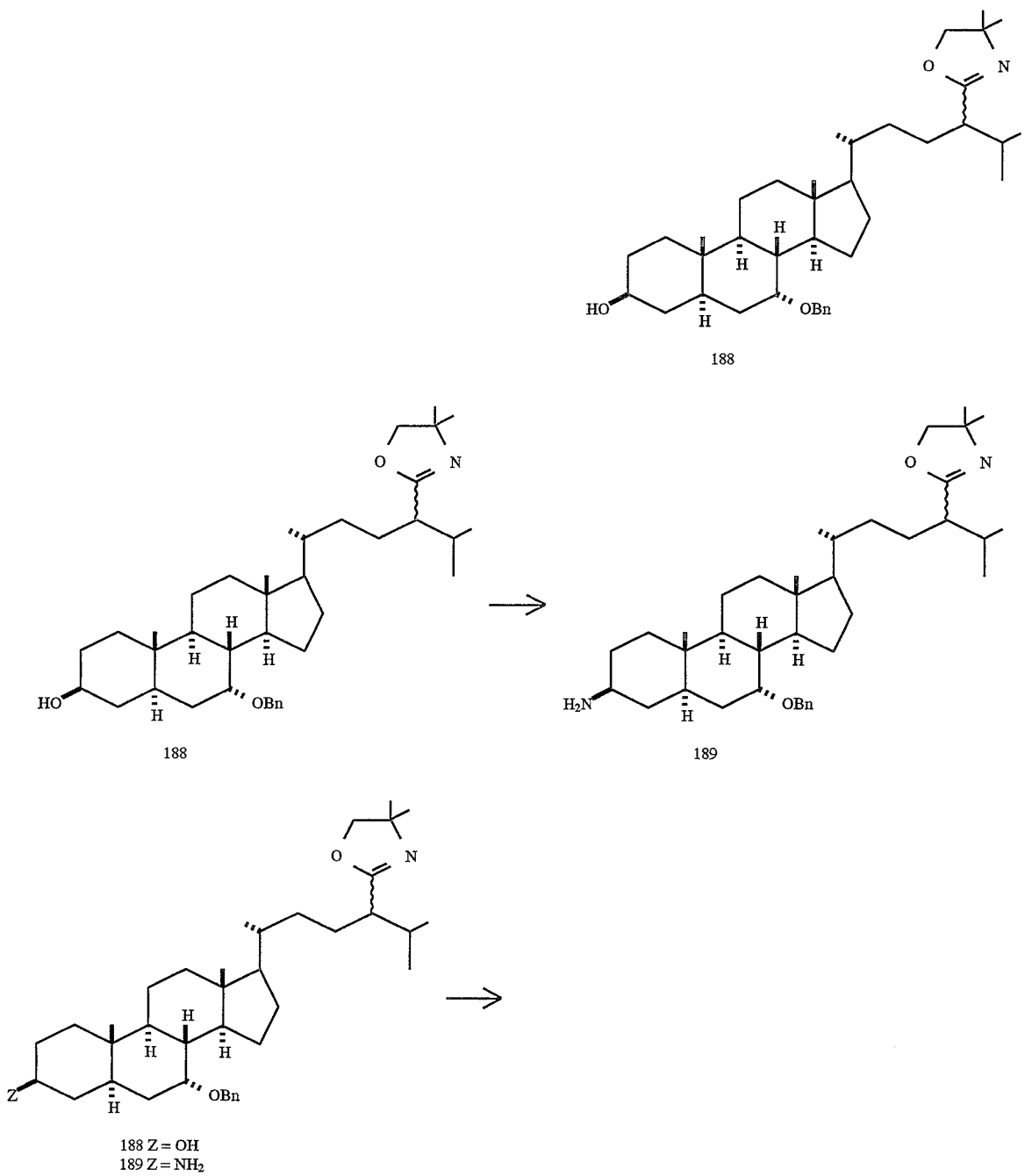
188 Z = OH
189 Z = NH₂

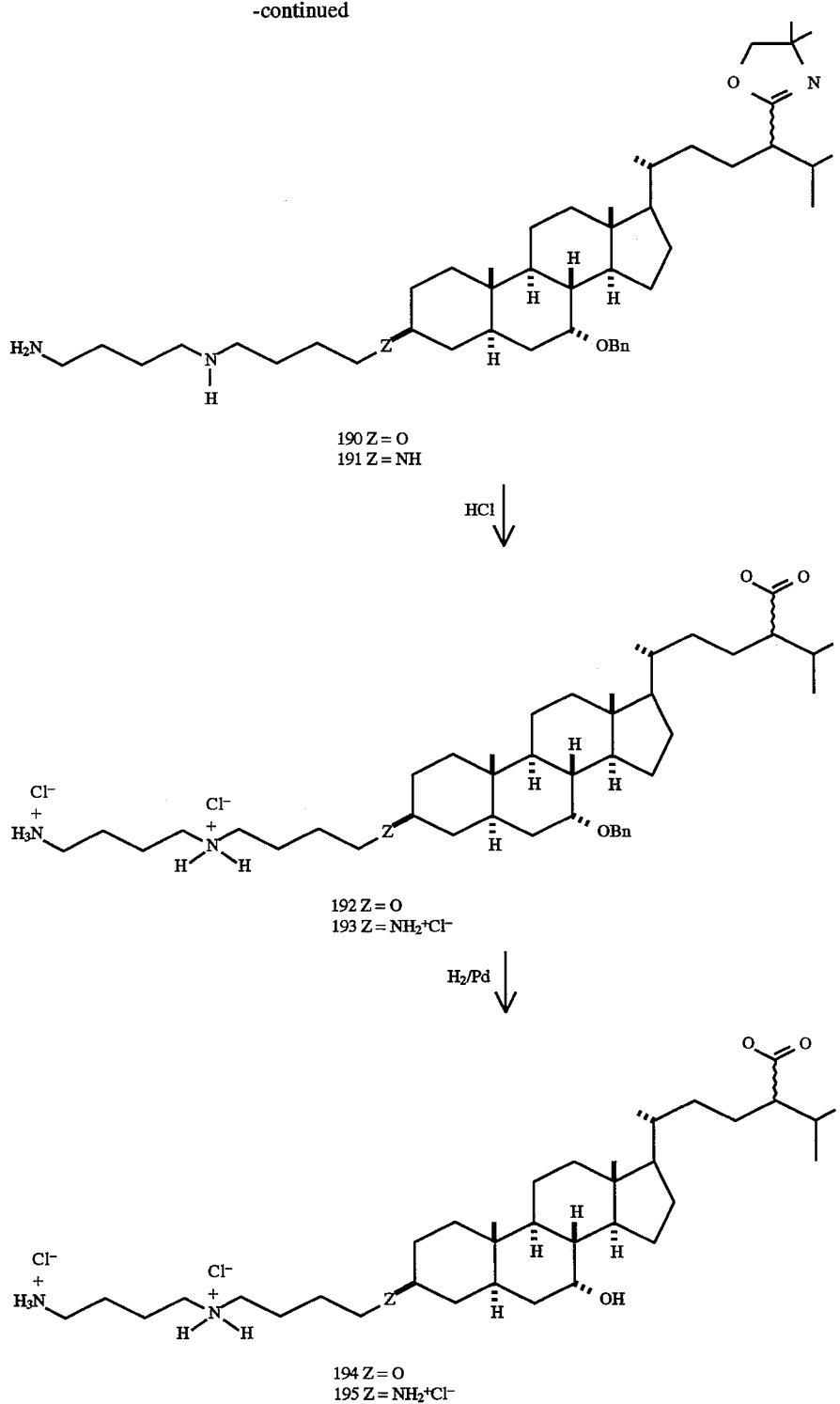

190 Z = O
191 Z = NH

192 Z = O
193 Z = NH₂⁺Cl⁻

194 Z = O
195 Z = NH₂⁺Cl⁻

Preparation of compounds with a carboxylate in the side chain requires that a protected carboxylic acid be introduced into the side chain prior to attachment of the cationic side chain. This general procedure is illustrated in the conversion of compound 70 to compounds 194 and 195. Compound 70 is converted to compound 183 in a manner analogous to the conversion of compound 6 to compound 9. The 24-alcohol is oxidized to ketone 184 with Collin's reagent. Compound 184 is treated with the ylide from methoxymethyltriphenylphosphonium bromide followed by HClO₄ to give compound 185 (L. L. Frye, C. H. Robinson, *J. Org. Chem.* 55, 1990, 1579). Oxidation of aldehyde 185 to carboxylic acid 186 is accomplished by treatment with silver oxide (E. J. Corey, N. W. Gilman, B. E. Ganem, *J. Am. Chem. Soc.* 90, 1968, 5616). The resultant carboxylic acid is protected as the 1,3-oxazoline by treatment with 2-amino-2-methylpropan-1-ol to give compound 187. Removal of the THP protecting group with magnesium bromide (S. Kim, J. H. Park, *Tetra-* hedron Lett. 28, 1987, 439) yields compound 188. Compound 188 is converted to the corresponding 3β-amine, compound 189, in a manner analogous to the conversion of compound 11 to compound 14. The cationic side chain is introduced in a manner analogous to the conversion of compound 72 to compound 172 to give compound 190 from compound 188 and compound 191 from compound 189. Treatment of compound 190 with HCl results in the removal of the oxazoline protecting group and protonation of the amines to give compound 192. Compound 191 is converted to compound 193 in a manner analogous to the conversion of compound 190 to compound 192. Treatment of compound 192 with hydrogen in the presence of palladium gives compound 194. Compound 193 is converted to compound 195 in a manner analogous to the conversion of compound 192 to compound 194.

EXAMPLE B

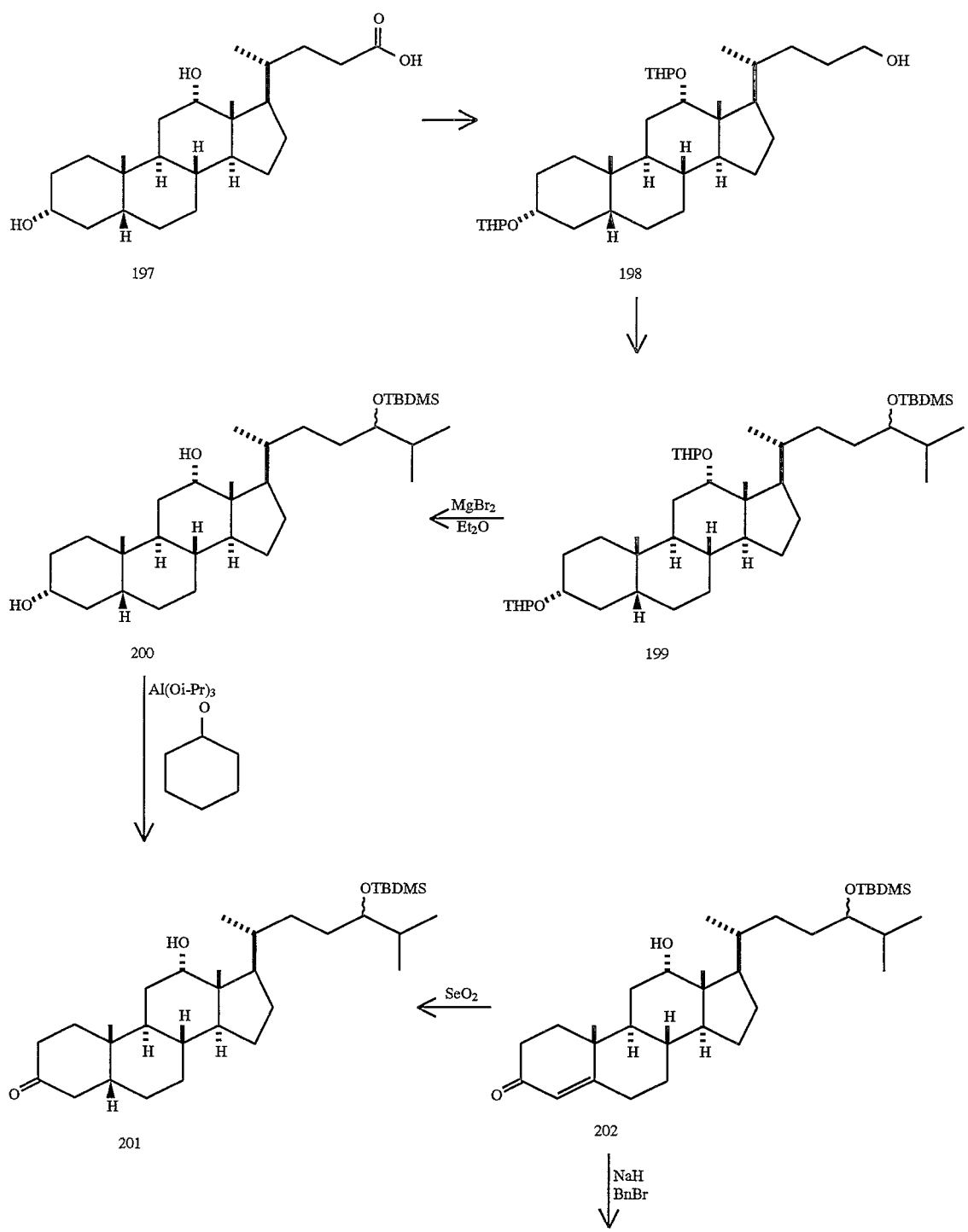

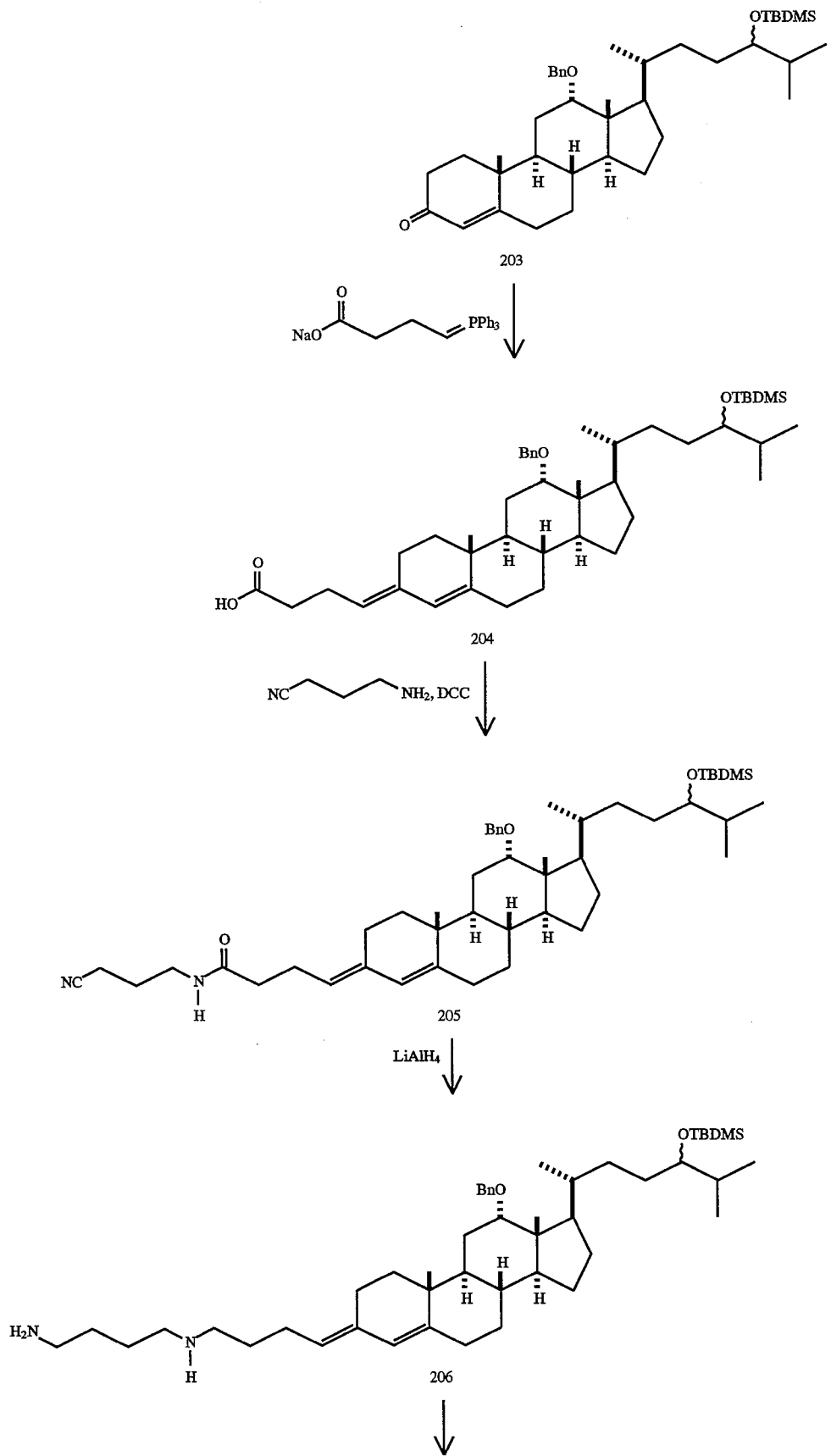

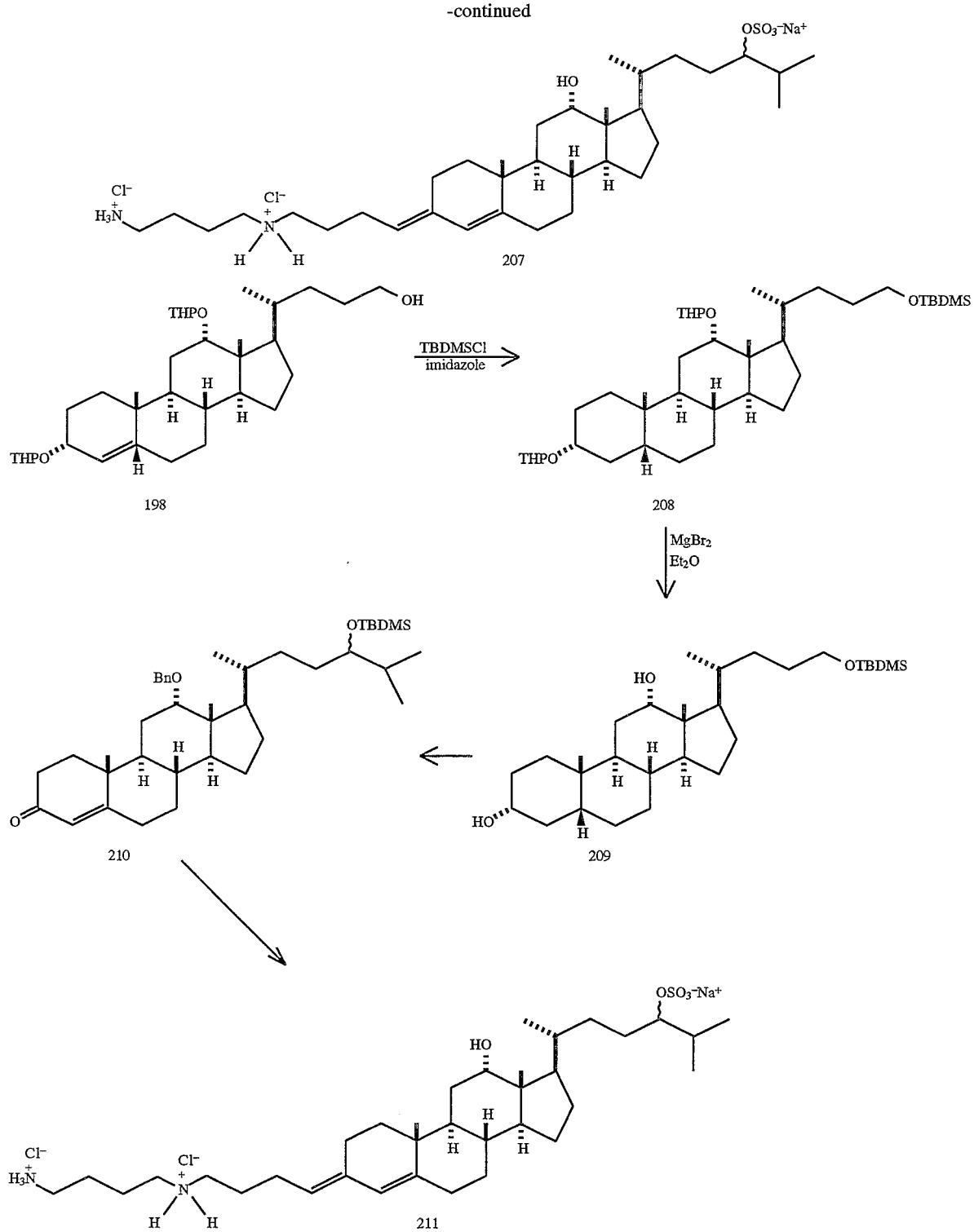

The preparation of compounds with a double bond in the Δ⁴-position of the flat ring system is illustrated by the preparation of compounds 207 and 211. Deoxycholic acid 197 is converted to compound 198 in a manner analogous to the conversion of cholenic acid 1 to compound 3. Compound 198 is then converted to compound 199 in a manner analogous to the conversion of compound 7 to compound 10. The THP protecting groups are then removed by treatment with magnesium bromide in ether to give compound 200 (S. Kim, J. H. Park, *Tetrahedron Lett.* 28, 1987, 439). The equatorial 3-hydroxyl is selectively oxidized with aluminum isopropoxide and cyclohexanone to give compound 201 (M. Ehrenstein, T. O. Stevens, *J. Org. Chem.* 5, 1940, 660). The double bond at C-4 is introduced by treatment of compound 201 with selenium dioxide (I. Bjorkhem, H. Danielsson, C. Issidorides, A. Kallner, *Acta Chem. Scand.* 19, 1965, 2151;

S. J. Branca, A. B. Smith, III, *J. Am. Chem. Soc.* 100, 1978, 7767), giving compound 202. The C-12 alcohol is then protected as the benzyl ether by treatment with benzyl bromide and sodium hydride to give compound 203. Compound 203 is condensed with the Wittig reagent derived from 5-triphenylphosphoniopentanoic acid and sodio-methyl-sulfinylcarbamide in dimethyl sulfoxide to give compound 204 (E. J. Corey, N. M. Weinshenker, T. K. Schaff, W. Huber, *J. Am. Chem. Soc.* 91, 1969, 5675). Compound 205 is then prepared by DCC mediated coupling of compound 204 with 4-aminobutanenitrile (F. Mares, J. E. Galle, S. E. Diamond, F. J. Regina, *J. Catal.* 112, 1988, 145). Reduction of the nitrile and the amide is accomplished by treatment with lithium aluminum hydride, giving compound 206. Compound 206 is converted to compound 207 in a manner analogous to the conversion of compound 172 to compound 177. The benzyl group is removed by treatment with $Ph_3C^+BF_4^-$ as in Example A(15).

The 24-hydroxyl of compound 198 is protected as the TBDMS ether by treatment with TBDMS chloride and imidazole to give compound 208 (E. J. Corey, A. Venkateswarlu, *J. Am. Chem. Soc.* 94, 1972, 6190). Selective removal of the THP protecting groups from the C-3 and C-12 alcohols by treatment with magnesium bromide in ether gives compound 209 (S. Kim, J. H. Park, *Tetrahedron Lett.* 28, 1987, 439). Compound 209 is converted to compound 210 is a manner analogous to the conversion of compound 200 to compound 203. Compound 210 is converted to compound 211 in a manner analogous to the conversion of compound 203 to compound 207.

EXAMPLE C

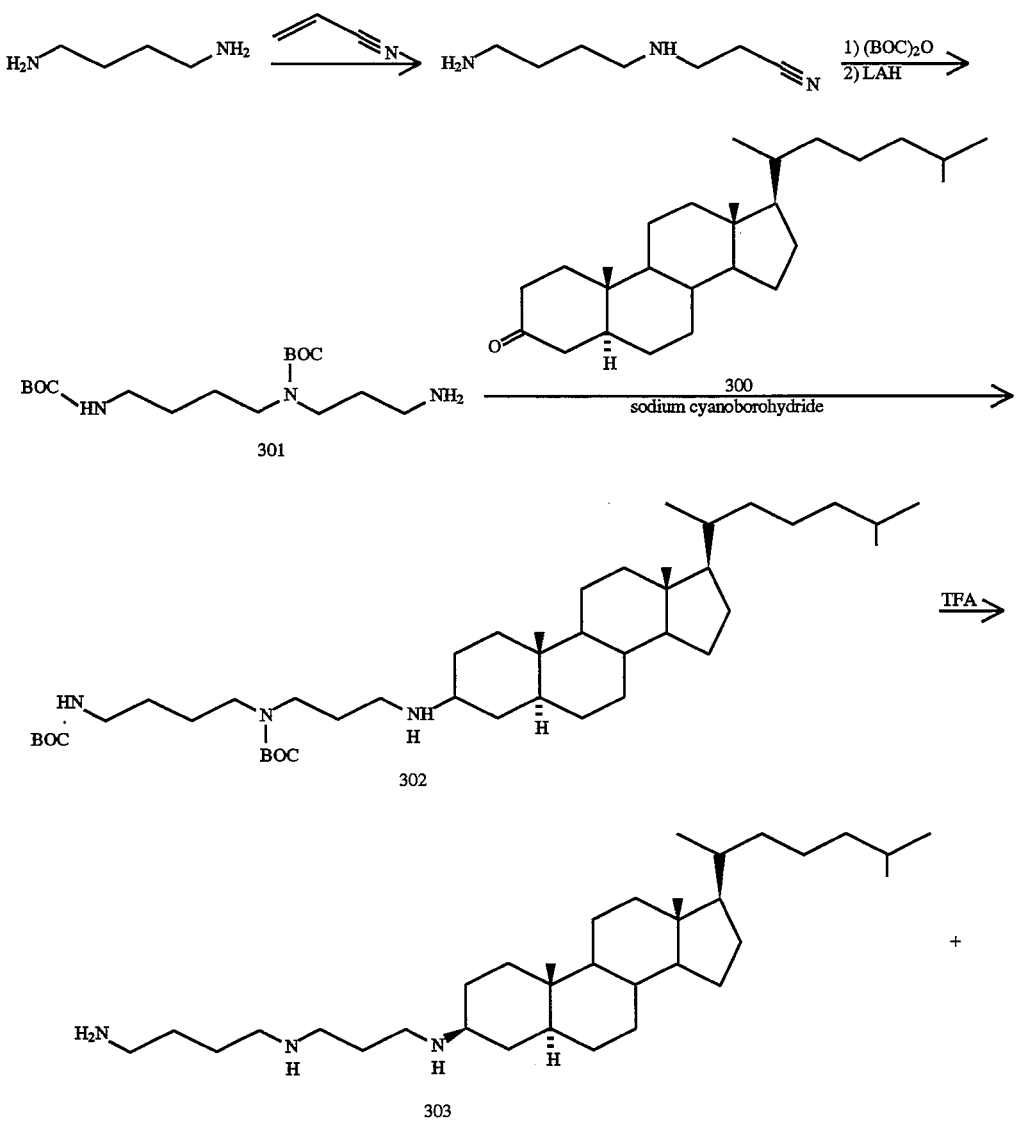

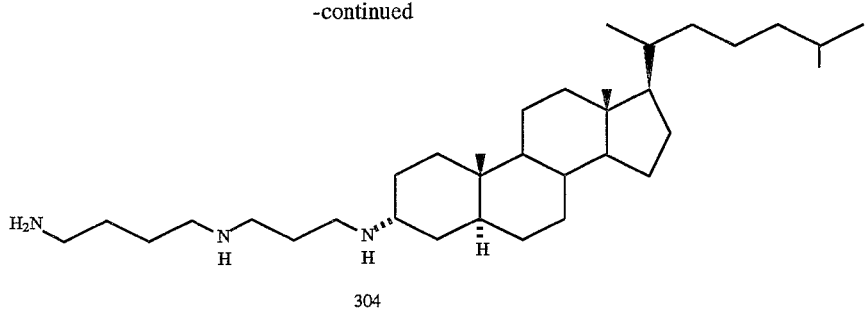

Preparation of compound 302: Reductive amination of 5α-cholestan-3-one affords a majority of the 3β-amino isomer (M. H. Boutigue, R. Jacquesy, *Bull. Soc. Chim. (France)*, 1973, 750–753). A solution of 5α-cholestan-3-one 300 (898 mg, 2.32 mmol) in dry tetrahydrofuran (10 ml) under nitrogen was treated with 3 Å molecular sieves (5 g) and the triamine 301 (K. Nakanishi et al., *Tetrahedron* 46 (9), 1990, 3267–3286) dissolved in dry methanol (25 ml). After 20 minutes at room temperature, sodium cyanoborohydride (696 mg, 11.0 mmol) was added and the reaction mixture was stirred for four days, filtered through Celite (diatomaceous earth material), and washed thoroughly with methanol and dichloromethane. After evaporation, the residue was partitioned between water (75 ml) and dichloromethane (75 ml), treated with 1N sodium hydroxide solution (15 ml) and brine (25 ml), and the layers were separated. The aqueous layer was extracted again with dichloromethane (75 ml) and the combined organics were dried ($Na_2SO_4$), filtered and evaporated. The resulting colorless oil was dissolved in dichloromethane and applied to a flash column (4-cm diameter, gradient elution with 2.5–3.5% 2N methanolic ammonia (available from Aldrich) in dichloromethane). A mixture of 3α,β-amino isomers 302 was obtained (1.18 g, 71% yield) as a white foam. $^1$H NMR (200 MHz, $CDCl_3$) δ: 4.57 (br s, NH), 3.3–3.0 (m, 6H), 2.7–2.4 (m, 3H), 2.0–1.0 (m, 37H), 1.45 (s, 9H), 1.44 (s, 9H), 0.91–0.84 (m, 9H), 0.78 (s, 3H), 0.64 (s, 3H); MS(+FAB): 716 (M+H, 100).

Preparation of compounds 303 and 304: A solution of compound 302 in chloroform (50 ml) was cooled to 0° C. and treated with trifluoroacetic acid (40 ml) under nitrogen. After stirring for fifty minutes at room temperature, the reaction mixture was concentrated, dissolved in chloroform and evaporated again (three times). The resulting solid was dissolved in methanol, treated with isopropylamine and preadsorbed onto silica gel. Flash chromatography (4 cm, gradient elution with 2:8:30 to 2:8:15 isopropylamine:methanol:dichloromethane) afforded the faster eluting material 304 (3α-amino isomer) in an impure state, followed by compound 303 (3β-amino isomer) as a solid (340 mg, 40% yield). $^1$H NMR (200 MHz, $CDCl_3$) δ: 2.8–2.6 (m, 8H), 2.47 (br m, 3α-H), 2.0–0.9 (m, 37H), 0.9–0.8 (m, 9H), 0.78 (s, 3H), 0.64 (s, 3H).

The HCl salt of compound 303 was prepared by dissolving the free base in chloroform, treating with 1N HCl in ether (10 ml), and evaporating in vacuo. The solid was recrystallized from methanol in ether (15 ml final volume) and the filtered solid was concentrated overnight under high vacuum to yield compound 303-3 HCl as a beige solid (261 mg, 26% yield). $^1$H NMR (200 MHz, $CD_3OD$) δ: 3.3–3.0 (m, 9H), 2.2–1.0 (m, 37H), 1.0–0.9 (m, 12H), 0.71 (s, 3H); MS(+FAB): 516.5 (M+H, 100); Anal. calcd. for $C_{34}H_{65}N_3$–3HCl—$H_2O$: C=63.48, H=10.97, N=6.53; Found: C=63.72, H=10.71, N=6.25.

Crude compound 304 was again purified by flash chromatography (2 cm, 1:4:20 isopropylamine:methanol:chloroform) to yield the free base (44 mg, 5% yield) ($^1$H NMR (200 MHz, $CD_3OD$) δ: 3.40 (m, 3β-H), 3.3–2.9 (m, 8H), 2.2–1.0 (m, 37H), 1.0–0.8 (m, 12H), 0.70 (s, 3H)), which was dissolved in methanol:dichloromethane (2 ml), treated with 1N HCl in ether (3 ml), concentrated in vacuo, and recrystallized from methanol in ether (1 ml final volume) to afford a gelatinous substance. After cooling in an ice bath, the solid was filtered, washed with ether, and concentrated under high vacuum to deliver 304-3 HCl (18 mg, 2% yield). $^1$H NMR (200 MHz, $CD_3OD$) δ: 3.45 (m, 3β-H), 3.3–3.0 (m, 8H), 2.3–1.0 (m, 37H), 1.0–0.9 (m, 12H), 0.70 (s, 3H); MS(+FAB): 516.6 (M+H, 100).

EXAMPLE D

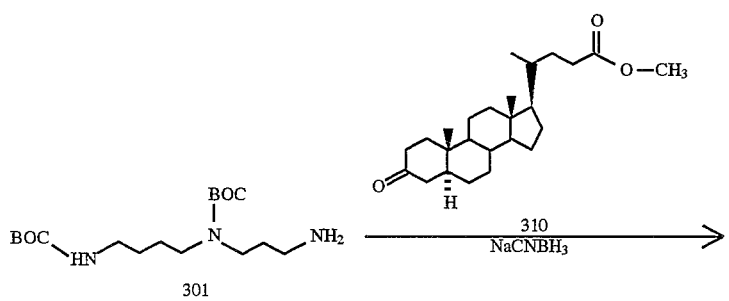

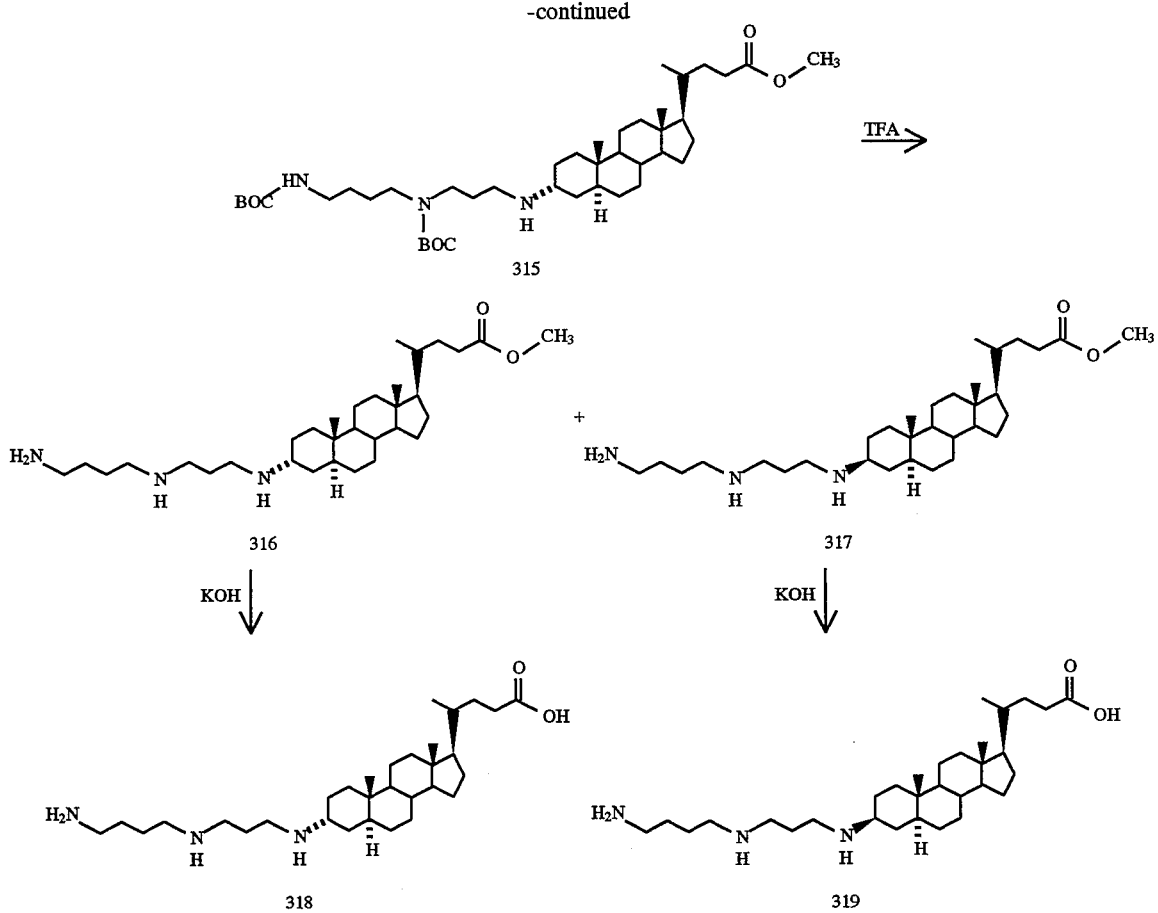

Preparation of compound 315: To a solution of 5α-cholanic acid-3-one methyl ester 310 (719 mg, 1.85 mmol) in anhydrous tetrahydrofuran (10 mi) was added 3 Å sieves (4 g), a solution of triamine 301 (650 mg, 1.88 mmol) in dry methanol (25 ml), and sodium cyanoborohydride (600 mg, 9.55 mmol). After stirring for eighteen hours at room temperature, the reaction mixture was filtered through Celite and washed with methanol (20 ml), dichloromethane (20 ml), 10% sodium hydroxide (15 ml), and brine (25 ml). The layers were separated and the aqueous layer was extracted with more dichloromethane (3×10 ml), and the combined organic layers were washed with brine, dried ($Na_2SO_4$), and evaporated. The crude material was purified by flash chromatography (2 cm, gradient elution with 2–4% 2N methanolic ammonia (Aldrich) in dichloromethane), affording compound 315 (1.09 g, 82% yield) as a mixture of C-3 isomers. $^1$H NMR (200 MHz, $CDCl_3$) δ: 4.57 (br s, NH), 3.65 (s, 3H), 3.4–3.0 (m, 6H), 2.8–2.5 (m, 3H), 2.4–1.0 (m, 34H), 1.45 (s, 9H), 1.44 (s, 9H), 0.91 (d, J=6 Hz, 3H), 0.78 (s, 3H), 0.64 (s, 3H); MS(+FAB): 719 (M+H, 100).

Preparation of compounds 316 and 317: A solution of compound 315 (910 mg, 1.27 mmol) in chloroform (39 ml) was treated with trifluoroacetic acid (33 ml) at 0° C. After one hour at room temperature, the reaction mixture was evaporated, dissolved in chloroform, and evaporated again (three times). The crude material was dissolved in methanol, treated with isopropylamine, and preadsorbed onto silica gel. Flash chromatography (2 cm, gradient elution with 1:4:15 to 1:4:6 isopropylamine:methanol:chloroform) yielded the 3α-amino isomer 316 as a crude product and 3β-amino isomer 317 as a pure product (319 mg, 48% yield).

$^1$H NMR (200 MHz, $CDCl_3$) δ: 3.66 (s, 3H), 2.8–2.6 (m, 8H), 2.47 (br m, 3α-H), 2.4–1.0 (m, 34H), 0.90 (d, J=6 Hz, 3H), 0.78 (s, 3H), 0.64 (s, 3H); MS(+FAB): 518 (M+H, 100).

Preparation of compound 318: Crude compound 316, obtained as described above, was dissolved in methanol (20 ml) and treated with 0.5N potassium hydroxide solution (15 ml) in methanol and water (5 ml). After refluxing for thirty minutes and leaving at room temperature overnight, the reaction mixture was purified in the manner described below for the isolation of compound 319, affording 3α-amino isomer 318 (50 mg, 8% yield, two steps). $^1$H NMR (200 MHz, $CD_3OD$) δ: 3.13 (m, 3β-H), 3.0–2.6 (m, 8H), 2.3–1.0 (m, 34H), 0.96 (d, J=6 Hz, 3H), 0.84 (s, 3H), 0.70 (s, 3H); IR (KBr, cm$^{-1}$): 2930, 2850, 1560, 1444, 1396, 1120, 752; MS(+FAB): 504 (M+H, 100).

Preparation of compound 319: A solution of compound 317 (240 mg, 0.46 mmol) in methanol (15 ml) was treated with 0.5N potassium hydroxide in methanol (10 ml) and water (3.3 ml) under nitrogen at reflux for 3.5 hours. After cooling to room temperature, the reaction mixture was acidified with 1N HCl to a pH of 4–5, extracted with chloroform (3×20 ml), and dried over $MgSO_4$. The solvent was evaporated and the product was purified by flash chromatography (1 cm, elution with 1:3:10 ammonium hydroxide:methanol:chloroform), affording 3β-amino isomer 319 as a beige solid (130 mg, 56% yield). $^1$H NMR (200 MHz, $CD_3OD$) δ: 2.9–2.6 (m, 9H), 2.2–1.0 (m, 34H), 0.95 (d, J=6 Hz, 3H), 0.84 (s, 3H), 0.70 (s, 3H); IR (KBr, cm$^{-1}$): 3268, 2928, 2850, 1560, 1444, 1396, 1118, 750; MS(+FAB): 504 (M+H, 100).

EXAMPLE E

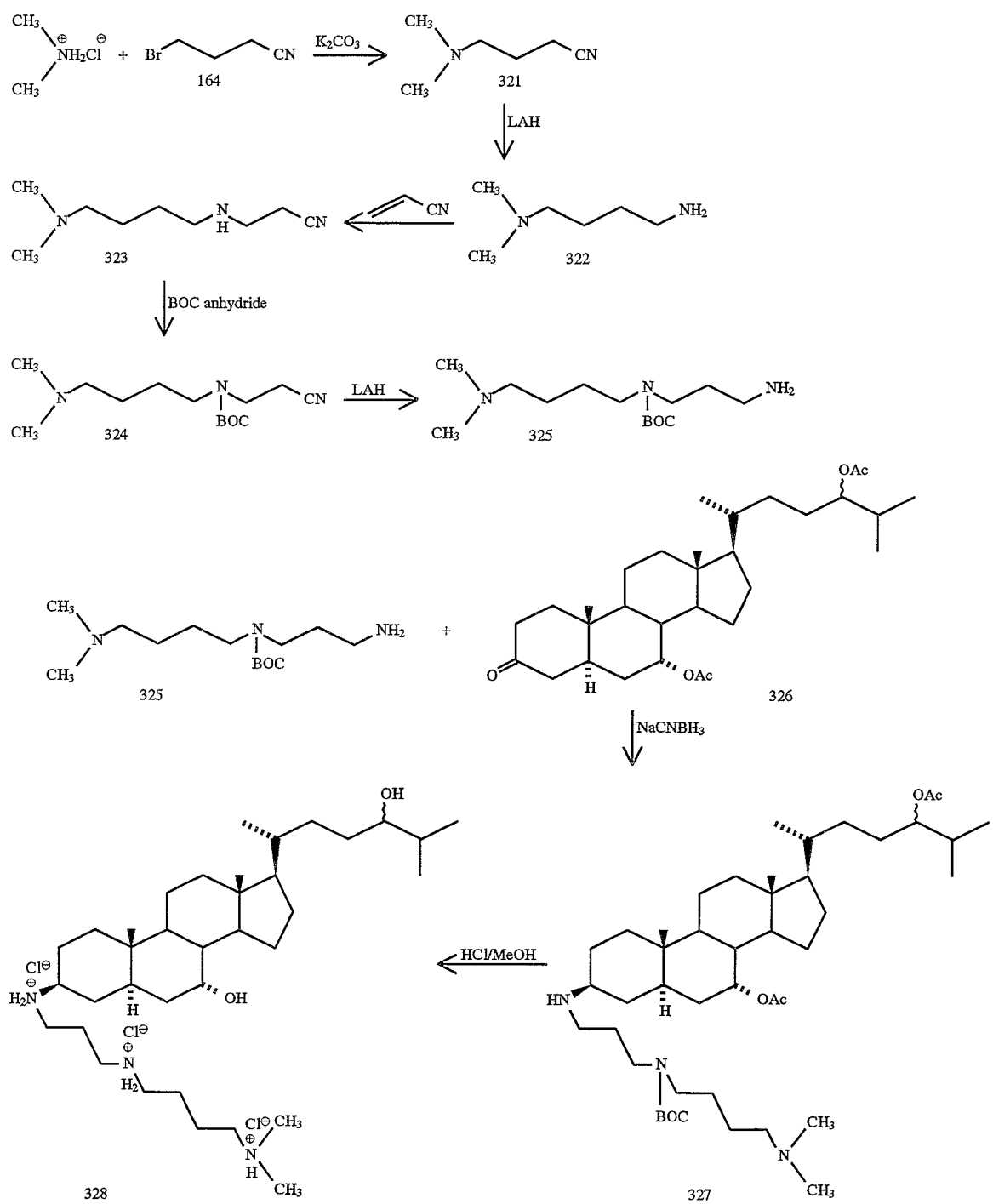

Preparation of side chain 325:

A solution of 3-cyanopropylbromide (4-bromobutyronitrile) 164 (6.38 g, 43.10 mmol) in dry acetonitrile (50 ml) was added dropwise to a gentle refluxing suspension of dimethylamine hydrochloride (5.27 g, 64.62 mmol) and anhydrous potassium carbonate (20.85 g, 150.86 mmol) in dry acetonitrile (100 ml). After the addition was complete, the reaction mixture was refluxed further for six hours. Acetonitrile was removed in vacuo, and the residue was extracted with ether (100 ml). Evaporation of ether in vacuo afforded N-(3-cyanopropyl)-N,N-dimethylamine 321 as a colorless oil (4.20 g, 87% yield based on 3-cyanopropylbromide). $^1$H NMR (400 MHz, CDCl$_3$) δ: 1.79 (2H, m, —CH$_2$—$\underline{CH_2}$—CH$_2$—), 2.20 (6H, s, —N(CH$_3$)$_2$), 2.37 (2H, t, —N$\underline{CH_2}$CH$_2$—), 2.41 (2H, t, —CH$_2$$\underline{CH_2}$CN).

To a suspension of lithium aluminum hydride (LAH) (4.74 g, 120.90 mmol) in dry ether (100 ml) was added dropwise a solution of N-(3-cyanopropyl)-N,N-dimethylamine 321 (4.10 g, 36.61 mmol) in dry ether (50 ml) at 0° C. After complete addition, the reaction mixture was stirred for two hours while allowing the temperature to raise from 0° C. to room temperature. The reaction mixture was quenched with 2N NaOH at 0° C. and the resulting white suspension was filtered through Celite and washed with ether. The ether filtrate was dried over $K_2CO_3$, filtered and concentrated in vacuo, yielding N,N-dimethyl-1,4-diaminobutane 322 as a colorless oil (2.5 g, 60% yield). $^1$H NMR (400 MHz, CDCl$_3$) δ: 1.43 (4H, m, —CH$_2$—CH$_2$—CH$_2$—CH$_2$—), 1.93 (2H, br s, —NH$_2$), 2.16 (6H, s, —N(CH$_3$)$_2$), 2.21 (2H, t, —CH$_2$CH$_2$N), 2.66 (2H, t, —CH$_2$CH$_2$NH$_2$).

A solution of acrylonitrile (1.17 g, 22.07 mmol) in methanol (1.0 ml) was added dropwise to a solution of N,N-dimethyl-1,4-diaminobutane 322 (2.1 g, 18.42 mmol) in methanol (10 ml) at 0° C. and the mixture was stirred at 0° C. for sixteen hours. Evaporation of the solvent in vacuo afforded almost pure N-(2-cyanoethyl)-N',N'-dimethyl-1,4-diaminobutane 323 as a colorless oil (2.5 g, 80% yield based on 322). $^1$H NMR (400 MHz, CDCl$_3$) δ: 1.45 (4H, m, —CH$_2$—CH$_2$—CH$_2$—CH$_2$—), 2.15 (6H, s, —N(CH$_3$)$_2$), 2.22 (2H, t, —CH$_2$N), 2.47 (2H, t, —CH$_2$CH$_2$CN), 2.60 (2H, t, —CH$_2$CH$_2$NH—), 2.88 (2H, t, —CH$_2$CH$_2$NH—), 3.37 (1H, s, —NH).

To a stirred solution of N-(2-cyanoethyl)-N',N'-dimethyl-1,4-diaminobutane 323 (2.0 g, 11.83 mmol) in dry dichloromethane (50 ml) was added dropwise a solution of di-tert-butyldicarbonate (2.84 g, 13.01 mmol) in dry dichloromethane (50 ml) at room temperature, and the mixture was stirred for sixteen hours. The reaction mixture was concentrated in vacuo, and the residue was dissolved in ethyl acetate (100 ml), washed with saturated NaHCO$_3$, washed with brine, dried over $K_2CO_3$, filtered, and evaporated in vacuo, producing N-(tert-butoxycarbonyl)-N-(2-cyanoethyl)-N',N'-dimethyl-1,4-diaminobutane 324 as a viscous oil (2.24 g, 70% yield), which was used in the next step without further purification. $^1$H NMR (400 MHz, CDCl$_3$) δ: 1.45 and 1.46 (9H+2H, merged s and m, —C(CH$_3$)$_3$ and —CH$_2$—CH$_2$—CH$_2$—), 1.52 (2H, m, —CH$_2$CH$_2$CH$_2$—), 2.19 (6H, s, —N(CH$_3$)$_2$), 2.25 (2H, t, —CH$_2$CH$_2$N), 2.59 (2H, m, —CH$_2$CN), 3.25 (2H, t, —CH$_2$CH$_2$NCO—), 3.25 (2H, t, —CH$_2$CH$_2$NCO—).

To a solution of LAH (0.62 mg, 16.30 mmol) in anhydrous ether (100 ml) was added N-(tert-butoxycarbonyl)-N-(2-cyanoethyl)-N',N'-dimethyl-1,4-diaminobutane 324 (2.22 g, 8.10 mmol) in anhydrous ether (50 ml) at 0° C. The mixture was stirred at 0° C. for thirty minutes. The excess LAH was quenched with 1N NaOH at 0° C., and the resulting suspension was filtered through Celite and washed with ether. The combined ether layers were washed with brine, dried over MgSO$_4$, and concentrated in vacuo to yield a crude product. The crude product was purified on a flash silica gel column and eluted with chloroform:methanol:isopropylamine (15:1:1) to give N-(3-aminopropyl)-N-(tert-butoxycarbonyl)-N',N'-dimethyl-1,4-diaminobutane 325 (1.30 g, 59% yield). $^1$H NMR (400 MHz, CDCl$_3$) δ: 1.40 (9H, s, t-Bu), 2.15 (6H, s, —N(CH$_3$)$_2$), 2.22 (2H, m), 2.65 (2H, t), 3.20 (4H, m).

Reductive amination to form compounds 327 and 328:

To a solution of 3-oxo-7α,24-diacetoxy-5α-cholestane 326 (490 mg, 1.00 mmol) and N-(3-aminopropyl)-N-(tert-butoxy-carbonyl)-N',N'-dimethyl-1,4-diaminobutane 325 (410 mg, 1.5 mmol) in methanol (30 ml) was added 3 Å molecular sieves (2.00 g) and NaCNBH$_3$ (94.2 mg, 1.50 mmol). The reaction mixture was stirred at room temperature for sixteen hours. After filtering through Celite, the methanol was removed in vacuo. The residue was purified on a flash silica gel column and eluted with chloroform:methanol:isopropylamine (15:1:1), producing 3β-N-{N-[3-(4-N',N'-dimethylaminobutyl)]-3-tert-butoxycarbonyl-1,3-diaminopropane}-7α,24-diacetoxy-5α-cholestane 327 (501 mg, 66% yield). $^1$H NMR (400 MHz, CDCl$_3$) δ: 0.63 (3H, s, 18-CH$_3$), 0.84 (3H, s, 19-CH$_3$), 2.04 (3H, s, CH$_3$CO$_2$—), 2.07 (3H, s, CH$_3$CO$_2$—), 2.38 (6H, br s, —N(CH$_3$)$_2$), 2.49 (1H, m, 3α-H), 4.67 (1H, m 24-H), 4.89 (1H, m, 7β-H).

To a solution of 3β-N-{N-[3-(4-N',N'-dimethylaminobutyl)]-3-tert-butoxycarbonyl-1,3-diaminopropane}-7α,24-diacetoxy-5α-cholestane 327 (400 mg, 0.52 mmol) in methanol (20 ml) was added methanol saturated with HCl gas (5 ml). The reaction mixture was stirred at room temperature for twenty-four hours. After removing the methanol in vacuo, the crude product was purified on a flash silica gel column and eluted with dichloromethane:methanol:ammonium hydroxide (7.5:2:0.5), giving 3β-N-1-{N-[3-(4-N',N'-dimethylaminobutyl)]-1,3-diaminopropane}-7α,24-dihydroxy-5α-cholestane 328, which was dissolved in methanol, treated with methanolic HCl and evaporated to yield 328·3 HCl (174 mg, 58% yield). $^1$H NMR (400 MHz, CDCl$_3$) δ: 0.65 (3H, s, 18-CH$_3$), 0.76 (3H, s, 19-CH$_3$), 2.18 (6H, s, —N(CH$_3$)$_2$), 2.45 (1H, m, 3α-H), 3.27 (1H, m 24-H), 3.79 (1H, m, 7β-H); MS(+FAB): 577 (M$^+$1, 41.48%), 576 (100%).

EXAMPLE F

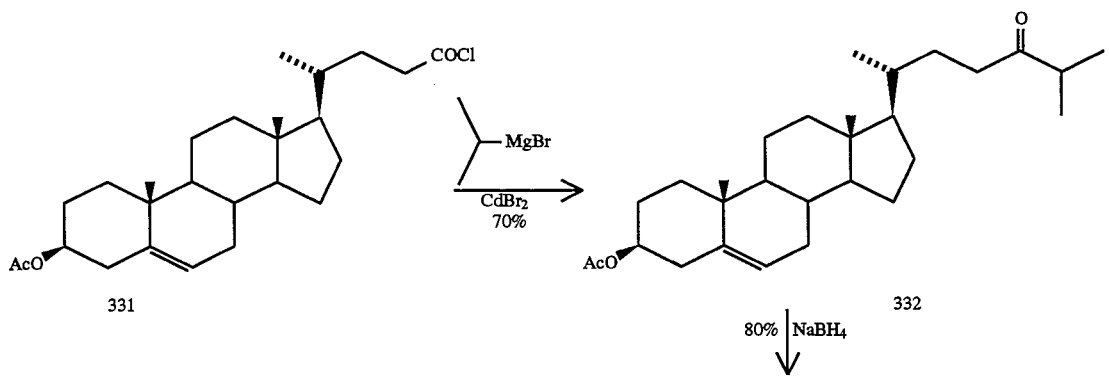

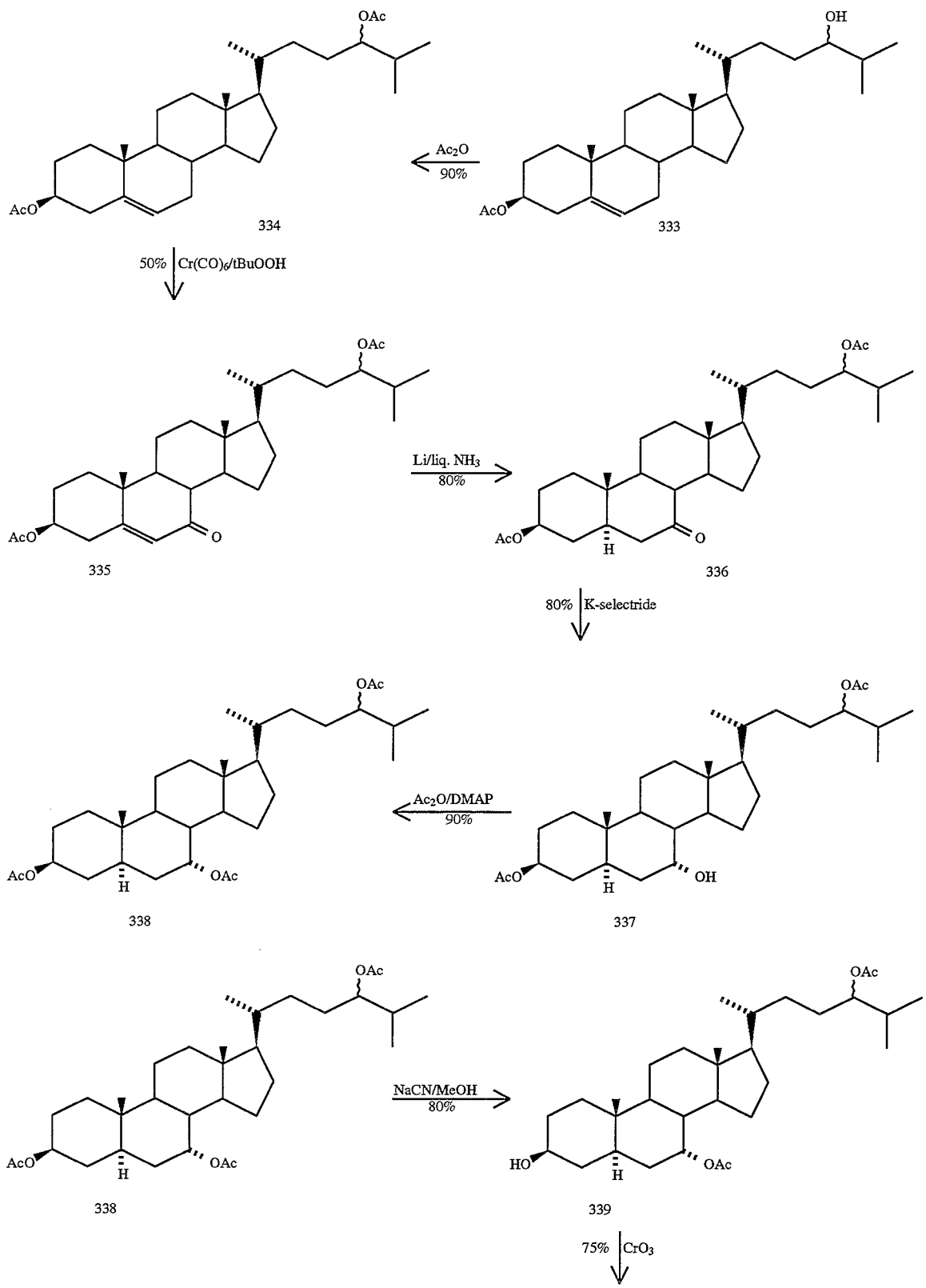

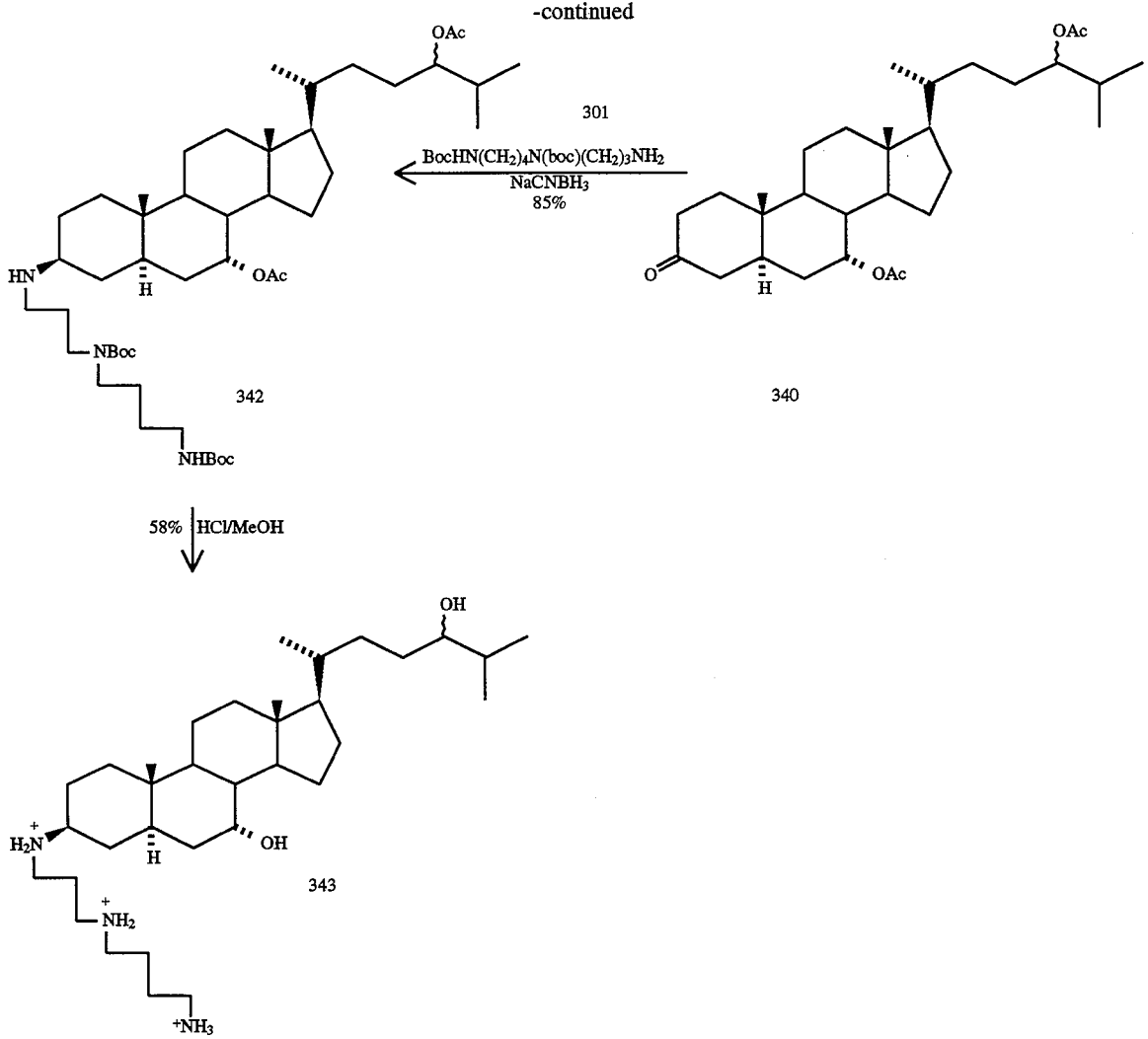

Preparation of compound 332: To a solution of 3β-acetoxy-5-cholenic acid (50.0 g, 118 mmole) in dry dichloromethane (200 ml) was added dropwise oxalyl chloride (30 ml, 448 mmole). The solution was stirred at room temperature for one hour and then concentrated in vacuo to obtain 3β-acetoxy-5-cholenic acid chloride 331. $^1$H NMR (400 MHz, CDCl$_3$) δ: 0.70 (3H, s, 18-CH$_3$), 0.95 (3H, d, 21-CH$_3$), 1.05 (3H, s, 19-CH$_3$), 2.04 (3H, s, —OCOCH$_3$), 4.60 (1H, m, 3α-H), 5.38 (1H, m, 6-H). Compound 331 was used in the following step without purification.

To a mixture of magnesium (24 g, 1.00 mole) in dry ether (500 ml) was added dropwise 2-bromopropane (60 ml, 639 mmole) while stirring. After the addition was completed, the reaction mixture was stirred for thirty minutes. The ethereal solution was transferred to another flask. Then to the resulting isopropyl-magnesium bromide solution was added portionwise cadmium bromide (75 g, 276 mmole) at room temperature. The resulting dark solution was refluxed gently for one hour, followed by the addition of dry benzene (200 ml), then most of the ether was removed. To this mixture, 3β-acetoxy-5-cholenic acid chloride 331 (50 g, 115 mmole) in dry benzene (300 ml) was added dropwise. The reaction mixture was stirred at room temperature for one hour and then poured slowly into a crushed ice and 10% hydrochloric acid mixture. The organic layer was separated. The aqueous layer was extracted with ether (3×300 ml). The combined ethereal solution was washed with 10% HCl, washed with water, dried (MgSO$_4$), filtered, and concentrated in vacuo to give crude product, 3β-acetoxy-24-oxo-5-cholestene 332 (35.6 g, 70% yield), which was used for the next reaction without further purification. $^1$H NMR (400 MHz, CDCl$_3$) δ: 0.69 (3H, s, 18-CH$_3$), 0.95 (3H, d, 21-CH$_3$), 1.04 (3H, s, 19-CH$_3$), 1.25 (6H, 2d, 26-CH$_3$, 27-CH$_3$), 2.04 (3H, s, —OCOCH$_3$), 4.61 (1H, m, 3α-H), 5.38 (1H, m, 6-H).

Preparation of compound 333: To a solution of 3β-acetoxy-24-oxo-5-cholestene 332 (35 g, 79.0 mmole) in methanol (300 ml) was added portionwise sodium borohydride (6.0 g, 158 mmole) while stirring. After the addition was completed, the reaction mixture was stirred for an additional hour and then poured slowly into crushed ice and 10% hydrochloric acid mixture. Most of the methanol was removed in vacuo. The aqueous solution was extracted with ether (3×300 ml). The combined ethereal solution was washed with 10% hydrochloric acid, washed with brine, dried (MgSO$_4$), filtered, and concentrated in vacuo. The crude product was purified by flash chromatography on silica gel (elution with 20% ethyl acetate in hexane) to give 3β-acetoxy-24ζ-hydroxy-5-cholestene 333 (27.7 g, 80% yield). $^1$H NMR (400 MHz, CDCl$_3$) δ: 0.69 (3H, s, 18-CH$_3$), 0.92 (9H, m, 21-CH$_3$, 26-CH$_3$, 27-CH$_3$), 1.02 (3H, s, 19-CH$_3$), 2.04 (3H, s, —OCOCH$_3$), 3.34 (1H, m, 24ζ-H), 4.60 (1H, m, 3α-H), 5.38 (1H, m, 6-H).

Preparation of compound 334: A solution of 3β-acetoxy-24ζ-hydroxy-5-cholestene 333 (20.0 g, 45 mmole), dry pyridine (200 ml, 2.5 mole) and acetic anhydride (30 ml, 318 mmole) was stirred at room temperature for sixteen hours. Then the reaction mixture was poured into crushed ice and saturated NaHCO$_3$ solution. The aqueous solution was extracted with ether (3×300 ml). The combined ether extracts were washed with saturated NaHCO$_3$ solution (2×100 ml), water (2×150 ml), 2N HCl (3×75 ml) and brine (1×100 ml), and then dried (MgSO$_4$) filtered and concentrated in vacuo to yield a crude product, which was purified by flash chromatography on silica gel (elution with 10% ethyl acetate in hexane) to give pure 3β,24ζ-diacetoxy-5-cholestene 334 (18.4 g, 90% yield). $^1$H NMR (400 MHz, CDCl$_3$) δ: 0.68 (3H, s, 18-CH$_3$), 0.90 (9H, m, 21-CH$_3$, 26-CH$_3$, 27-CH$_3$), 1.02 (3H, s, 19-CH$_3$), 2.07 (3H, s, —OCOCH$_3$), 2.09 (3H, s, —OCOCH$_3$), 4.58 (1H, m, 3α-H), 4.68 (1H, m, 24ζ-H), 5.38 (1H, m, 6-H).

Preparation of compound 335: A solution of 3β,24ζ-diacetoxy-5-cholestene 334 (15 g, 33.0 mmole), chromium hexacarbonyl (11.6 g, 52.7 mmole) and tert-butyl hydroperoxide (100 ml, 94 g, 1.04 mole) in dry acetonitrile (500 ml) was refluxed under argon for twelve hours. The acetonitrile was removed in vacuo, and the residue was dissolved in ether (500 ml). The ether extract was washed with saturated NaHCO$_3$ (3×150 ml) and brine (1×100 ml), dried (MgSO$_4$), filtered and concentrated in vacuo. The crude product was purified by flash chromatography on silica gel (elution with 20% ethyl acetate in hexane) to give pure 3β,24ζ-diacetoxy-7-oxo-5-cholestene 335 (8.26 g, 50% yield). 1HNMR (400 MHz, CDCl$_3$) δ: 0.68 (3H, s, 18-CH$_3$), 0.90 (9H, m, 21-CH$_3$, 26-CH$_3$, 27-CH$_3$), 1.22 (3H, s, 19-CH$_3$), 2.05 (6H, s, 2(—OCOCH$_3$)), 4.65 (2H, m, 3α-H and 24ζ-H), 5.69 (1H, m, 6-H).

Preparation of compound 336: To a solution of 3β,24ζ-diacetoxy-7-oxo-5-cholestene 335 (8.0 g, 16.0 mmole) in dry ether (50 ml) was added distilled liquid ammonia (approx. 200 ml) at −78° C. Lithium (0.5 g, 72.1 mmole) was added in small portions until a blue coloration persisted for ten minutes, after which the solution was quenched with solid NH$_4$Cl (approx. 50 g). The ammonia was evaporated, and the resulting residue was partitioned between water (500 ml) and ether (300 ml). The aqueous solution was extracted further with ether (3×200 ml). The combined ether extracts were washed with brine (1×100 ml), dried (MgSO$_4$), filtered and concentrated in vacuo to produce a crude product, which was purified by flash chromatography on silica gel (elution with 20% ethyl acetate in hexane) to afford pure 3β,24ζ-diacetoxy-7-oxo-5α-cholestane 336 (6.4 g, 80% yield). $^1$H NMR (400 MHz, CDCl$_3$) δ: 0.65 (3H, s, 18-CH$_3$), 0.90 (9H, m, 21-CH$_3$, 26-CH$_3$, 27-CH$_3$), 1.10 (3H, s, 19-CH$_3$), 2.02 (3H, s, —OCOCH$_3$), 2.04 (3H, s, —OCOCH$_3$), 2.35 (2H, t, 6-CH$_2$), 4.66 (2H, m, 3α-H and 24ζ-H).

Preparation of compound 337: To a solution of 3β,24ζ-diacetoxy-7-oxo-5α-cholestane 336 (6.0 g, 11.9 mmole) in dry tetrahydrofuran (200 ml) was added dropwise a solution of K-Selectride® (potassium tri-sec-butylborohydride) (1.0M in THF, 60 ml, 60 mmole) at −50° C. The reaction mixture was stirred at that temperature for five hours, and then quenched with 30% hydrogen peroxide solution (20 ml) and saturated NH$_4$Cl. The aqueous solution was extracted with ether (3×100 ml). The combined ether extracts were washed with saturated NaHCO$_3$ (2×70 ml), water (2×100 ml) and brine (1×70 ml), and then dried (MgSO$_4$), filtered and concentrated in vacuo to give a crude product. The crude product was purified by flash chromatography on silica gel (elution with 30% ethyl acetate in hexane) to give pure 3β,24ζ-diacetoxy-7α-hydroxy-5α-cholestane 337 (4.8 g, 80% yield). $^1$H NMR (400 MHz, CDCl$_3$) δ: 0.68 (3H, s, 18-CH$_3$), 0.82 (3H, s, 19-CH$_3$), 0.91 (9H, m, 21-CH$_3$, 26-CH$_3$, 27-CH$_3$), 2.05 (3H, s, —OCOCH$_3$), 2.08 (3H, s, —OCOCH$_3$), 3.82 (1H, m, 7β-H), 4.65 (2H, m, 3α-H and 24ζ-H); CIMS(m/e): 505 (M$^+$+1, 5%), 487 (11.0%), 443 (9.8%), 427 (100%), 367 (39.3%).

Preparation of compound 338: To a solution of 3β,24ζ-diacetoxy-7α-hydroxy-5α-cholestane 337 (4.0 g, 7.92 mmole) and 4-dimethylaminopyridine (9.66 g, 79.2 mole) in dry CH$_2$Cl$_2$ (40 ml) was added acetic anhydride (6.5 g, 73.4 mole) at room temperature. After eighteen hours, methanol was added to the reaction mixture, then the organic solvents were evaporated in vacuo to get oily residue. The residue was dissolved in EtOAc (100 ml), washed with 2N HCl (3×25 ml), water (1×50 ml), saturated NaHCO$_3$ (3×25 ml) and brine (1×25 ml), and then dried (MgSO$_4$), filtered and evaporated in vacuo. The resulting crude product was purified by flash chromatography on silica gel (elution with 20% ethyl acetate in hexane) to give 3β,7α, 24ζ-triacetoxy-5α-cholestane 338 (3.9 g, 90% yield) as a white solid. $^1$H NMR (400 MHz, CDCl$_3$) δ: 0.66 (3H, s, 18-CH$_3$), 0.84 (3H, s, 19-CH$_3$), 0.90 (9H, m, 21-CH$_3$, 26-CH$_3$, 27-CH$_3$), 2.05 (3H, s, —OCOCH$_3$), 2.07 (3H, s, —OCOCH$_3$), 2.10 (3H, s, —OCOCH$_3$), 4.68 (2H, m, 3α-H and 24ζ-H), 4.88 (1H, m, 7β-H); CIMS(m/e): 548 (M$^+$+1, 1.0%), 487 (11.0%), 443 (9.8%), 427 (100%), 367 (39.3%).

Preparation of compound 339: A solution of 3β, 7α,24ζ-triacetoxy-5α-cholestane 338 (2.20 g, 4.02 mmole) and sodium cyanide (0.20 g, 4.08 mmole) in methanol (70 ml) was stirred at room temperature for forty hours. After completion of the reaction, methanol was evaporated in vacuo, and the residue was extracted with CH$_2$Cl$_2$ (3×30 ml). The combined CH$_2$Cl$_2$ extracts were concentrated in vacuo to give 7α, 24ζ-diacetoxy-3β-hydroxy-5α-cholestane 339 as a white solid (1.62 g, 80% yield). $^1$H NMR (400 MHz, CDCl$_3$) δ: 0.66 (3H, s, 18-CH$_3$), 0.82 (3H, s, 19-CH$_3$), 0.91 (9H, m, 21-CH$_3$, 26-CH$_3$, 27-CH$_3$), 2.05 (3H, s, —OCOCH$_3$), 2.08 (3H, s, —OCOCH$_3$), 3.60 (1H, m, 3α-H), 4.67 (1H, m, 24ζ-H), 4.88 (1H, m, 7β-H); CIMS(m/e): 505 (M$^+$+1, 3.7%), 487 (4.4%), 444 (19.1%), 401 (11.0%), 385 (100%), 367 (31.9%).

Preparation of compound 340: To a solution of 7α, 24ζ-diacetoxy-3β-hydroxy-5α-cholestane 339 (1.5 g, 2.97 mmole) in acetone (100 ml) was added Jones reagent (aqueous chromic acid solution; CrO$_3$ in sulfuric acid and water) dropwise at 0° C. until an orange color persisted. The reaction mixture was stirred at 0° C. for ten minutes, then isopropanol was added until a green color was observed. Water (50 ml) and sodium acetate (5 g) were added to the mixture, and then the organic solvents were removed in vacuo. The residue was extracted with CHCl$_3$ (3×50 ml). The combined organic extracts were washed with saturated NaHCO$_3$ (2×50 ml), water (2×50 ml) and brine (1×50 ml), and then dried (MgSO$_4$), filtered and evaporated in vacuo to provide a crude product, which was purified by flash chromatography on silica gel (elution with 20% ethyl acetate in hexane), affording pure 3-oxo-7α, 24ζ-diacetoxy-5α-cholestane 340 as a white solid (1.12 g, 75% yield). $^1$HNMR (400 MHz, CDCl$_3$) δ: 0.66 (3H, s, 18-CH$_3$), 0.82 (9H, m, 21-CH$_3$, 26-CH$_3$, 27-CH$_3$), 0.99 (3H, s, 19-CH$_3$), 1.98 (3H, s, —OCOCH$_3$), 2.01 (3H, s, —OCOCH$_3$), 4.63 (1H, m, 24ζ-H), 4.88 (1H, m, 7β-H); CIMS(m/e): 442 (8.3%), 383 (100%), 312 (6.4%).

Preparation of compound 301: To a solution of 1,4-diaminobutane (4.3 g, 48.8 mmole) in methanol (1.5 ml) was added a solution of acrylonitrile (3.1 g, 58.4 mmole) in methanol (1.5 ml) at 0° C., and the mixture was stirred for twelve hours. Evaporation of the solvent in vacuo afforded N-(2'-cyanoethyl)-1,4-diaminobutane as a colorless oil (5.5 g, 80% yield). $^1$H NMR (400 MHz, CDCl$_3$) δ: 1.45 (4H, br, —CH$_2$CH$_2$—), 2.46 (2H, t), 2.58 (2H, t), 2.62 (2H, t), 2.84 (2H, t).

To a solution of the thus-obtained N-(2'-cyanoethyl)-1,4-diaminobutane (2.8 g, 20 mmole) in dichloromethane (70 ml) was added dropwise a solution of di-tert-butyldicarbonate (9.6 g, 44 mmole) in dichloromethane (10 ml) at room temperature, and the mixture was stirred for twelve hours. The organic solvent was removed in vacuo and the residual oil was dissolved in ethyl acetate (100 ml), followed by washing with saturated NaHCO$_3$ (2×50 ml), water (2×50 ml) and brine (50 ml), drying (MgSO$_4$), filtering and evaporation. The resulting crude viscous oil was purified by flash chromatography on silica gel, yielding pure N-(2'-cyanoethyl)-N,N'-(di-tert-butoxycarbonyl)-1,4-diaminobutane as a colorless, viscous oil (4.2 g, 75% yield). $^1$H NMR (400 MHz, CDCl$_3$) δ: 1.44 (9H, t-Boc), 1.46 (9H, merged s, t-Boc), 2.60 (2H, m), 3.15 (2H, m), 3.28 (2H, t), 3.45 (2H, t); CIMS(m/e): 342 (M$^+$+1, 62.7%), 239 (100%), 186 (83.1%).

To a suspension of LAH (0.6 g, 16.3 mmole) in dry ether (100 ml) was added a solution of the N-(2'-cyanoethyl)-N, N'-(di-tert-butoxycarbonyl)-1,4-diaminobutane (1.6 g, 4.6 mmole) in dry ether (50 ml) dropwise at 0° C., and the mixture was stirred for thirty minutes. The excess LAH was quenched with 1N NaOH at 0° C., and the resulting white suspension was filtered through Celite and washed with ether, and the ether extract was washed with brine, dried (MgSO$_4$), filtered and evaporated in vacuo. The resulting crude oil was purified by flash chromatography on silica gel, yielding pure N-(3'-aminopropyl)-N,N'-(di-tert-butoxycarbonyl)-1,4-diaminobutane 301 (1.1 g, 68% yield) as a colorless oil. $^1$H NMR (400 MHz, CDCl$_3$) δ: 1.44 (18H, s, 2(t-Boc)), 2.68 (2H, t), 3.05–3.25 (6H, br), 4.65 (1H, br); CIMS(m/e): 346 (M$^+$+1, 100%), 290 (3.1%), 246 (32.2%).

Preparation of compound 342: To a solution of 340 (1.0 g, 1.99 mmole) and 301 (1.03 g, 2.98 mmole) in methanol (60 ml) was added 3 Å molecular sieves (4.00 g) and NaCNBH$_3$ (187.1 mg, 2.98 mmole). The reaction mixture was stirred at room temperature for sixteen hours. After filtering through Celite, methanol was removed in vacuo. The resulting residue was purified by flash chromatography on silica gel (first 10:1 chloroform:methanol, and then 15:1:1 chloroform:methanol: isopropylamine), yielding 3β-N-1{N-[3-(4-tert-butoxycarbonylaminobutyl)-3-tert-butoxycarbonyl]-1,3-diaminopropane}-7α,24ζ-diacetoxy-5α-cholestane 342 (1.4 g, 85% yield). $^1$H NMR (400 MHz, CDCl$_3$) δ: 0.65 (3H, s, 18-CH$_3$), 0.80 (3H, s, 19-CH$_3$), 0.88 (9H, m, 21-CH$_3$, 26-CH$_3$, 27-CH$_3$), 1.45 (18H, s, 2(t-Boc)), 2.05 (3H, s, —OCOCH$_3$), 2.08 (3H, s, —OCOCH$_3$), 2.42 (1H, m, 3α-H), 4.67 (1H, m, 24ζ-H), 4.85 (1H, m, 7β-H); CIMS(m/e): 832 (M$^+$+1, 22.5%), 758 (100%), 698 (33.4%), 658 (44.7%), 548 (68.0%).

Preparation of compound 343: To a solution of 342 (1.0 g, 1.2 mmole) in methanol (40 ml) was added methanol saturated with HCl gas (10 ml). The reaction mixture was stirred at room temperature for twenty-four hours. After removing the methanol in vacuo, the crude product was purified by flash chromatography on silica gel, eluting with dichloromethane:methanol:ammonium hydroxide (7.5:2:0.5), producing 3β-N-1-{N-[3-(4-aminobutyl)]-1,3-diaminopropane}-7α,24ζ-dihydroxy-5α-cholestane 343, which was dissolved in methanol, treated with methanolic HCl and evaporated to give 343-3 HCl (382 mg, 58%). $^1$H NMR (400 MHz, CD$_3$OD) δ: 0.73 (3H, s, 18-CH$_3$), 0.89 (3H, s, 19-CH$_3$), 3.01 (2H, t, —CH$_2$N—), 3.12 (2H, t, —CH$_2$N—), 3.18 (6H, m, 3α, 24ζ-H and 2(—CH$_2$—)), 3.80 (1H, m, 7β-H); MS(+FAB): 548 (M$^+$+1, 100%), 531 (50.8%), 477 (21.8%)

EXAMPLE G

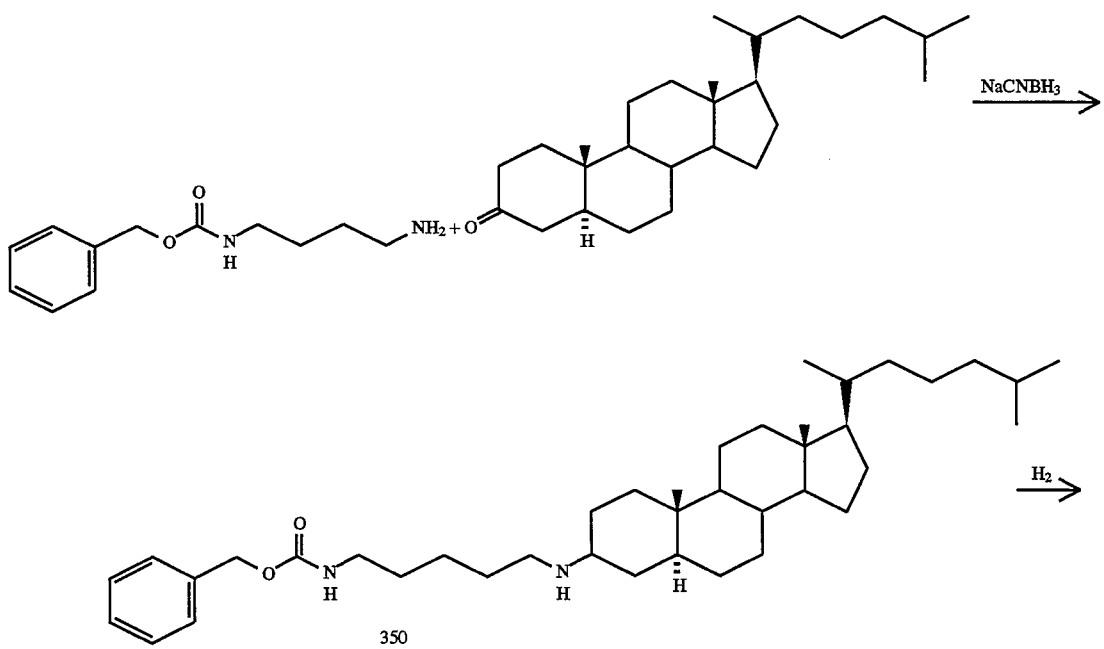

350

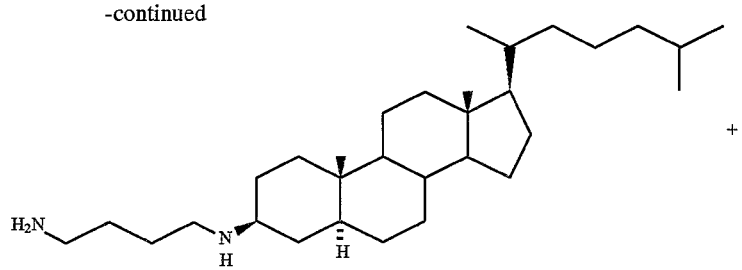

351

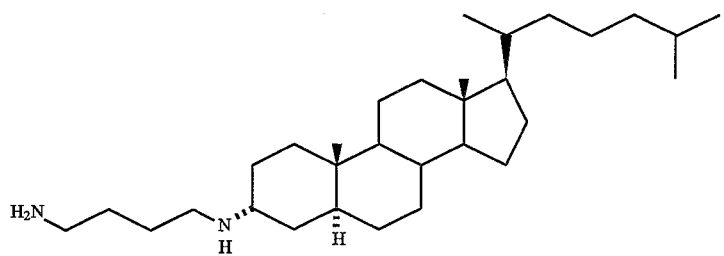

352

Diamine steroids 351 and 352 were made according to the above reaction scheme. Compound 350 was prepared in a manner analogous to the preparation of compound 315 above, and compound 350 was converted to compounds 351 and 352 using catalytic transfer hydrogenation (10% Pd/carbon, 1,4-cyclohexadiene).

In general, the compounds of the invention may be prepared in neutral or salt form. Pharmaceutically acceptable salts include those formed with free amino groups such as those derived from hydrochloric, phosphoric, sulfuric, acetic, trifluoroacetic, oxalic, tartaric acids, etc., and those formed with free carboxyl groups such as those derived from sodium, potassium, ammonium, calcium, ferric hydroxides, isopropylamine, triethylamine, 2-ethylamino, ethanol, histidine, procaine, etc.

Biological Testing

Antimicrobial and antifungal susceptibility testing on a compound of the invention may be performed using the following aerobes and yeast assays to determine Minimum Inhibitory Concentration (MIC) values. Testing is performed using microdilution broth assays (National Committee for Clinical Laboratory Standards Document M7-A2, NCCLS, 1990).

Steroid Stock Solution: Asteroid compound is weighed on an analytical balance and transferred to a polypropylene tube. A solution is prepared at a concentration of 1.024 mg/ml by dissolving the steroid powder in autoclaved (121° C., 20 psi, 20 minutes) deionized water. This steroid solution is used immediately, stored for up to ten days at 4° C., or stored long-term at −70° C. in 1 ml aliquots in polypropylene cryovials.

Aerobes-Assay Broth Medium: Mueller-Hinton broth (MHB) (BBL® catalog no. 11443) is used in microtiter plates for diluting the steroid stock solution and for diluting the bacterial inoculum. Colonies from an overnight plate of bacteria are cultured in 5-ml prepared tubes of MHB (BBL® catalog no. 95834) to the logarithmic phase of growth for inoculating the microtiter plates.

Yeast-Assay Broth Medium: Antibiotic medium 3 (M3) (BBL® catalog no. 10932) is used in the microtiter plates for diluting the steroid stock solutions and for diluting the yeast inoculum.

Aerobes-Assay Standardizing Inoculum: Inoculum is prepared by taking a sample of bacteria from a 16–20 hour plate culture and inoculating into 5 ml of MHB (BBL® catalog no. 95834) to an absorbance reading of approximately 0.02 at 600 nm ($Ab_{600}$) on a Beckman DU®-64 spectrophotometer. The culture is incubated at 35°–37° C. with shaking (New Brunswick incubator shaker Model G25) and the growth monitored spectro-photometrically until it reaches mid-logarithmic phase ($Ab_{600}$ of approximately 0.06). This absorbance represents approximately $1 \times 10^8$ colony-forming units per milliliter (CFU/ml). The culture is then diluted to approximately $1 \times 10^6$ CFU/ml in autoclaved MHB (BBL® catalog no. 11443) to produce the inoculum. A sample of the inoculating culture is diluted in 3 mM phosphate buffer (pH 7.2) through a series of 1:10 dilutions, and the $10^{-4}$ and $10^{-5}$ dilutions are plated, incubated overnight at 35°–37° C., and counted the next day to verify inoculum size. The bacteria used in the antimicrobial testing are S. aureus ATCC 29213, E. coli ATCC 25922, and P. aeruginosa ATCC 27853.

Yeast-Assay Standardizing Inoculum: The yeast culture, C. albicans ATCC 14053, is grown on Sabouraud dextrose agar overnight at 30° C. A sample from this culture is diluted in M3 broth until a transmittance (T) of 95% at 530 nm is obtained on a Beckman DU®-64 spectrophotometer to produce the inoculum. A sample of the inoculating culture is diluted in 3 mM phosphate buffer (pH 7.2) through a series of 1:10 dilutions, and the $10^{-4}$ and $10^{-5}$ dilutions are plated on Sabouraud agar, incubated overnight at 30° C., and counted the next day to verify inoculum size.

Microtiter Plates: Microtiter plates (Corning manuf. no. 2585096) are prepared using a Beckman Biomek® 1000 automated laboratory workstation in combination with manual techniques. A microtiter plate is filled with diluent broth using the Biomek® 1000. Steroid stock solution is manually added to the top drug wells of the microtiter plate using a Rainin Pipetman® Model P-200. The steroid is serially diluted in two-fold dilutions using the Biomek® 1000. A volume of 100 microliters of the standardized bacterial inoculum is added to every well of the microtiter plates, except the blanks, using an Eppendorf Repeater® Model 4780 pipette equipped with an Eppendorf 5-ml Combitip (catalog no. 22 26 130-4).

The steroid is tested in duplicate. In addition to the test steroid, a non-treated growth control and a squalamine reference standard (shark liver preparation) are included to validate the assay. Three standard compounds (gram-negative bacterial activity, gram-positive and gram-negative bacterial activity, and negative control) are also included. For the yeast assay, a reference antifungal such as amphotericin B is used.

The final concentrations of the steroid solution in the wells range from 0.25–256 µg/ml. The final concentration of bacteria in the wells is 1–5×10$^5$ CFU/ml. The final volume in the wells is 200 µl.

Incubation: The microtiter plates are incubated overnight (aerobes assay: 16–20 hours, 35°–37° C.; yeast assay: 24 hours, 30° C.) in a Precision mechanical convention oven incubator Model 30M. Plates are never stacked more than four high.

Results: The MIC value (lowest concentration of the compound that completely inhibits the growth of the test organism) is determined using the unaided eye. In addition, the absorbance at 630 nm is read on a Dynatech MR5000 Microplate Reader Version 2.7. Results for some steroid compounds according to the invention are provided in the table below. For comparative purposes, results for squalamine are also provided.

TABLE

| Compound | MIC values (µg/ml) | | | |
|---|---|---|---|---|
| | S. aureus | E. coli | P. aeruginosa | C. albicans |
| 303# | 8 | 128–256 | 128 | 256 |
| 304# | 2–4 | 128 | 128 | 128 |
| 318@ | 128 | 32 | 64 | >256 |
| 319@ | 128 | 64 | 64 | >256 |
| 328# | 8–16 | 64 | 128 | 64 |
| 343# | 4–16 | 32 | 128 | 64 |
| 351† | 16 | >256 | >256 | >256 |
| 352† | 4 | >256 | >256 | 64 |
| squalamine* | 0.5–1 | 2–4 | 16 | 8 |

Notes:
@- as free base;
- as 3HCl salt;
† - as 2HCl salt;
*reference standard, as 2HCl-TFA salt, prepared from shark liver.

Utilities

Steroid compounds of the invention may be used as antimicrobial, antibacterial, antifungal, antiparasitic, e.g. antiprotozoal, or anti-infective agents. Steroids of the present invention have a broad range of potent antibiotic activity against a plurality of microorganisms including gram-positive and gram-negative bacteria, fungi, protozoa and the like, as well as parasites.

The steroids may be therapeutically administered to a host or patient, for example a human or non-human animal, in an amount effective to inhibit growth of a target cell. When so used, they provide a method for treating or controlling microbial infection caused by organisms which are sensitive to the steroids. Such treatment may comprise administering to a host organism or tissue susceptible to or affiliated with a microbial infection an antimicrobial amount of at least one of the steroids.

Because of, e.g., the antibiotic, antimicrobial, and antibacterial properties of the steroids, they may also be used as preservatives, sterilants, antifungal, bactericides, disinfectants or the like of materials susceptible to microbial contamination. Steroids of the invention may be applied as a solution in a suitable solvent or vehicle to treat a surface to prevent or control microbial or fungal contamination, proliferation or growth.

Depending on the particular use, a composition in accordance with the invention may contain an effective antimicrobial amount, an effective antiparasitic amount, an effective antibiotic amount, an effective anti-infective amount, etc. of one or more of the hereinabove described steroids which have such activity. The steroids may be therapeutically administered by direct application of the steroids to the target cell or by indirect application through systemic administration. The steroids may also be applied in the form of a solution directly to a surface to be treated or disinfected.

Therapeutic Administration and Compositions

Modes of administration include, but are not limited to, transdermal, intramuscular, intraperitoneal, intravenous, subcutaneous, intranasal, inhalation, and oral routes. The compounds may be administered by any convenient route, for example by infusion or bolus injection by absorption through epithelial or mucocutaneous linings (e.g., oral mucosa, rectal and intestinal mucosa, etc.) and may be administered together with other biologically active agents. Administration may be systemic.

The present invention also provides pharmaceutical compositions. Such compositions comprise a therapeutically effective amount of a compound of the invention, and a pharmaceutically acceptable carrier or excipient. Examples of such a carrier include but are not limited to saline, buffered saline, dextrose, water, glycerol, ethanol, and combinations thereof. The formulation should suit the mode of administration.

The composition, if desired, may also contain minor amounts of wetting or emulsifying agents, or pH buffering agents. The composition may be in the form of a liquid solution, suspension, emulsion, tablet, pill, capsule, sustained release formulation, or powder. The composition may be formulated as a suppository, with traditional binders and carriers such as triglycerides. Oral formulations may include standard carriers such as pharmaceutical grades of mannitol, lactose, starch, magnesium stearate, sodium saccharine, cellulose, magnesium carbonate, etc.

Various delivery systems are known and may be used to administer a therapeutic compound of the invention, e.g., encapsulation in liposomes, microparticles, microcapsules and the like.

In a preferred embodiment, the composition is formulated in accordance with routine procedures as a pharmaceutical composition adapted for intravenous administration to humans. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it may be dispensed with an infusion bottle containing sterile pharmaceutical-grade water or saline. Where the composition is administered by injection, an ampoule of sterile water for injection or saline may be provided so that the ingredients may be mixed prior to administration.

The amount of the therapeutic compound of the invention which will be effective in the treatment of a particular disorder or condition will depend on the nature of the disorder or condition, and can be determined by standard clinical techniques. The precise dose to be employed in the formulation will also depend on the route of administration and the seriousness of the disease or disorder, and should be decided according to the judgment of the practitioner and each patient's circumstances. Effective therapeutic doses may be determined from extrapolations of dose-response curves derived from in vitro or animal-model test systems. Effective antibiotic doses may be determined using doses for commercially available antibiotic compounds in the *Physician's Desk Reference*, Medical Economics Company, Inc., Oradell, N.J., 1990, as guidelines.

Suitable dosage ranges for intravenous administration are generally about 20 micrograms to 40 milligrams of active compound per kilogram body weight. Suitable dosage ranges for intranasal administration are generally about 0.01 mg/kg body weight to 1 mg/kg body weight. Suitable dosage ranges for topical administration are generally at least about 0.01% by weight. Suitable dosages for oral administration are generally about 500 micrograms to 800 milligrams per kilogram body weight, more specifically about 50–200 mg/kg body weight. In many cases it is not necessary to employ the steroid compound in an amount greater than 2.0% by weight. Suppositories generally contain, as the active ingredient, a compound of the invention in the range of 0.5% to 10% by weight; oral formulations preferably contain 10% to 95% active ingredient.

The invention also provides a pharmaceutical pack or kit comprising one or more containers filled with one or more of the active ingredients of the pharmaceutical compositions of the invention. Associated with such containers may be a notice in the form prescribed by a governmental agency regulating the manufacture, use or sale of pharmaceuticals or biological products, which notice reflects approval by the agency of manufacture, use or sale for human administration.

We claim:
1. A compound of Formula III:

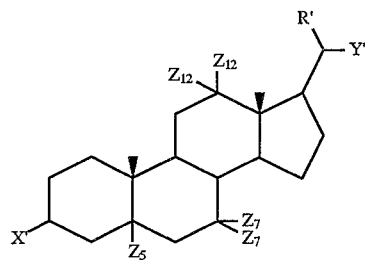

(III)

wherein:
the steroid ring nucleus is saturated;
the steroid ring substituent $Z_5$ is α-H or β—H;
one of the steroid ring substituents $Z_7$ is H and the other is H or OH;
one of the steroid ring substituents $Z_{12}$ is —H and the other is —H or —OH;
X' is a polyamine side chain of the formula

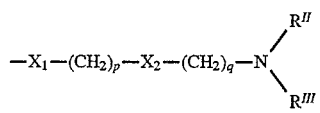

where one of $X_1$ and $X_2$ is —N($R^{IV}$) and the other is independently selected from the group consisting of —N($R^V$), —O, —S and —CH$_2$, where $R^{IV}$ and $R^V$ are each independently —H or —(C$_1$-C$_3$)-alkyl, p and q are each independently an integer of from 0 to 5 but both p and q are not 0, and $R^{II}$ and $R^{III}$ are each independently —H, —(C$_1$-C$_3$)-alkyl or —(CH$_2$)$_r$—N(R$_{10}$) (R$_{11}$) where r is an integer from 2 to 5 and R$_{10}$ and R$_{11}$ are each independently —H or —(C$_1$-C$_3$)-alkyl;

R' is —H or —(C$_1$-C$_3$)-alkyl; and

Y' is —(C$_1$-C$_{10}$)-alkyl substituted with —CO$_2$H, —OH, —NH—SO$_2$CF$_3$, —SO$_3$H, —PO$_3$H$_2$, —OSO$_3$H, —CF$_3$, —F,

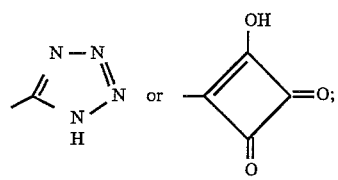

provided that the compound is not 3β—(N-[3-aminopropyl]-1,4-butanediamine)-7α,24ζ-dihydroxy-5α-cholestane 24-sulfate;

or a pharmaceutically acceptable salt thereof.

2. A compound according to claim 1, wherein:
the steroid ring substituent $Z_5$ is α-H;
one $Z_7$ is β—H and the other is α-H or α—OH;
both steroid ring substituents $Z_{12}$ are hydrogen;
one of $X_1$ and $X_2$ is —N($R^{IV}$) and the other is independently —N($R^V$), —O or —S, $R^{IV}$ and $R^V$ are each hydrogen or methyl, p and q are each independently 2, 3, 4 or 5, and $R^{II}$ and $R^{III}$ are each independently hydrogen or methyl;

R' is methyl; and

Y' is (C$_1$-C$_{10}$)-alkyl substituted with —CO$_2$H, —SO$_3$H, —PO$_3$H$_2$, —OSO$_3$H, —OH, —NHSO$_2$CF$_3$,

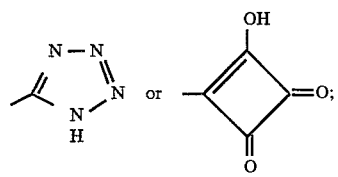

or a pharmaceutically acceptable salt thereof.

3. A compound according to claim 2, wherein $X_1$ and $X_2$ are each —NH, and p and q are each independently 3 or 4; or a pharmaceutically acceptable salt.

4. A compound of the Formula III:

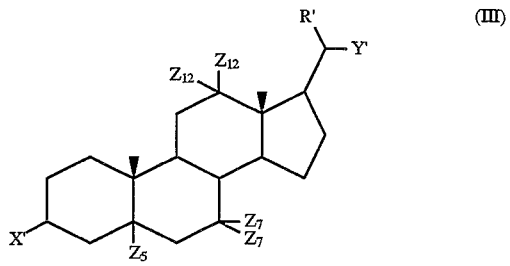

(III)

wherein:
the steroid ring nucleus is saturated;
the steroid ring substituent $Z_5$ is selected from α-H and β-H;

each of the steroid ring substituents $Z_7$ is selected from the group consisting of —H, —OH, —SH, —F, —NH$_2$, —(C$_1$-C$_3$)-alkyl and —(C$_1$-C$_3$)-alkoxy;

one of the steroid ring substituents $Z_{12}$ is —H and the other is selected from the group consisting of —H and —OH;

X' is a side chain having at least three amine groups of the formula $$-X_1-(CH_2)_p-X_2-(CH_2)_q-N\diagup^{R^{II}}_{R^{III}}$$

where one of $X_1$ and $X_2$ is —N(R$^{IV}$) and the other is independently selected from the group consisting of —N(R$^V$), —O and —S, where R$^{IV}$ and R$^V$ are each independently —H or —(C$_1$-C$_3$)-alkyl, p and q are each independently an integer of from 2 to 5, and R$^{II}$ and R$^{III}$ are each independently selected from the group consisting of —H, —(C$_1$-C$_3$)-alkyl and —(CH$_2$)$_r$—N(R$_{10}$)(R$_{11}$) where r is an integer from 2 to 5 and R$_{10}$ and R$_{11}$ are each independently selected from the group consisting of —H and —(C$_1$-C$_3$)-alkyl;

R' is selected from the group consisting of —H and —(C$_1$-C$_3$)-alkyl; and

Y' is (C$_1$-C$_{10}$)-alkyl unsubstituted or substituted with —CO$_2$H, —OH, —NH—SO$_2$CF$_3$, —SO$_3$H, —PO$_3$H$_2$, —OSO$_3$H, —CF$_3$, —F,

[tetrazole structure] or [squaric acid structure] ;

provided that the compound is not 3β-(N-[3-aminopropyl]-1,4-butanediamine)-7α,24ζ-dihydroxy-5α-cholestane 24-sulfate;

or a pharmaceutically acceptable salt thereof.

5. A compound according to claim 4, wherein X' has four amine groups; or a pharmaceutically acceptable salt thereof.

6. A compound according to claim 4, wherein X' is —NH—(CH$_2$)$_3$—NH—(CH$_2$)$_4$—NH—(CH$_2$)$_3$—NH$_2$; or a pharmaceutically acceptable salt thereof.

7. A compound according to claim 4, which has the formula

[steroid structure with X' and Y substituents]

wherein Y' has the formula $$-(CH_2)_t-\underset{H}{\overset{R_{21}}{C}}-(CH_2)_u-R_{22}$$

where one of $R_{21}$ and $R_{22}$ is —H or —(C$_1$-C$_3$)-alkyl and the other is —CO$_2$H, —OH, —NH—SO$_2$CF$_3$, —SO$_3$H, —PO$_3$H$_2$, —OSO$_3$H, —CF$_3$, —F,

[tetrazole structure] or [squaric acid structure] , t is an integer of from 0 to 5, and u is an integer of from 0 to 3, provided that $R_{21}$, $R_{22}$, t and u are selected such that Y' is a (C$_1$-C$_{10}$)-alkyl as defined in claim 5; or a pharmaceutically acceptable salt thereof.

8. A compound according to claim 7, wherein X' is α to the steroid ring nucleus; or a pharmaceutically acceptable salt thereof.

9. A compound according to claim 8, wherein X' is β to the steroid ring nucleus; or a pharmaceutically acceptable salt thereof.

10. A compound of the formula:

[steroid structure with X" and Y" substituents]

wherein the steroid ring nucleus is optionally substituted with a 7α-OH;

Y" is —CO$_2$H, —OH, —NH—SO$_2$CF$_3$, —SO$_3$H, —PO$_3$H$_2$, —OSO$_3$H, —CF$_3$, —F,

[tetrazole structure] or [squaric acid structure] ;

and

X" is a polyamine side chain of the formula $$-X_1-(CH_2)_p-X_2-(CH_2)_q-N\diagup^{R^{II}}_{R^{III}}$$

where one of $X_1$ and $X_2$ is —NH and the other is —NH, —O or —S, p and q are each independently an integer of from 2 to 5, and $R^{II}$ and $R^{III}$ are each independently —H, —($C_1$-$C_3$)-alkyl or —$(CH_2)_r$—$N(R_{10})(R_{11})$ where r is an integer from 2 to 5 and $R_{10}$ and $R_{11}$ are each independently —H or —($C_1$-$C_3$)-alkyl;

or a pharmaceutically acceptable salt thereof.

11. A compound according to claim 10, wherein Y" is —$CO_2H$ or —$SO_3H$; or a pharmaceutically acceptable salt thereof.

* * * * *

UNITED STATES PATENT AND TRADEMARK OFFICE
CERTIFICATE OF CORRECTION

PATENT NO. : 5,637,691
DATED : June 10, 1997
INVENTOR(S) : Leah L. FRYE et al.

It is certified that error appears in the above-identified patent and that said Letters Patent is hereby corrected as shown below:

On the patent title page, Field [22], "Mar. 16, 1994" should read --Mar. 10, 1994--.

In the abstract, on the patent title page, Field [57], line 2, "asteroid" should read --a steroid--.

In column 1, line 39, "asteroid" should read --a steroid--.

In column 2, line 39, "-N($R^{IV}$)" should read -- -N($R^{IV}$)- --.

In column 2, line 40, "-N($R^V$, -O, -S" should read -- -N($R^V$)-, -O-, -S- --.

In column 2, line 41, "-$CH_2$," should read -- -$CH_2$-, --.

In column 4, line 29, "-S" should read -- -S- --.

UNITED STATES PATENT AND TRADEMARK OFFICE
CERTIFICATE OF CORRECTION

PATENT NO. : 5,637,691
DATED : June 10, 1997
INVENTOR(S) : Leah L. FRYE et al.

It is certified that error appears in the above-identified patent and that said Letters Patent is hereby corrected as shown below:

In column 4, line 30, "-O," should read -- -O-, --.

In column 6, line 40, in Formula (III), the variable " A' " should be --R'--.

In column 7, line 8, "-N($R^{IV}$)" should read -- -N($R^{IV}$)- --.

In column 7, line 9, "-N($R^V$), -O, -S" should read -- -N($R^V$)-, -O-, -S- --.

In column 7, line 10, "-$CH_2$," should read -- -$CH_2$-, --.

In column 7, line 19, "-NH-" should be deleted.

In column 7, line 20, "$SO_2CF_3$," should read -- -NH-$SO_2CF_3$,--.

In column 8, line 65, the last formula on the page should read as follows:

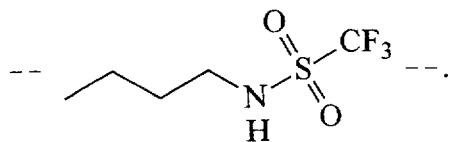

UNITED STATES PATENT AND TRADEMARK OFFICE
CERTIFICATE OF CORRECTION

PATENT NO. : 5,637,691
DATED : June 10, 1997
INVENTOR(S) : Leah L. FRYE et al.

It is certified that error appears in the above-identified patent and that said Letters Patent is hereby corrected as shown below:

In column 119, line 49, "Asteroid" should read -- A steroid --.

In claim 1, column 123, line 66, "-N($R^{IV}$)" should read -- -N($R^{IV}$)- --.

In claim 1, column 124, line 1, "-N($R^V$), -O, -S and -$CH_2$," should read -- -N($R^V$)-, -O-, -S- and -$CH_2$- --.

In claim 2, column 124, line 30, "-N($R^{IV}$)" should read -- -N($R^{IV}$)- --.

In claim 2, column 124, line 31, "-N($R^V$), -O or -S," should read -- -N($R^V$)-, -O- or -S-, --.

In claim 3, column 124, line 50, "-NH," should read -- -NH-, --.

In claim 4, column 125, line 18, "-N($R^{IV}$)" should read -- -N($R^{IV}$)- --.

UNITED STATES PATENT AND TRADEMARK OFFICE
CERTIFICATE OF CORRECTION

PATENT NO. : 5,637,691
DATED : June 10, 1997
INVENTOR(S) : Leah L. FRYE et al.

It is certified that error appears in the above-identified patent and that said Letters Patent is hereby corrected as shown below:

In claim 4, column 125, line 20, "$-N(R^V)$, $-O$ and $-S$," should read -- $-N(R^V)-$, $-O-$ and $-S-$, --.

In claim 7, column 125, line 55, in the formula, "Y" should be --Y'--.

In claim 7, column 126, line 22, "claim 5;" should read --claim 4;--.

In claim 9, column 126, line 27, "claim 8," should read --claim 7,--.

In claim 10, column 126, line 66, "$-NH$ and the other is $-NH$, $-O$" should read -- $-NH-$ and the other is $-NH-$, $-O-$ --.

In claim 10, column 126, line 27, "$-S$," should read -- $-S-$, --.

Signed and Sealed this

Twenty-third Day of February, 1999

Attest:

Q. TODD DICKINSON

*Attesting Officer*  *Acting Commissioner of Patents and Trademarks*